United States Patent
Bell et al.

[11] Patent Number: 6,015,825
[45] Date of Patent: Jan. 18, 2000

[54] TRIAZOLE ANTIFUNGAL AGENTS

[75] Inventors: Andrew Simon Bell; Michael Jonathan Fray; Alan Patrick Marchington; Kenneth Richardson; Peter Thomas Stephenson; Peter John Whittle, all of Sandwich, United Kingdom

[73] Assignee: Pfizer Inc., New York, N.Y.

[21] Appl. No.: 08/983,006

[22] PCT Filed: Jun. 5, 1996

[86] PCT No.: PCT/EP96/02470

§ 371 Date: Dec. 19, 1997

§ 102(e) Date: Dec. 19, 1997

[87] PCT Pub. No.: WO97/01552

PCT Pub. Date: Jan. 16, 1997

[30] Foreign Application Priority Data

Jun. 25, 1995 [GB] United Kingdom .................. 9512961

[51] Int. Cl.[7] .......................... A61K 31/41; C07D 403/10
[52] U.S. Cl. .................... 514/383; 548/266.2; 548/266.6
[58] Field of Search .............................. 548/266.2, 266.6; 514/383

[56] References Cited

U.S. PATENT DOCUMENTS 5,629,332  5/1997  Kodama et al. ..................... 514/383
5,648,372  7/1997  Naito et al. ........................ 514/383

FOREIGN PATENT DOCUMENTS 0357241    3/1990   European Pat. Off.
WO92/17474 10/1992  WIPO.
WO93/07139  4/1993  WIPO.

OTHER PUBLICATIONS

Cram and Hammond, "Organic Chemistry", McGraw–Hill Book Co., NY (1964) 2nd ed., pp. 565–567.

*Primary Examiner*—Patricia L. Morris
*Attorney, Agent, or Firm*—Peter C. Richardson; Paul H. Ginsburg; Bryan C. Zielinski

[57] ABSTRACT

The invention relates to compounds of the formula (I)

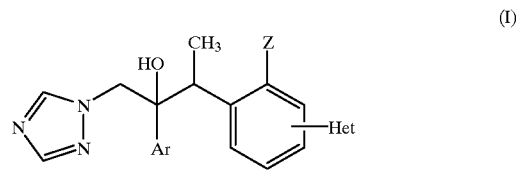

and pharmaceutically acceptable salts thereof, wherein Ar, Z and Het are as defined herein. The compounds of formula (I) possess activity as antifungal agents. The invention also relates to pharmaceutical compositions containing said compounds of formula (I) and to methods of treating fungal infections by administering said compounds of formula (I).

8 Claims, No Drawings

TRIAZOLE ANTIFUNGAL AGENTS

This invention relates to triazoe derivatives which have antifungal activity and are useful in the treatment of fungal infections in animals, including humans.

Thus the invention provides compounds of the formula:

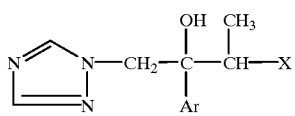

(I)

and their pharmaceutically acceptable salts,
where Ar is a phenyl group substituted by 1 to 3 substituents each independently selected from halo and $CF_3$;
and X is a group of the formula:

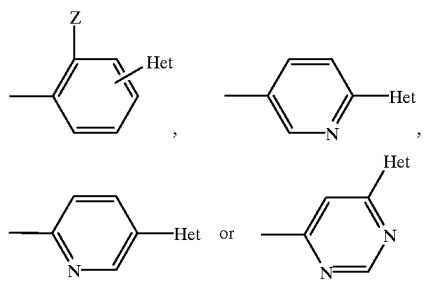

wherein Z is H or F, and
in which Het is a 5-membered nitrogen-containing aromatic heterocyclic group optionally containing an oxygen or sulfur atom and attached to the phenyl, pyridyl or pyrimidinyl group by a carbon or nitrogen atom and optionally substituted by 1 to 3 substituents each independently selected from halo; $C_1$–$C_4$ alkyl; ($C_1$–$C_4$ alkoxy)methyl; 2-($C_1$–$C_4$ alkoxy) ethoxymethyl; 2-hydroxyethoxymethyl; cyanomethyl; —$NR^1R^2$ or —$CH_2CONR^1R^2$ where $R^1$ and $R^2$ are each independently H or $C_1$–$C_4$ alkyl; phenylthio or phenyl-($C_1$ or $C_2$ alkyl) in both of which said phenyl group is optionally substituted by halo, trifluoromethyl or $C_1$–$C_4$ alkyl; —NHCO($C_1$–$C_4$ alkyl); —$NHSO_2$($C_1$–$C_4$ alkyl); —$NHCONR^1R^2$ where $R^1$ and $R^2$ are as defined above; mercapto; and —$S(O)_n$($C_1$–$C_4$ alkyl) where n is 0, 1 or 2.

"Halo" means F, Cl, Br or I. Preferred alkyl groups are methyl, ethyl and isopropyl, and preferred alkoxy groups are methoxy and ethoxy.

Z is preferably H.

Preferably, "Het" is a pyrazolyl, imidazolyl, triazolyl, thiadiazolyl, oxadiazolyl, pyrrolyl, thiazolyl or tetrazolyl group, optionally substituted as defined above, particularly a pyrazol-1-yl, pyrazol-3-yl, pyrazol-4-yl, imidazol-1-yl, imidazol-2-yl, imidazol-4-yl, 1,2,3-triazol-1-yl, 1,2,3-triazol-2-yl, 1,2,3-triazol-4-yl, 1,2,4-triazol-1-yl, 1,2,4-triazol-3-yl, 1,2,4-triazol-4-yl, 1,3,4-thiadiazol-2-yl, 1,3,4-oxadiazol-2-yl, 1,2,4-oxadiazol-5-yl, pyrrol-1-yl, thiazol-5-yl or tetrazol-5-yl group, these groups being optionally substituted by 1 to 3 substituents as defined above, and particularly by 1 to 3 (preferably by 1 or 2) substituents each independently selected from chloro, bromo, fluoro, iodo, $C_1$–$C_3$ alkyl, amino, ethoxymethyl, 2-methoxyethoxymethyl, 2-hydroxyethoxymethyl, methylthio, methanesulphonyl, mercapto, phenylthio, methanesulfonamido, 3-methylureido, cyanomethyl, carbamoylmethyl, acetamido and benzyl.

The most preferred compounds are either unsubstituted or have one substituent as defined above.

Specific examples of "Het" include pyrazol-1-yl, 3-aminopyrazol-1-yl, 1-ethoxymethylpyrazol-4-yl, 1-ethoxymethylpyrazol-5-yl, 4-bromo-pyrazol-3-yl, 3-methanesulfonamidopyrazol-1-yl, 3-(3-methylureido) pyrazol-1-yl, 3-acetamidopyrazol-1-yl, 1-methylpyrazol-5-yl, 1-methylpyrazol-3-yl, 1-ethylpyrazol-5-yl, 1-isopropylpyrazol-5-yl, 1-ethoxymethylpyrazol-5-yl, 1-carbamoylmethylpyrazol-3-yl, 1-cyano-methylpyrazol-3-yl, pyrazol-3-yl, pyrazol-4-yl, 3-methylpyrazol-4-yl, 1-methylimidazol-2-yl, imidazol-1-yl, 2-methylimidazol-1-yl, 1-ethoxymethyl-2-phenylthioimidazol-5-yl, 1-ethoxymethylimidazol-2-yl, 4-methylimidazol-1-yl, 1-ethoxymethylimidazol-5-yl, imidazol-2-yl, 1-methylimidazol-5-yl, 1-ethylimidazol-5-yl, 1-methyl-2-phenylthioimidazol-5-yl, imidazol-4-yl, 1,2,3-triazol-1-yl, 1,2,3-triazol-2-yl, 1,2,4-triazol-1-yl, 1-ethoxymethyl-1,2,4-triazol-5-yl, 1-ethoxymethyl-3-methylthio-1,2,4-triazol-5-yl, 1,2,3-triazol-4-yl, 1-(2-methoxyethoxymethyl)-1,2,3-triazol-5-yl, 1-benzyl-1,2,3-triazol-5-yl, 1-(2-hydroxyethoxymethyl)-1,2,3-triazol-5-yl, 5-methyl1,2,3-triazol-4-yl, 3-methylthio-1,2,4-triazol-1-yl, 1-ethoxymethyl-1,2,3-triazol-5-yl, 4-methyl-1,2,4-triazol-3-yl, 3-mercapto-4-methyl-1,2,4-triazol-5-yl, 1-methyl-1,2,4-triazol-5-yl, 1-ethoxymethyl-1,2,3-triazol-4-yl, 2-ethoxymethyl-1,2,3-triazol-4-yl, 1,2,4-triazol-4-yl, 4-chloro-1,2,3-triazol-5-yl, 4-bromo-1,2,3-triazol-5-yl, 4-iodo-1,2,3-triazol-5-yl, 4-fluoro-1,2,3-triazol-5-yl, 1,2,4-triazol-3-yl, 5-methanesulfonyl-1,2,4-triazol-3-yl, 3-methanesulphonyl-1,2,4-triazol-1-yl, 1-ethoxymethyl-3-methanesulphonyl-1,2,4-triazol-5-yl, 5-amino-1,3,4-thiadiazol-2-yl, 5-methyl-1,3,4-oxadiazol-2-yl, 5-methylthio-1,3,4-oxadiazol-2-yl, 5-methanesulphonyl-1,3,4-oxadiazol-2-yl, 3-amino-1,2,4-oxadiazol-5-yl, 5-amino-1,3,4-oxadiazol-2-yl, 1-methyl-tetrazol-5-yl, 1-benzyltetrazol-5-yl, tetrazol-5-yl, thiazol-5-yl and 2,5-dimethylpyrrol-1-yl.

X is preferably a group of the formula:

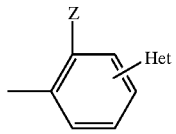

where Z is H or F,
and, more preferably,

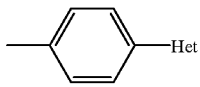

where "Het" is as defined above.
X is most preferably a group of the formula:

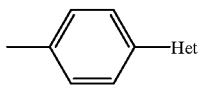

where "Het" is selected from (a) an unsubstituted 1,2,3-triazol-1-yl group, (b) an unsubstituted 1,2,4-triazol-1-yl or -4-yl group, (c) a 1,2,3- or 1,2,4-triazolyl group attached to the adjacent phenyl group by a carbon atom and optionally substituted on a nitrogen atom by $C_1$-$C_4$ alkyl (preferably methyl), or ($C_1$-$C_4$ alkoxy)methyl (preferably ethoxymethyl), (d) unsubstituted imidazol-1-yl, (e) an unsubstituted pyrazol-3-yl group, an unsubstituted pyrazol-4-yl group or 1-methylpyrazol-5-yl group, and (f) an imidazol-4-yl or 1-methylimidazol-5-yl group.

Ar is preferably a phenyl group substituted by 1 or 2 substituents each independently selected from halo and $CF_3$. More preferably, Ar is a phenyl group substituted by 1 or 2 substituents each independently selected from F, Cl and Br. Most preferably, Ar is 2,4-difluorophenyl, 2-chlorophenyl or 2-fluorophenyl. Where the compounds (I) can exist in tautomeric forms, it should be understood that the invention includes all the tautomers.

The pharmaceutically acceptable salts of the compounds of the formula (I) include acid addition salts formed from acids which form non-toxic salts such as the hydrochloride, hydrobromide, hydroiodide, sulphate or bisulphate, phosphate or hydrogen phosphate, acetate, maleate, fumarate, lactate, tartrate, citrate, gluconate, benzoate, methanesulphonate, benzenesulphonate and p-toluenesulphonate salts. Some of the compounds may also form basic salts such as sodium, potassium and tetraalkylammonium salts. For a review on suitable pharmaceutical salts see Berge et al, J. Pharm. Sci., 66, 1–19 (1977).

The compounds of the formula (I) contain at least two chiral centres (*) and therefore exist as at least two diastereoisomeric pairs of enantiomers, i.e.

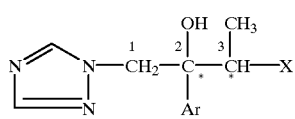

(I)

The invention includes both the individual stereoisomers of the compounds of formula (I) together with mixtures thereof. Separation of diastereoisomers may be achieved by conventional techniques, e.g. by fractional crystallisation, chromatography or H.P.L.C. of a diastereoisomeric mixture of a compound of the formula (I) or a suitable salt or derivative thereof. An individual enantiomer of a compound of the formula (I) may also be prepared from a corresponding optically pure intermediate or by resolution, either by H.P.L.C. of the racemate using a suitable chiral support or by fractional crystallisation of the diastereoisomeric salts formed by reaction of the racemate with a suitable optically active acid, e.g. 1R-(−) or 1S-(+)-10-camphorsulphonic acid, 3-bromocamphor-10-sulphonic acid or (−)-3-bromocamphor-8-sulphonic acid.

In general, the (2R,3S)-forms of the compounds (I) are preferred.

Preferred individual compounds include the following:
(2R,3S)-2-(2,4-difluorophenyl)-3-(4-[imidazol-1-yl]phenyl)-1-(1,2,4-triazol-1-yl)butan-2-ol,
(2R,3S)-2-(2,4-difluorophenyl)-3-(4-[1,2,3-triazol-1-yl]phenyl)-1-(1,2,4-triazol-1-yl)butan-2-ol,
(2R,3S)-2-(2,4-difluorophenyl)-3-(4-[1,2,3-triazol-4-yl]phenyl)-1-(1,2,4-triazol-1-yl)butan-2-ol,
(2R,3S)-2-(2,4-difluorophenyl)-3-(4-[1,2,4-triazol-1-yl]phenyl)-1-(1,2,4-triazol-1-yl)butan-2-ol,
(2R,3S)-2-(2,4-difluorophenyl)-3-(4-[1,2,4-triazol-3-yl]phenyl)-1-(1,2,4-triazol-1-yl)butan-2-ol,
(2R,3S)-2-(2,4-difluorophenyl)-3-(4-[1,2,4-triazol-4-yl]phenyl)-1-(1,2,4-triazol-1-yl)butan-2-ol, and
(2R,3S)-2-(2,4-difluorophenyl)-3-(4-[1-methylpyrazol-5-yl]phenyl)-1-(1,2,4-triazol-1-yl)butan-2-ol.

The compounds of formula (I) can be prepared as follows:

Route A

The compounds of the formula (I) can be prepared by the reduction of a 3-buten-2-ol derivative of the formula (II):

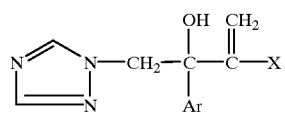

(II)

where Ar and X are as defined for formula (I).

In a typical procedure the reduction of the compound (II) is carried out by catalytic hydrogenation, e.g. using either a heterogeneous catalyst such as palladium, palladium or rhodium on carbon, Raney nickel, or a homogeneous catalyst, e.g. tris(triphenylphosphine) chlororhodium, both in a suitable organic solvent, e.g. ethanol or ethyl acetate. The reaction is preferably carried out at from room temperature up to the reflux temperature of the solvent and at a pressure of from 1 to 5 atmospheres (100–500 kPa), but generally proceeds satisfactorily at about room temperature and two atmospheres of hydrogen pressure. This reduction technique tends to result in end products (I) primarily in the (2R,3S) or (2R,3S/2S,3R) form.

The reduction can also be carried out using di-imide which can be generated in situ by the decomposition of azodicarboxylic acid potassium salt [J. Org. Chem., 1965, 30, 1965] or an acyl or sulphonyl hydrazide (e.g. p-toluenesulphonylhydrazide) either by the action of base, e.g. sodium ethoxide, or— by thermal decomposition in an appropriate solvent, e.g. ethanol, butanol or an hydrocarbon such as toluene or xylene [J. Am. Chem. Soc., 1961, 83, 3729; Tetrahedron, 1976, 32, 2157]. Using this method, sufficient quantities of both diastereomeric pairs, i.e. (2R,3S) and (2R,3R) or (2R,3S/2S,3R) and (2R,3R/2S,3S), are often produced for them to be separated by chromatography.

Catalytic hydrogenation at higher temperatures (e.g. 50° to 100° C.) and over a prolonged period (e.g. 15 to 20 hours) will, at the same time as reducing the methylene group, simultaneously remove any protecting groups such as ($C_1$-$C_4$alkoxy)methyl, 2-($C_1$-$C_4$alkoxy) ethoxymethyl, 2-hydroxyethoxymethyl or benzyl substituents which are attached to a nitrogen atom of "Het" (see e.g. Examples 59, 64 and 66).

Many of the intermediates of the formula (II) are known compounds, at least in general terms, see e.g. WO 89/05581 or U.S. Pat. No. 4,952,232, and others can be prepared analogously either to the methods disclosed in these references, or to the techniques illustrated herein in the section headed "Preparations".

A typical method to certain key iodo-phenyl intermediates can for example be illustrated as follows:

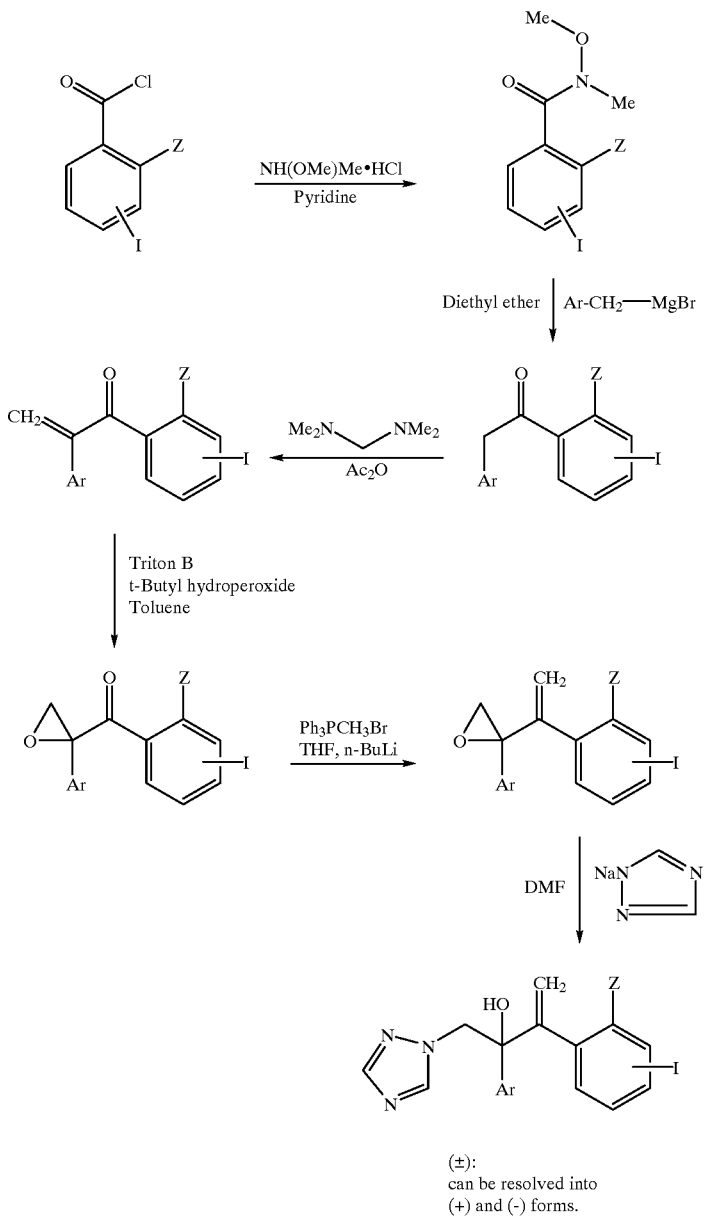

(±):
can be resolved into
(+) and (−) forms.

These iodo-phenyl intermediates can then be progressed into the intermediates (II) by several methods.

For compounds (II) in which "Het" is linked to the adjacent phenyl group by a nitrogen atom, the following route can be used:

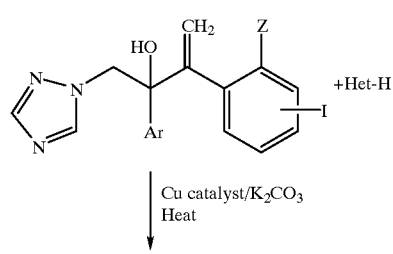

(IIA)

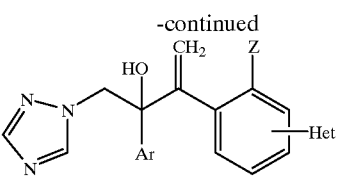

For compounds (II) in which "Het" is linked to the adjacent phenyl group by a carbon atom, the following route can be used. When "Het" is unsubstituted, it is preferred to protect "Het" with a protecting group Q, preferably a ($C_1$–$C_4$ alkoxy) methyl, [2-($C_1$–$C_4$ alkoxy)ethoxy]methyl, benzyl or trityl protecting group, preferably an ethoxymethyl, 2-methoxyethoxymethyl, benzyl or trityl group, which group can be subsequently removed by conventional techniques, e.g. by acid hydrolysis (alkoxymethyl, alkoxyethoxymethyl or trityl only) or catalytic hydrogenation, if required. [In fact, the end products (I) in which "Het" is substituted by $C_1$–$C_4$ alkoxymethyl, [2-($C_1$–$C_4$ alkoxy)ethoxy]methyl or benzyl are also active as antifungal agents in their own right]. A protecting group is not for example necessary when an N-alkyl heterocycle is required as shown in Preparation 53 where a final product having an N-methyl substituent is prepared. This route is conveniently illustrated by the use of 1,2,3-triazole, as follows:

is described in Examples 38, 42 and 63, although Q can be removed simultaneously with the reduction of the methylene group, if desired, as is for example described in Examples 59, 64 and 66.

Furthermore, Preparation 11 illustrates a route to intermediates (II) in which "Het" is a 1,2,3-triazol-4-yl group.

Routes to intermediates (II) in which X contains a pyridyl moiety are illustrated in Preparations 22 and 24. Preparation

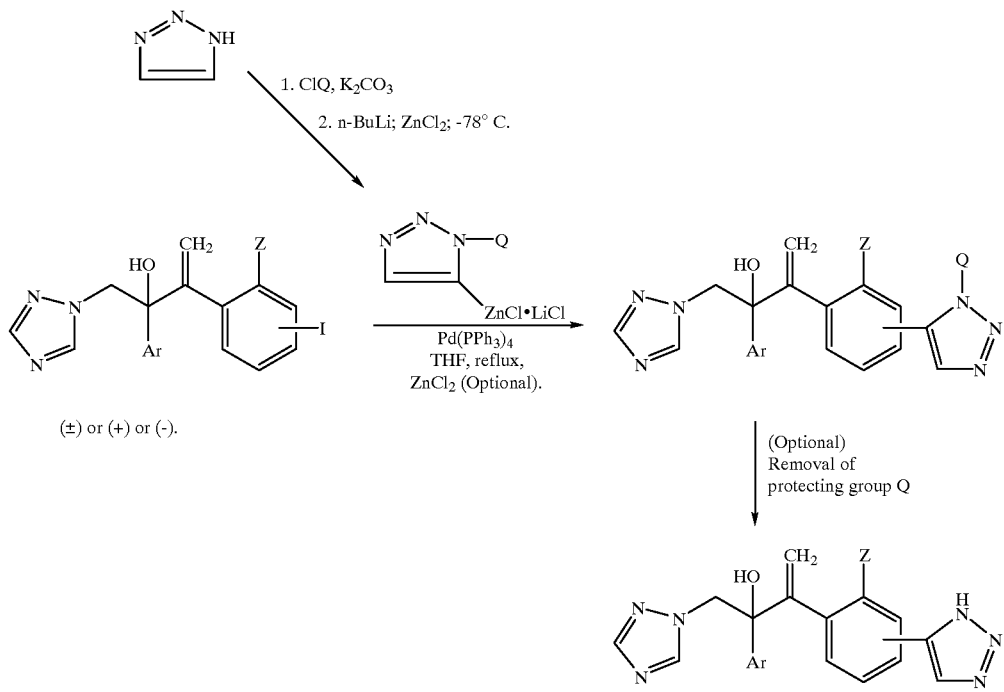

As stated above, Q is preferably ethoxymethyl, 2-methoxyethoxymethyl, benzyl or trityl, the first two of these groups being removable by acidic hydrolysis, e.g. using dilute aqueous hydrochloric acid (see e.g. Examples 38 and 42 which illustrate this technique), the benzyl group being removable by catalytic hydrogenation (see e.g. Example 63), and the trityl group by hydrolysis with trifluoroacetic acid. Where end products (I) in which "Het" is unsubstituted are desired, it is possible to remove the protecting group Q as the very last step of the whole reaction as 25 illustrates a route to intermediates (II) in which "Het" is a 5-amino-1,3,4-thiadiazol-2-yl group.

Preparation 21 illustrates an alternative to the preparation of intermediates (IIA) in which "Het" is N-linked to the adjacent phenyl group, and this can be illustrated in general terms as follows:

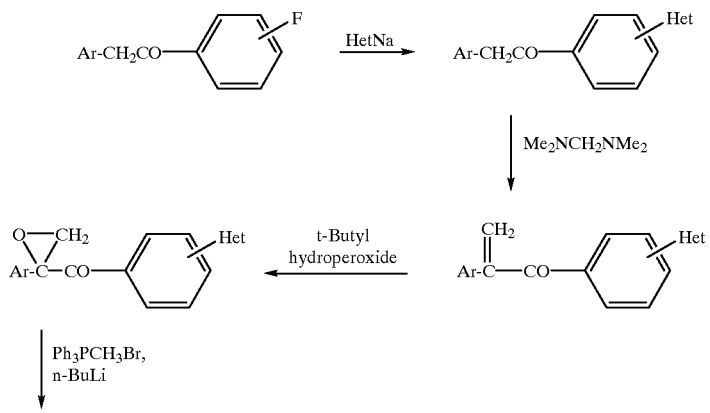

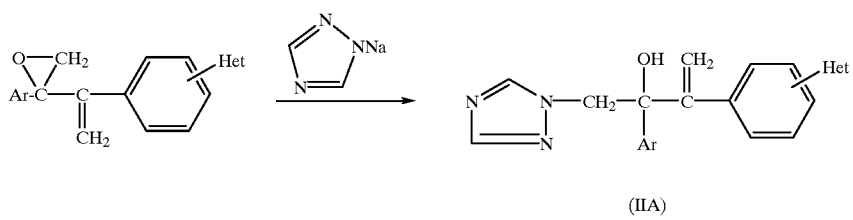

(IIA)

Route B

A phenylthio, benzyl, ($C_1$–$C_4$ alkoxy)methyl, 2-($C_1$–$C_4$ alkoxy)ethoxymethyl, or 2-hydroxyethoxymethyl substituent on "Het" can be removed, if desired, by catalytic hydrogenation similarly to the procedure of Route A, e.g. over palladium or Raney nickel at about 30 to 100 p.s.i. (200 to 666 kPa) and from room temperature up to 100° C. in a solvent such as methanol or ethanol.

Route C

Compounds of the formula (I) in which "Het" is a 1,2,4-triazol-4-yl group can be prepared from the corresponding formamido compounds (i.e. the corresponding compounds having a formamido group attached to the phenyl, pyridyl or pyrimidinyl group of X) by reaction with formylhydrazine, e.g. by reaction at high temperature (typically from 150–250° C. for about 1.5 hours) in the absence of a solvent or in the presence of an organic solvent such as DMF or N,N-dimethylacetamide at the reflux temperature of the solvent. The formamido starting materials are typically obtainable by the route illustrated in Preparation 19.

Route D

Compounds of the formula (I) in which "Het" is a 5-[$C_1$–$C_4$ alkyl]-1,3,4-oxadiazol-2-yl group can be prepared by the reaction of the corresponding hydrazinocarbonyl compounds (—CONHNH$_2$) with an imidate of the formula:

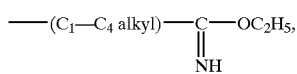

or with a salt thereof, preferably the hydrochloride (see e.g. Example 37). The reaction is typically carried out in an organic solvent such as ethanol or dioxan at a temperature of from room temperature up to the reflux temperature of the solvent. The reaction is preferably carried out under reflux. Preparation 23 illustrates a typical preparation of a hydrazinocarbonyl (benzoylhydrazide) starting material.

Route E

Certain N-protecting groups, e.g. ($C_1$–$C_4$ alkoxy)methyl (preferably ethoxymethyl), 2-($C_1$–$C_4$ alkoxy)ethoxymethyl (e.g. 2-methoxyethoxy-methyl) and 2-hydroxyethoxymethyl, when attached to a nitrogen atom of "Het", can also be removed by acidic hydrolysis, e.g. by hydrolysis using dilute hydrochloric acid under reflux in a solvent such as ethanol (see e.g. Examples 38 and 42). The N-protected compounds can be prepared as described in Route A.

Similarly a trityl protecting group can be removed by acid hydrolysis, preferably using trifluoroacetic acid (see e.g. Example 78).

Route F

Compounds (I) in which "Het" is substituted by a $C_1$–$C_4$ alkylthio group can be prepared by the alkylation of the corresponding mercapto-substituted compounds, typically by reaction firstly with a strong base and then with a compound of the formula $C_1$–$C_4$ alkyl.$Q^1$ where $Q^1$ is a suitable leaylng group. Preferred bases are sodium hydride and n-butyllithium. The preferred leaylng group is iodo. The reaction is typically carried out in an organic solvent, such as DMF, and at about room temperature. Whilst the starting thiols can generally be prepared according to Route A, Preparation 31 illustrates a specific route to compounds in which "Het" is 5-mercapto-1,3,4-oxadiazol-2-yl.

Route G

Compounds (I) in which "Het" is substituted by $C_1$–$C_4$ alkylsulphonyl or $C_1$–$C_4$ alkylsulphonyl can be prepared by the oxidation of the corresponding $C_1$–$C_4$ alkylthio compounds from Route F using, respectively, about one molar equivalent or an excess of a suitable oxidising agent, e.g. m-chloroperoxybenzoic acid. Typically the starting material in an organic solvent such as dichloromethane is cooled to about −70° C., and treated with the appropriate quantity of m-chloroperoxybenzoic acid e.g. in dichloromethane. The solution is then allowed to warm to room temperature and stirred until reaction is complete (e.g. for 24 hours).

Route H

Compounds (I) in which "Het" is an oxadiazolyl group of the formula:

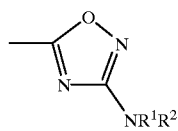

where $R^1$ and $R^2$ are each independently H or $C_1$–$C_4$ alkyl, can be prepared by the reaction of the corresponding ($C_1$–$C_4$ alkoxy)carbonyl-substituted (preferably methoxycarbonyl substituted compounds) with a hydroxy-guanidine of the formula:

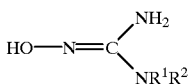

It is preferred to generate the hydroxyguanidine in situ from the corresponding acid salt (e.g. the hemisulphate) and a base (e.g. sodium ethoxide or hydride). The reaction is typically carried in an anhydrous organic solvent such as anhydrous ethanol and preferably in the presence of a dehydrating agent such as 3 Å or 4 Å molecular sieves. Reaction temperatures of from room temperature up to reflux can be used. Reflux is preferred. Preparation 23 illustrates the typical preparation of an alkoxycarbonyl starting material.

Route I

Compounds of the formula (I) in which "Het" is an oxadiazolyl group of the formula:

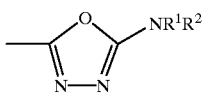

where $R^1$ and $R^2$ are each independently H or $C_1$–$C_4$ alkyl, can be prepared by the reaction of an "activated" ester of the corresponding carboxy-substituted compounds with a thiosemicarbazide of the formula:

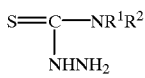

in a suitable organic solvent, e.g. dichloromethane or dimethylformamide. The "activated" (or "reactive") ester is typically formed in situ by reaction of the corresponding acid with an activating agent such as 1-hydroxybenzotriazole in the presence of a coupling agent such as 1-[3-dimethylaminopropyl]-3-ethylcarbodiimide. Preparation 32 illustrates the typical preparation of a carboxy-substituted starting material.

Route J

The compounds of the formula (I) can also be prepared by reacting a ketone of the formula:

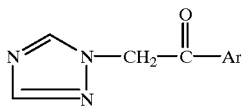

(III)

with a nucleophile of the formula:

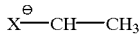

(IV)

or compound of the formula:

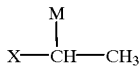

(IVA)

where X and Ar are as defined for formula (I) and M is Li, Zn-Hal or Mg-Hal. Hal, Cl, Br or I.

The nucleophile is typically prepared by reaction of the corresponding ethyl compound, X—CH$_2$—CH$_3$, with a strong base such as n-butyllithium, lithium diisopropylamide or lithium hexamethyl disilazide, in which case the counteron of (IV) is Li⊖

Alternatively (IVA) may be prepared by halogen-metal exchange, by treatment of a haloethyl compound

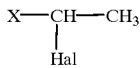

with an alkyllithium e.g. butyllithium or with a metal, e.g. zinc in the presence of iodine and optionally lead, or magnesium, in which case M is Li, Zn-Hal or Mg-Hal. (Hal=Cl, Br or I, preferably Br).

Route K

Compounds of the formula (I) in which "Het" is substituted by a group of the formula —NHCO($C_1$–$C_4$ alkyl) can be prepared by the acylation of the corresponding starting materials substituted by the group —NH$_2$ using an acid chloride or anhydride of the formula ($C_1$–$C_4$ alkyl) COCl or ($C_1$–$C_4$ alkyl.CO)$_2$O. Similarly, reaction of these starting materials with a $C_1$–$C_4$ alkanesulphonyl chloride results in compounds in which "Het" is substituted by a group of the formula —NHSO$_2$($C_1$–$C_4$ alkyl). Furthermore, reaction of these starting materials with a $C_1$–$C_4$ alkyl isocyanate yields compounds (I) in which "Het" is substituted by —NHCONH($C_1$–$C_4$ alkyl).

It is also possible to carry out these reactions at an earlier stage of the synthetic procedure on appropriate intermediates as is illustrated in Preparations 8 to 10.

Route L

When "Het" is 1,2,3-triazol-4-yl or 5-($C_1$–$C_4$ alkyl)-1,2,3-triazol-4-yl, then the end products (I) can be prepared as follows:

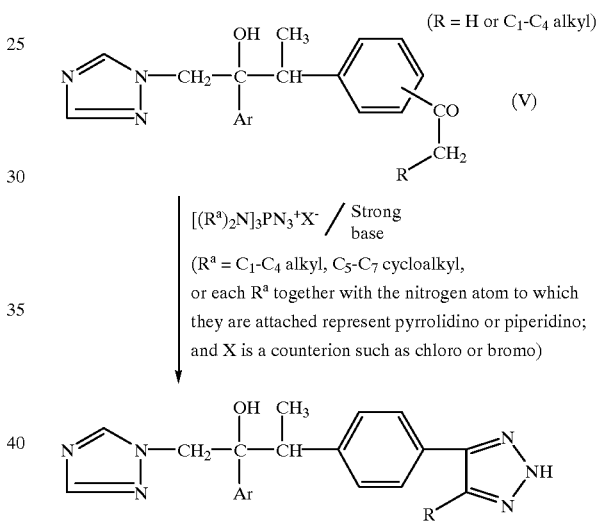

The reaction is typically carried out in ether as the solvent. It is preferred to use azidotris (diethylamino)phosphonium bromide, typically with potassium t-butoxide as the base.

The ketone starting materials can be prepared by conventional methods such as those illustrated in Preparations 47 and 48.

Route M

Compounds (I) in which "Het" is attached to the adjacent phenyl or heterocyclic ring by a carbon atom and is substituted on a nitrogen atom by $C_1$–$C_4$ alkyl, $C_1$–$C_4$ alkoxymethyl, cyano methyl or carbamoylmethyl can be prepared by the N-alkylation of the corresponding unsubstituted compounds, e.g. by using the appropriate $C_1$–$C_4$ alkyl halide or tosylate, ($C_1$–$C_4$ alkoxy)methyl halide, cyanomethyl halide or carbamoylmethyl halide (e.g. chloride, bromide or iodide), typically in the presence of an acid acceptor (e.g. potassium carbonate) and in a suitable organic solvent. When tautomerism of the ring is possible, alkylation may occur on one or more nitrogen atoms but the resulting mixture of end products can be separated by chromatography.

Route N

Compounds of the formula (I) in which X is

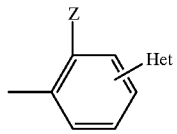

where "Het" is a 1 2,3-triazol-4-yl group and Z is H or F can also be prepared by the reaction of a compound of the formula:

(VI)

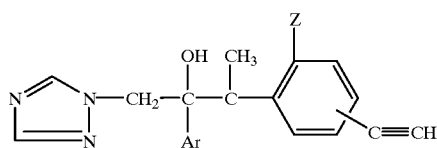

firstly with an azido ($C_1$–$C_4$ alkyl)silane (preferably azidotrimethylsilane) and then with water.

The starting materials (VI) can be prepared by the following scheme (analogous to that of Preparation II).

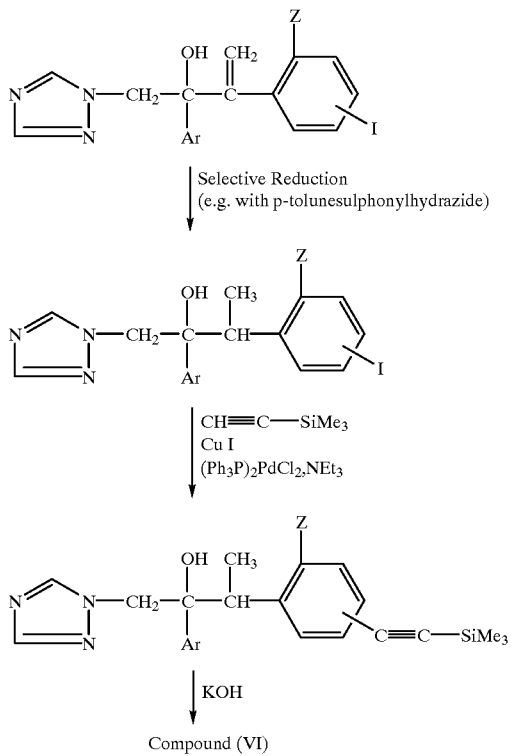

Route O

Compounds of the formula (I) in which "Het" is linked to the adjacent phenyl or pyridyl group by a nitrogen atom can also be prepared by the following reaction scheme:

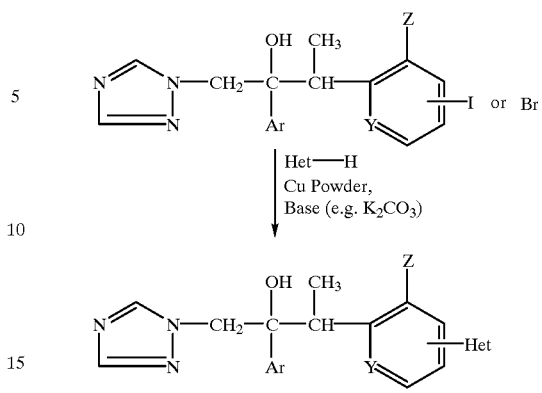

where "Het" is linked by a nitrogen atom the adjacent phenyl or pyridyl ring. Z is as defined for formula (I) and Y is CH or N.

The reaction is typically carried out with heating at up to 150° C. (and analogously to the method of Preparation 1). The starting materials can be prepared as described in Route A using diimide reduction. The preferred copper catalyst is copper bronze.

This route can also be used to prepare the compounds (I) in which "Het" is attached to a 3-pyridinyl or 4-pyrimidinyl group.

Route P

Compounds of the formula (I) in which "Het" is linked to the adjacent phenyl, pyridyl or pyrimidinyl group by a carbon atom can also be prepared by the Stille, Terashima, Suzuki or Negishi coupling reactions by reacting the corresponding compound in which the phenyl, pyridinyl or pyrimidinyl group is substituted by a leaylng group such as Cl, Br, I or —$OSO_2CF_3$ (—OTf) with a compound of the formula Het-M where M is —$Sn(Me)_3$, —$Sn(n-Bu)_3$, —$BEt_2$, —$B(OH)_2$ or —ZnCl, Het being as defined for formula (I), in the presence of a palladium or nickel catalyst, preferably tetrakis(triphenylphosphine)palladium (0). When the leaylng group is —OTf, lithium chloride is added to the reaction mixture. The reaction is best carried out by heating in a suitable organic solvent such as dioxane.

The point of attachment of "Het" is generally at the position adjacent to the substituted nitrogen atom.

It may be necessary to protect a nitrogen atom "Het" as is described in Route A.

The N-protecting group can then be removed conventionally.

Route Q

Compounds in which "Het" is halo-substituted can be prepared by conventional halogenation techniques, e.g. using N-chlorosuccinimide, N-bromosuccinimide, N-iodosuccinimide or "Selectfluor" [1-chloromethyl-4-fluoro-1,4-diazabicyclo[2.2.2]octane bis (tetrafluoroborate)—see J.Chem.Soc.Commun., 1992, 595].

Route R

Compounds in which "Het" is 3-mercapto-4-($C_1$–$C_4$ alkyl)-1,2,4-triazol-5-yl can be prepared by the cyclisation of the corresponding compound in which the phenyl, pyridinyl or pyrimidinyl ring is substituted by —CONHNHCSNH ($C_1$–$C_4$ alkyl) using, for example, sodium methoxide in ethanol, typically at reflux.

Route S

When "Het" is substituted by a mercapto group, then this can be removed, if desired, by treatment with hydrogen peroxide, typically in acetic acid under reflux.

Route T

A trimethylsilyl group on "Het" can be removed by treatment with aqueous potassium hydroxide, e.g. in ethanol, typically under reflux.

Pharmaceutically acceptable acid addition salts of the compounds (I) are either isolated directly from the reaction mixture or are prepared by mixing together solutions containing the free base and the desired acid. The salt generally precipitates from solution and is collected by filtration, or is recovered by evaporation of the solvent.

Similarly basic salts of compounds which form such salts can be prepared conventionally by reaction of a suitable compound (I) with, for example, sodium hydroxide.

The compounds of the formula (I) and their salts are antifungal agents, useful in the curative or prophylactic treatment of fungal infections in animals, including humans. For example, they are useful in treating superficial fungal infections in man caused by, among other organisms, species of *Candida. Trichophyton*, Microsdorum or Epidermophyton, or in mucosal infections caused by *Candida albicans* (e.g. thrush and vaginal candidiasis). They can also be used in the treatment of systemic fungal infections caused by, for example, species of *Candida* (e.g. *Candida albicans*), *Cryptococcus neoformans, Aspergillus flavus, Asperaillus fumigatus*, Coccidioides, Paracoccidioides, Histoplasma or Blastomyces.

The compounds of the present invention have been found to have unexpectedly good broad spectrum activity, including good activity against the clinically important Aspergillus spp. fungi.

The in vitro evaluation of the antifungal activity of the compounds can be performed by determining the minimum inhibitory concentration (m.i.c.), which is the concentration of the test compounds, in a suitable medium, at which growth of the particular micro-organism fails to occur. In practice, a series of agar plates, or liquid medium in microtiter plates, each having the test compound incorporated at a particular concentration, is inoculated with a standard culture of, for example, *Cryptococcus neoformans*, and each plate is then incubated for 48 hours at 37° C. The plates are then examined for the presence or absence of growth of the fungus and the appropriate m.i.c. value is noted. Other micro-organisms used in such tests can include *Candida Albicans, Aspergillus fumigatus*, Trichophyton spp., Microsporum spp., *Epidermophyton floccosum, Coccidioides immitis* and *Torulopsis glabrata*.

The in vivo evaluation of the compounds can be carried out at a series of dose levels by intraperitoneal or intravenous injection, or by oral administration, to mice or rats which are inoculated with, e.g. a strain of *Candida albicans, Aspergillus fumigatus* or *Cryptococcus neoformans*. Activity may be based on the number of survivors from a treated group of mice after the death of an untreated group of mice.

For Candida spp. infection models the dose level at which the compound provides 50% protection against the lethal effect of the infection ($PD_{50}$) is also assessed.

For Aspergillus spp. infection models the number of mice cured of the infection after a set dose allows further assessment of activity.

For Cryptococcus spp. infection models the number of colony forming units existing after a set dose is assessed and compared with control to determine compound efficacy. A preliminary assessment of potential liver toxicity may also be made on the basis of increase in liver weight relative to control.

For human use, the antifungal compounds of the formula (I) and their salts can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs, solutions or suspensions containing flavouring or colouring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

The solubility of a compound of the formula (I) in an aqueous medium may be improved by complexation with a hydroxyalkyl (see EP-A-0149197) or sulfoalkyl (see WO91/11172)) derivative of a cyclodextrin in the preparation of an appropriate pharmaceutical composition.

Preferably the cyclodextrin used is alpha-, beta-, or gamma-cyclodextrin and most preferably is beta-cyclodextrin. Preferably the derivative is a hydroxypropyl or tetrasulfobutyl derivative of a cyclodextrin, particularly beta-cyclodextrin.

For oral and parenteral administration to human patients, the daily dosage level of the antifungal compounds of the formula (I) and their salts will be from 0.01 to 20 mg/kg preferably 0.5 to 5 mg/kg, (in single or divided doses) when administered by either the oral or parenteral route. Thus tablets or capsules of the compounds will contain from 5 mg to 0.5 g of active compound for administration singly or two or more at a time, as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited, and such are within the scope of this invention.

Alternatively, the antifungal compounds of formula (I) can be administered in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin; or they can be incorporated, at a concentration between 1 to 10%, into an ointment consisting of a white wax or white soft paraffin base together with such stabilizers and preservatives as may be required.

Thus the invention further provides a pharmaceutical composition comprising a compound of the formula (I), or a pharmaceutically acceptable salt thereof, together with a pharmaceutically acceptable diluent or carrier.

The invention yet further provides a compound of the formula (I), or a pharmaceutically acceptable salt or composition thereof, for use as a medicament, in particular as an antifungal agent.

The invention also provides the use of a compound of the formula (I), or of a pharmaceutically acceptable salt or composition thereof, for the manufacture of an antifungal agent.

The invention yet further provides a method of treating an animal (including a human being) to cure or prevent a fungal infection, which comprises treating said animal with an effective amount of a compound of the formula (I), or with, as appropriate, a pharmaceutically acceptable salt or composition thereof.

The invention also provides any novel intermediates described herein, e.g. the compounds of the formula (V) and the compounds of the formula (II) in which "Het" is attached to the adjacent phenyl, pyridyl or pyrimidinyl group by a carbon atom.

The following Examples illustrate the preparation of the compounds of the formula (I).

EXAMPLE 1

(2R,3S/2S,3R)-2-(2,4-Difluorophenyl)-3-(4-[pyrazol-1-yl]phenyl)-1-(1,2,4-triazol-1-yl)butan-2-ol

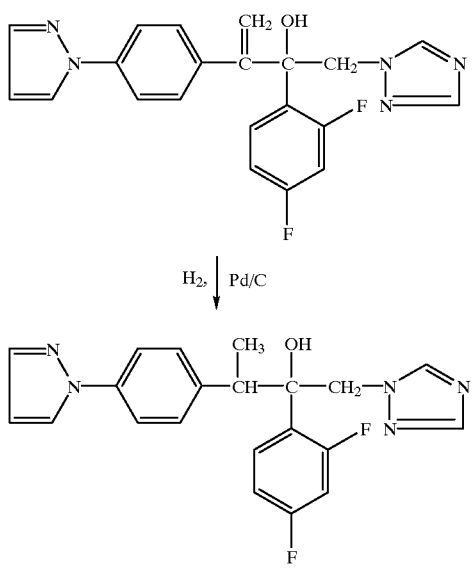

A solution of 2-(2,4-difluorophenyl)-3-(4-[pyrazol-1-yl]phenyl)-1-(1,2,4-triazol-1-yl)-3-buten-2-ol (0.8 g, 2 mmol-Preparation 3) in ethanol (100 ml) was hydrogenated at 30 psi (200 KPa) pressure over 10% palladium on charcoal (0.1 g) for 4 hours at room temperature. A further batch of catalyst (0.3 g) was added, and the hydrogenation was continued for 2 hours. The mixture was filtered through "Arbocel" (Trade Mark) and the filtrate was concentrated under reduced pressure. The residue was purified by flash chromatography on silica by elution with dichloromethanel-methanol (98:2). Fractions containing the desired product were combined and evaporated under pressure. The residue was crystallised from methanol to afford the title compound as a colouriess solid (280 mg, 34%), m.p. 176–177° C.

Analysis %: Found: C, 63.87; H, 4.73; N, 17.55. $C_{21}H_{19}F_2N_5O$ requires: C, 63.79; H, 4.84; N, 17.71.

EXAMPLE 2

(2R,3S/2S,3R) and (2R,3R/2S,3S)-2-(2,4-Difluorophenyl)-3-(4-[1-methylimidazol-2-yl]phenyl)-1-(1,2,4-triazol-1-yl)butan-2-ol

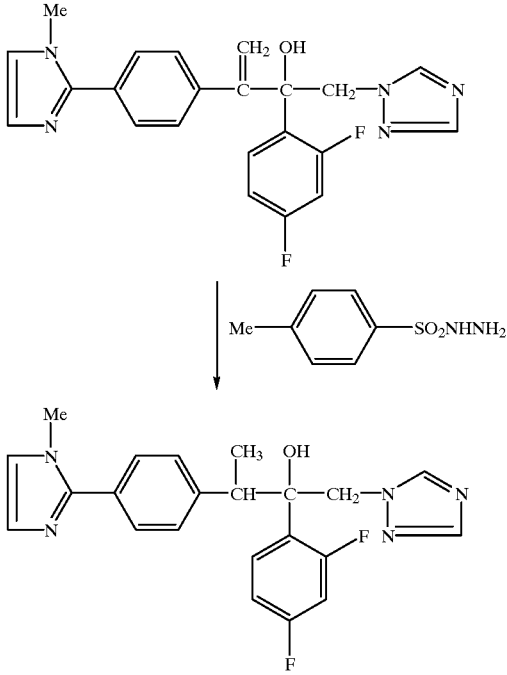

A mixture of 2-(2,4-difluorophenyl)-3-(4-[1-methylimidazol-2-yl]phenyl)-1-(1,2,4-triazol-1-yl)-3-buten-2-ol (0.45 g, 1.1 mmol-see Preparation 13) and p-toluenesulphonylhydrazide (1.0 g, 5.5 mmol) was suspended in toluene (20 ml) and heated under reflux for 4 hours. The cooled mixture was diluted with ethyl acetate (50 ml) then washed twice with aqueous sodium hydroxide solution (2N, 50 ml). The organic phase was dried ($MgSO_4$), filtered and evaporated under reduced pressure to give a yellow oil. The crude product was purified by chromatography on silica by elution with ethyl acetate/methanol (97:3). The pure fractions were combined and evaporated to give a colourless foam. The foam was triturated with hexane/ether to afford the title compound, (2R,3R/2S,3S) enantiomeric pair, as a colourless solid (0.07 g 15%), m.p. 159–161° C.

Analysis %: Found: C, 64.39; H, 5.01; N, 16.97. $C_{22}H_{21}F_2N_5O$ requires: C, 64.53; H, 5.17; N, 17.11%.

$^1$H-N.M.R. (300 MHz, $CDCl_3$): δ=1.60 (d,3H), 3.42 (q,1H), 3.65 (s,3H), 4.63 (d,1H), 4.78 (s,1H), 5.01 (d,1H), 6.43 (m,1H), 6.61 (m,1H), 6.91 (s,1H), 6.94 (m,1H), 7.04 (s,1H), 7.06(d,2H), 7.38(d,2H), 7.78(s,1H), 7.94(s,1H) ppm.

Further elution with ethyl acetate/methanol (95:5) proylded, after combination and evaporation of the appropriate fractions, a colourless foam. Trituration with hexane/ethyl acetate afforded the title compound, (2R,3S/2S,3R) enantiomeric pair, as a colourless solid (0.1 g, 22%), m.p. 153–155° C.

Analysis %: Found: C, 64.50; H, 5.19; N, 16.92. $C_{22}H_{21}F_2N_5O$ requires: C, 64.53; H, 5.17; N, 17.11%.

$^1$H-N.M.R. (300 MHz, $CDCl_3$): δ=1.14 (d,3H), 3.38 (q,1H), 3.79 (s,3H), 3.86 (d,1H), 4.80 (d,1H), 4.81 (s,1H), 6.75 (m,2H), 6.98 (s,1H), 7.10 (s,1H), 7.46 (m,1H), 7.58 (d,2H), 7.61 (d,2H), 7.70 (s,1H), 7.74 (s,1H) ppm.

EXAMPLES 3 to 30

The following compounds were prepared using the method of either Example 1 or Example 2, as specified in the Table.

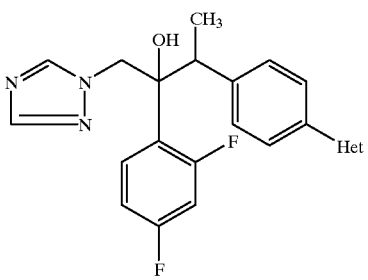

It will be noted that in some Examples using the method of Example 2, only the predominant diastereomeric pair was isolated.

| Ex. No. | Het | Stereo-chemistry | m.p. (° C.) | Analysis % (Theoretical in brackets) | | | Molecular formula | Method of Example No. |
|---|---|---|---|---|---|---|---|---|
| | | | | C | H | N | | |
| 3 | | (2R,3S/2S,3R) | 204–205 | 63.79 (63.79 | 4.64 4.84 | 17.30 17.71) | $C_{21}H_{19}F_2N_5O$ | 1 |
| 4 | | (2R,3S/2S,3R) | 167–168 | 60.63 (60.60 | 4.55 4.58 | 21.57 21.20) | $C_{20}H_{18}F_2N_6O$ | 1 |
| 5 | | (2R,3S/2S,3R) | 194–195 | 60.80 (60.60 | 4.44 4.58 | 21.02 21.20) | $C_{20}H_{18}F_2N_6O$ | 1 |
| 6 | | (2R,3S/2S,3R) | 229–232 | 60.77 (60.60 | 4.54 4.58 | 21.13 21.20) | $C_{21}H_{20}F_2N_6O$ | 1 |
| 7 | | (2R,3S/2S,3R) | 202 | 61.62 (61.45 | 5.09 4.91 | 20.37 20.48) | $C_{21}H_{20}F_2N_6O$ | 1 |
| 8 | | (2R,3S/2S,3R) | 197 | 64.61 (64.54 | 5.08 5.17 | 17.14 17.10) | $C_{22}H_{21}F_2N_5O$ | 1 |
| 9 | | (2R,3S/2S,3R) | 153–155 | 60.93 (60.78 | 5.21 5.32 | 18.78 18.50) | $C_{23}H_{24}F_2N_6O_2$ | 2 |
| 10 | | (2R,3R/2S,3S) | Gum | 60.31 (60.47 | 5.36 5.35 | 18.21 18.40) | $C_{23}H_{24}F_2N_6O_2 \cdot \frac{1}{8}H_2O$ | 2 |

-continued

| Ex. No. | Het | Stereo-chemistry | m.p. (° C.) | Analysis % (Theoretical in brackets) | | | Molecular formula | Method of Example No. |
|---|---|---|---|---|---|---|---|---|
| | | | | C | H | N | | |
| 11 | [5-methyl-3-(methylthio)-1-(ethoxymethyl)-1,2,4-triazole] | (2R,3R/2S,3S) | Foam | 57.57 (57.70 | 5.31 5.04 | 16.55 16.83) | $C_{24}H_{26}F_2N_6O_2S$ | 2 |
| 12 | [5-methyl-3-(methylthio)-1-(ethoxymethyl)-1,2,4-triazole] | (2R,3S/2S,3R) | Foam | Characterized by $^1$H-N.M.R. spectroscopy (see later) | | | $C_{24}H_{26}F_2N_6O_2S$ | 2 |
| 13 | [4-methyl-1-(ethoxymethyl)pyrazole] | (2R,3S/2S,3R) | 80 | 62.52 (62.32 | 5.54 5.66 | 14.79 15.14) | $C_{24}H_{25}F_2N_5O_2 \cdot \frac{1}{2}H_2O$ | 2 |
| 14 | [5-methyl-2-(phenylthio)-1-(ethoxymethyl)imidazole] | (2R,3S/2S,3R) (2R,3R/2S,3S) | Foam Foam | 63.27 (63.14 Characterised by $^1$HN.M.R (see later) | 4.91 5.29 | 12.56 12.27) | $C_{30}H_{29}F_2N_5O_2S \cdot \frac{1}{2}H_2O$ $C_{30}H_{29}F_2N_5O_2S$ | 2 |
| 15‡ | [4-methyl-1H-1,2,3-triazole] ‡ | (2R,3S/2S,3R) (2R,3R/2S,3S) | 115–118 Foam | 60.00 (59.92 59.90 (59.92 | 4.65 4.65 4.56 4.65 | 20.77 20.96) 20.54 20.96) | $C_{20}H_{18}F_2N_6O \cdot \frac{1}{4}H_2O$ $C_{20}H_{18}F_2N_6O \cdot \frac{1}{4}H_2O$ | 1 (and 2) 2 |
| 16 | [1-methyl-3-(NHSO$_2$CH$_3$)pyrazole] | (2R,3S/2S,3R) | 102 | 53.08 (53.10 | 4.40 4.45 | 16.63 16.89) | $C_{22}H_{22}F_2H_6O_3S \cdot \frac{1}{2}H_2O$ | 1 |
| 17 | [1-methyl-3-(NHCONHCH$_3$)pyrazole] | (2R,3S/2S,3R) | 194–196 | 59.10 (59.09 | 4.93 4.96 | 20.80 20.97) | $C_{23}H_{23}F_2N_7O_2$ | 1 |
| 18 | [1-methyl-3-(NHCOCH$_3$)pyrazole] | (2R,3S/2S,3R) | 222 | 61.33 (61.06 | 4.72 4.90 | 18.42 18.57) | $C_{23}H_{22}F_2N_6O_2$ | 1 |
| 19 | [2-methyl-1-(ethoxymethyl)imidazole] | (2R,3S/2S,3R) (2R,3R/2S,3S) | 132–135 Foam | Characterized by $^1$H-N.M.R. (see later) Characterised by $^1$H-N.M.R. (see later) | | | $C_{24}H_{25}F_2N_5O_2$ $C_{24}H_{25}F_2N_5O_2$ | 2 |
| 20 | [5-methyl-2-amino-1,3,4-thiadiazole] | (2R,3S/2S,3R) | 258–262 | 55.22 (55.47 | 4.01 4.31 | 19.14 19.42) | $C_{20}H_{18}F_2N_6OS \cdot \frac{1}{4}H_2O$ | 2 |
| 21 | [5-methyl-2-amino-1,3,4-thiadiazole] | (2R,3R/2S,3S) | 129–131 | 55.38 (55.47 | 3.92 4.31 | 19.21 19.42) | $C_{20}H_{18}F_2N_6OS \cdot \frac{1}{4}H_2O$ | 2 |

-continued

| Ex. No. | Het | Stereo-chemistry | m.p. (°C.) | Analysis % (Theoretical in brackets) C | H | N | Molecular formula | Method of Example No. |
|---|---|---|---|---|---|---|---|---|
| 22 | 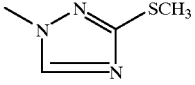 | (2R,3S/2S,3R) | Foam | Characterised by $^1$H-N.M.R. (see later) | | | $C_{21}H_{20}F_2N_6OS$ | 2 |
| 23 | 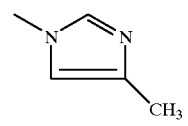 | (2R,3S/2S,3R) | 117–120 | 64.99 (64.54 | 5.39 5.17 | 16.55 17.10) | $C_{22}H_{21}F_2N_5O$ | 1 |
| 24 | 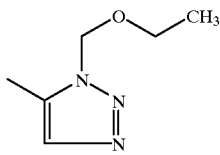 | (2R,3S/2S,3R) | 138–140 | 61.14 (60.78 | 5.44 5.32 | 18.20 18.49) | $C_{23}H_{24}F_2N_6O_2$ | 1 |
| 25 | 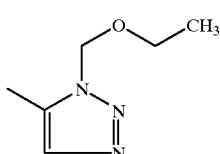 | (2R,3S) | Foam | Characterised by $^1$H-N.M.R. (see later) | | | $C_{23}H_{24}F_2N_6O_2$ | 1 |
| 26 | 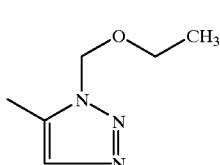 | (2S,3R) | Foam | 60.70 (60.78 | 5.38 5.32 | 18.58 18.50) | $C_{23}H_{24}F_2N_6O_2$, $[\alpha]_D^{25} = +49°$ | 1 |
| 27 | 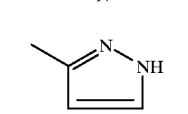 | (2R,3R/2S,3S) (2R,3S/2S,3R) | Foam Foam | 63.61 (63.82 63.28 (63.07 | 4.88 5.11 4.91 4.92 | 16.87 17.17) 17.04 17.50) | $C_{21}H_{19}F_2N_5O$. ⅙$Et_2O$ $C_{21}H_{19}F_2N_6O$. ¼$H_2O$ | 2 |
| 28 | 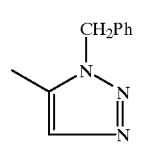 | (2R,3S/2S,3R) (2R,3S) | Foam Oil | 66.66 (66.46 Characterised by $^1$HNMR (see later) | 4.97 5.07 | 17.27 17.01) | $C_{27}H_{24}F_2N_6O$ $C_{27}H_{24}F_2N_6O$ | 1 |
| 29 | CH$_2$O(CH$_2$)$_2$OH 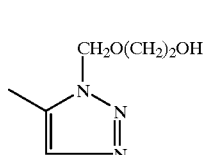 | (2R,3S/2S,3R) | Foam | 58.22 (57.91 | 5.23 5.30 | 17.05 17.69) | $C_{23}H_{24}F_2N_6O_3$. ¼$H_2O$ | 1 |
| 30 | CH$_2$O(CH$_2$)$_2$OCH$_3$ 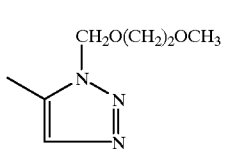 | (2R,3S/2S,3R) | 122–123° | 59.92 (59.50) | 5.46 5.41 | 17.57 17.35) | $C_{24}H_{26}F_2N_6O_3$, | 1 |

‡The RS/SR isomer of Example 15 was obtained by the method of Example 1. The Example was then repeated by the method of Example 2, when good separation of the diastereomers was obtained by hplc on an "ODS2" column by elution with methanol/water (60:40) when the RR/SS isomer eluted first.

$^1$H-N.M.R. (300 MHz, CDCl$_3$):

Example No. 12: δ=1.14 (d,3H), 1.24 (t,3H), 2.62 (s,2H), 3.38 (q,1H), 3.80 (q,2H), 3.82 (d,1H), 4.80 (d,1H),4.82 (s,1H),5.42 (s,2H), 6.7–6.8 (m,2H), 7.46 (q,1H), 7.63 (d,2H), 7.70 (s,1H), 7.72 (s,1H), 7.78 (d,1H), 7.89 (d,2H) ppm.

Example No. 14: δ=1.14 (t,3H), 1.57 (d,3H), 3.38 (q,2H), 3.41 (q,1H), 4.63 (d,1H), 4.82 (s,1H), 5.26 (ABq,2H), 6.43 (m,1H), 6.61 (m,1H), 6.96 (m,1H), 7.08 (d,2H), 7.24 (s,5H), 7.26 (d,2H), 7.3–7.7 (m,2H), 7.76 (s,1H), 7.87 (s,1H) ppm.

Example No. 19 (2R,3S/2S,3R): δ=1.17 (d,3H), 1.22 (t,3H), 3.39 (q,1H), 3.59 (q,2H), 3.86 (d,1H), 4.77 (s,1H), 4.80 (d,1H), 5.33 (s,2H), 6.78 (m,2H), 7.16 (d,2H), 7.50 (m,1H), 7.74 (s,1H), 7.76 (s,1H), 7.80 (d,2H) ppm.

Example No. 19 (2R,3/R2S,3S): δ=1.19 (t,3H), 1.60 (d,3H), 3.46 (q,3H), 4.65 (d,1H), 4.77 (s, 1H), 5.12 (d, 1H), 5.20 (s,1H), 6.44 (td,1H), 6.62 (td,1H), 6.94 (q,1H), 7.06 (d, 2H), 7.08 (d,2H), 7.50 (d,2H), 7.76 (s,1H), 7.85 (s,1H) ppm.

Example No. 22: δ=1.14 (d,3H), 2.64 (s,3H), 3.38 (q,1H), 3.84 (d,1H), 4.80 (d,1H), 4.87 (s,1H), 6.79 (m,2H), 7.48 (m,1H), 7.63 (s,4H), 7.74 (s,1H), 7.76 (s,1H), 8.44 (s,1H) ppm.

Example No. 25: δ=1.15 (d,3H), 1.22 (t,3H), 3.40 (q,1H), 3.75 (q,2H), 3.90 (d,1H), 4.85 (d,2H), 5.70 (s,2H), 6.75 (m,2H), 7.50 (m,1H), 7.67 (s,4H), 7.75 (s,1H), 7.82 (s,1H), 7.90 (s,1H) ppm.

Example No. 28: δ=1.13 (d,3H), 3.34 (q,1H), 3.80 (d,1H), 4.76 (d,1H), 4.80 (s,1H), 5.59 (s,2H), 6.7–6.8 (m, 2H), 7.05 (m, 2H), 7.20 (m,5H), 7.46 (m,1H), 7.5 (d,2H), 7.70 (s,1H), 7.72 (s,1H), 7.74 (s,1H) ppm.

EXAMPLES 31–34

The following compounds were prepared using a similar method to that described in Example 2.

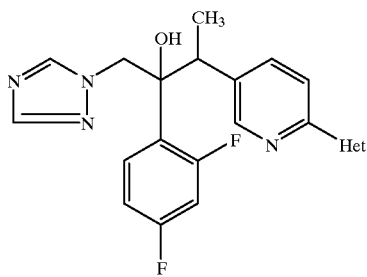

EXAMPLE 34

$^1$H-N.M.R. (300 MHZ, CDCl$_3$): δ=1.64 (d,3H), 3.50 (q,1H), 3.71 (d,1H), 5.03 (d,1H), 5.05 (s,1H), 6.48 (m,1H), 6.67 (m,1H), 6.92 (q,1H), 7.68 (m,2H), 7.80 (s,1H), 7.85 (s,1H), 8.00 (s,1H), 8.05 (s,1H), 9.05 (s,1H) ppm.

EXAMPLE 35

(2R ,3S/2S,3R)-2-(2,4-Difluorophenyl)-3-(4-[1-ethoxymethylimidazol-5-yl]phenyl)-1-(1,2,4-triazol-1-yl)butan-2-ol

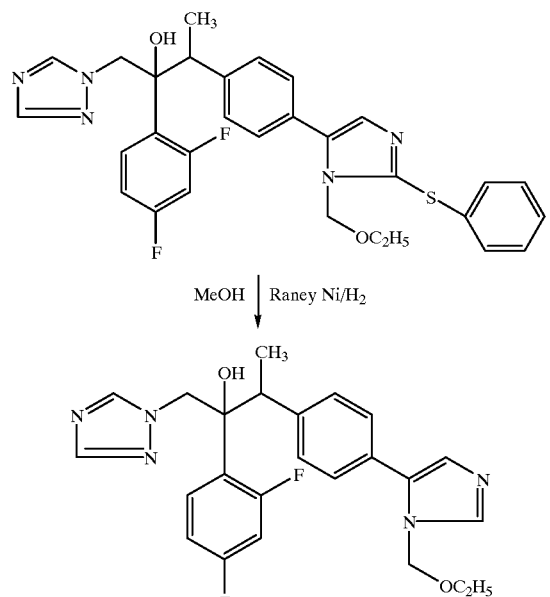

A solution of (2R,3S/2S,3R)-2-(2,4-difluorophenyl)-3-(4-[1-ethoxymethyl-2-phenylthioimidazol-5-yl]phenyl)-1-(1,2,4-triazol-1-yl)butan-2-ol (0.44 g, 0.8 mmol-see Example 14) in methanol (30 ml) was hydrogenated under a pressure of 30 psi (200 KPa) over Raney nickel (0.07 g) at room

| Ex. No. | Het | Stereo-chemistry | m.p. (° C.) | Analysis % (Theoretical in brackets) | | | Molecular formula |
|---|---|---|---|---|---|---|---|
| | | | | C | H | N | |
| 31 | (imidazole) | (2R,3S/2S,3R) | 169–171 | 60.67 (60.60 | 4.49 4.58 | 20.89 21.20) | C$_{20}$H$_{18}$F$_2$N$_6$O |
| 32 | (imidazole) | (2R,3R/2S,3S) | 86° | 60.41 (60.96 | 5.16 5.35 | 19.58 19.39) | C$_{20}$H$_{18}$F$_2$N$_6$O.½(C$_2$H$_5$)$_2$O |
| 33 | (triazole) | (2R,3S/2S,3R) | 202–203 | 57.80 (57.43 | 4.38 4.31 | 24.90 24.67) | C$_{19}$H$_{17}$F$_2$N$_7$O |
| 34 | (triazole) | (2R,3R/2S,3S) | 88–92 | Characterised by $^1$H-N.M.R. spectroscopy (see below) | | | C$_{19}$H$_{17}$F$_2$N$_7$O | temperature for 4 hours. The catalyst was removed by filtration through "Arbocel" (Trade Mark) and the filtrate was evaporated under reduced pressure. The residue was partitioned between dichloromethane (50 ml) and water (20 ml). The separated organic phase was dried (MgSO$_4$) and evaporated under reduced pressure. The crude product was purified by column chromatography on silica by elution with dichloromethane/methanol (95:5). Fractions containing the desired product were combined and evaporated under reduced pressure to give the title compound (0.17 g, 50%) as a foam, which was characterised by $^1$H-N.M.R. spectroscopy (300 MHz, CDCl$_3$) δ=1.14 (d,3H), 1.22 (t,3H), 3.36 (q,1H), 3.55 (q,2H), 3.89 (d,1H), 4.80 (s,1H), 4.82 (d,1H), 5.29 (s,2H), 6.78 (m,2H), 7.19 (s,1H), 7.50 (m,1H), 7.59 (s,4H), 7.70 (s,1H), 7.76 (s,1H), 7.77 (s,1H) ppm.

EXAMPLE 36

(2R,3S/2S,3R)-2-(2,4-Difluorophenyl)-3-[4-(1,2,4-triazol-4-yl)phenyl]-1-(1,2,4-triazol-1-yl)butan-2-ol

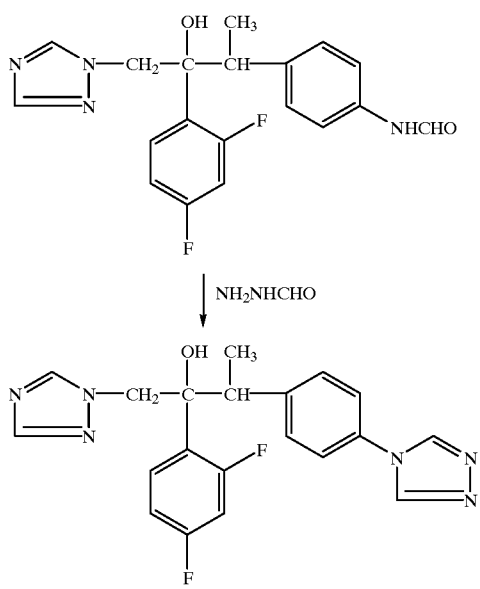

An intimate mixture of 2-(2,4-difluorophenyl)-3-(4-formamidophenyl)-1-(1,2,4-triazol-1-yl)butan-2-ol (4.4 g, 12 mmol-see Preparation 19) and formylhydrazine (7.0 g, 0.13 mmol) was heated to 240° C. for 1.5 hours. The cooled mixture was partitioned between dichloromethane (100 ml) and water (100 ml). The aqueous phase was extracted with dichloromethane (100 ml) and the organic extracts were combined, dried (MgSO$_4$) and evaporated under reduced pressure. The residue was purified by flash chromatography by gradient elution with dichloromethane/methanol [98:2→96:4→95:5→90:10]. Fractions containing the desired product were combined and evaporated under reduced pressure. The crude product was triturated with ether to give the title compound (2.1 g, 44%) as a white solid, m.p. 238–240° C.

Analysis %: Found: C, 60.60; H, 4.52; N, 20.91; C$_{20}$H$_{18}$F$_2$N$_6$O requires: C, 60.59; H, 4.58; N, 21.21.

The title compound was resolved by chiral hplc using a Chiralpak AD (Trademark) column by elution with isopropanol/hexane (30:70). Fractions containing each single enantiomer were combined and evaporated under reduced pressure. The front-running enantiomer was the 2S,3R form.

EXAMPLE 37

(2R,3S/2S,3R)-2-(2,4-Difluorophenyl)-3-[4-(5-methyl-1,3,4-oxadiazol-2-yl)phenyl-1-(1,2,4-triazol-1-yl)butan-2-ol

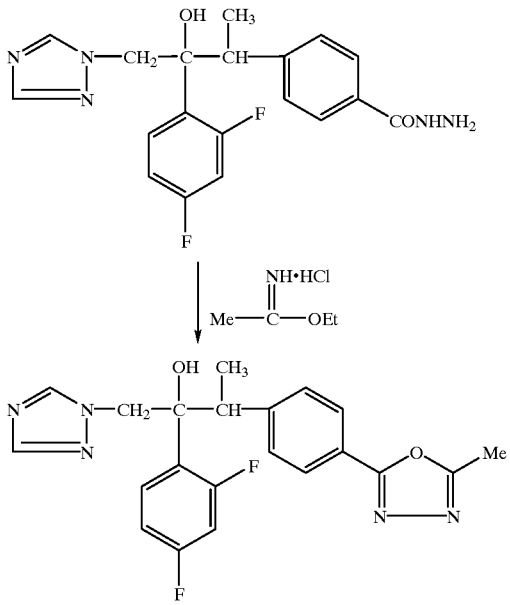

A suspension of (2R,3S/2S,3R)-4-[2-(2,4-difluorophenyl)-2-hydroxy-1-(1,2,4triazol-1-yl)-but-3-yl]benzoyl hydrazide (0.3 g, 0.8 mmol-see Preparation 23) and ethyl acetimidate hydrochloride (0.24 g, 2 mmol) in ethanol (5 ml) was heated under reflux for 3 hours. The cooled mixture was filtered, and the filtrate evaporated under reduced pressure. The residue was dissolved in dioxan (10 ml) and then heated under reflux for 18 hours. The mixture was evaporated under reduced pressure then partitioned between dichloromethane (20 ml) and water (20 ml). The organic layer was dried (MgSO$_4$) and evaporated under reduced pressure to give the title compound (0.18 g, 62%) as a colourless solid, m.p. 182–184° C.

Analysis %: Found: C, 61.44; H, 4.56; N, 16.92; C$_{21}$H$_{19}$F$_2$N$_5$O$_2$ requires: C, 61.30; H, 4.66; N, 17.03.

EXAMPLE 38

2R,3S/2S,3R)-2-(2,4-Difluorophenyl-3-(4-[1,2,4-triazol-3-yl]phenyl)-1-(1,2,4-triazol-1-yl)butan-2-ol hydrochloride hydrate

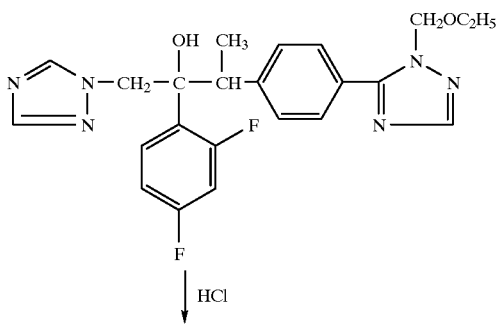

29

-continued

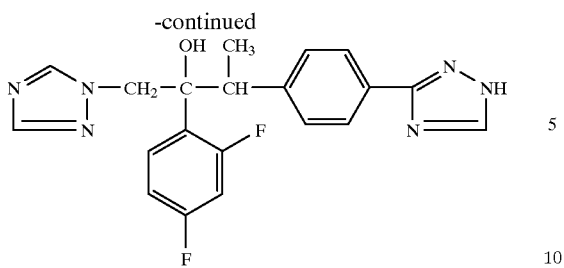

A solution of (2R,3S/2S,3R)-2-(2,4-difluorophenyl)-3-(4-[1-ethoxymethyl-1,2,4-triazol-5-yl]phenyl)butan-2-ol (0.12 g, 0.3 mmol-see Example 9) in ethanol (1 ml) was treated with dilute hydrochloric acid (5M, 0.7 ml) and the mixture was then heated under reflux for 3 hours. The mixture was evaporated under reduced pressure and the residue was azeotroped with toluene (5 ml). The residual foam was triturated with ethanol/ethyl acetate to give the title compound (0.09 g, 76%) as a colourless solid, m.p. 197–203° C.

Analysis %: Found: C, 53.42; H, 4.30; N, 18,42. $C_{20}H_{18}F_2N_6O.HCl.H_2O$ requires: C, 53.40; H, 4.48; N, 18.68.

EXAMPLES 39–41

The following compounds were prepared from the corresponding N-ethoxymethyl compounds using the method of Example 38.

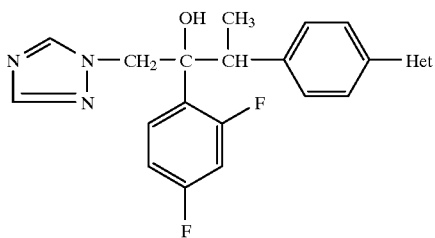

30

EXAMPLE 42

(2R,3S)-2-(2,4-Difluorophenyl)-3-(4-[1,2,3-triazol-4-yl]phenyl)-1-(1,2,4-triazol-1-yl)butan-2-ol

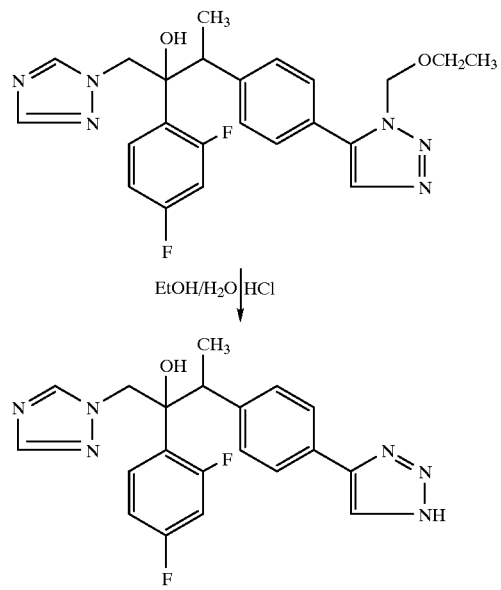

A solution of (2R,3S)-2-(2,4-difluorophenyl)-3-(4-[1-ethoxymethyl-1,2,3-triazol-5-yl]phenyl)-1-(1,2,4-triazol-1-yl)butan-2-ol (5.2 g, 0.11 mol-see Example 25) in ethanol (50 ml) was treated with dilute hydrochloric acid (2N, 12 ml) and the mixture was heated under reflux for one hour. The mixture was cooled to room temperature and the solvent was removed under reduced pressure. The residue was dissolved in water (50 ml) and the mixture was neutralized by addition of solid sodium carbonate and was extracted with ethyl acetate (2×100 ml). The combined extracts were dried ($MgSO_4$) and evaporated under reduced pressure to yield a colourless foam. The crude product was purified by column chromatography on silica by elution with ethyl

| Ex. No. | Het | Stereo- chemistry | m.p. (° C.) | Analysis % (Theoretical in brackets) | | | Molecular formula |
|---|---|---|---|---|---|---|---|
| | | | | C | H | N | |
| 39 | ![pyrazole with methyl and NH] | (2R,3S/ 2S,3R) | 193–199 | 59.12 (58.39 | 4.52 4.67 | 16.31 16.21) | $C_{21}H_{19}F_2N_5O.HCl$ |
| 40 | ![imidazole with methyl] | (2R,3S/ 2S,3R) | 258–261 | 57.21 (57.20 | 4.49 4.80 | 15.66 15.88) | $C_{21}H_{19}F_2N_6O.HCl.0.5H_2O$ |
| 41 | ![triazole with methyl and SO2CH3] | (2R,3S/ 2S,3R) | — | 49.35 (49.36 | 4.22 4.38 | 16.49 16.45) | $C_{21}H_{20}F_2N_6O_3S.HCl$ | acetate/diethylamine (95:5) followed by ethyl acetate/methanol (90:10 then 80:20). Fractions containing the desired product were combined and evaporated under reduced pressure to yield the title compound as a colourless foam (3.7 g, 82%), $[\alpha]_D^{25}=-63.8°$.

Analysis %: Found: C, 60.39; H, 4.64; N, 21.00; $C_{20}H_{18}F_2N_6O$ requires: C, 60.59; H, 4.58; N, 21.21.

EXAMPLES 43–45

The following compounds were prepared from the corresponding N-ethoxymethyl compounds using the method of Example 42.

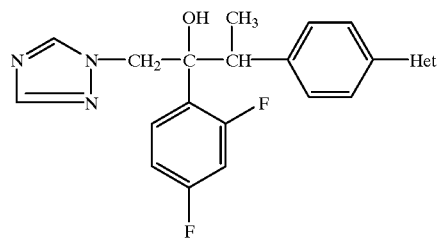

| Ex. No. | Het | Stereo-chemistry | m.p. (° C.) | Analysis % (Theoretical in brackets) | | | Molecular formula |
|---|---|---|---|---|---|---|---|
| | | | | C | H | N | |
| 43 | (imidazole) | (2R,3S/ 2S,3R) | 205–211 | 62.18 (62.36 | 4.82 4.98 | 16.88 17.31) | $C_{21}H_{19}F_2N_5O.0.5H_2O$ |
| 44 | (triazole) | (2R,3S/ 2S,3R) | 110–118 | 60.25 (60.59 | 4.59 4.58 | 21.41 21.21) | $C_{20}H_{18}F_2N_6O$ |
| 45 | (triazole) | (2S,3R) | Foam | 60.28 (60.59 | 4.69 4.58 | 20.99 21.21) | $C_{20}H_{18}F_2N_6O$ $[\alpha]_D^{25} = +46°$ |

EXAMPLES 46–50

The following compounds were prepared using the method of either Example 1 or Example 42, as specified in the Table.

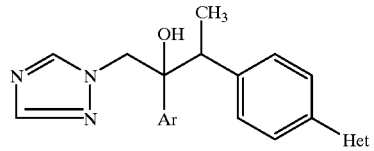

| Ex. No. | Het | Ar | Stereo-chemistry | m.p. (°C.) | Analysis % (Theoretical in brackets) C | H | N | Molecular formula | Method of Example No. |
|---|---|---|---|---|---|---|---|---|---|
| 46 | 1-methylimidazol-2-yl | 2-chlorophenyl | (2R,3S/ 2S,3R) | Foam | 61.02 (61.23 | 5.28 5.34 | 17.47 17.01) | $C_{21}H_{20}ClN_5O \cdot H_2O$ | 1 |
| 47 | 5-methyl-1-(ethoxymethyl)-1,2,3-triazol-4-yl | 2-chlorophenyl | (2R,3S/ 2S,3R) | 190–191 | Characterised by $^1$H-N.M.R. (see later) | | | $C_{23}H_{25}ClN_6O_2$ | 1 |
| 48 | 5-methyl-1H-1,2,3-triazol-4-yl | 2-chlorophenyl | (2R,3S/ 2S,3R) | 130–135 | 59.99 (59.48 | 5.19 4.96 | 20.31 20.81) | $C_{20}H_{19}ClN_6O \cdot 0.5H_2O$ | 42 |
| 49 | 5-methyl-1-(ethoxymethyl)-1,2,3-triazol-4-yl | 2-fluorophenyl | (2R,3S/ 2S,3R) | 122–124 | 63.18 (63.30 | 5.81 5.74 | 19.44 19.27) | $C_{23}H_{25}FN_6O_2$ | 1 |
| 50 | 5-methyl-1H-1,2,3-triazol-4-yl | 2-fluorophenyl | (2R,3S/ 2S,3R) | 164–166 | 63.18 (63.49 | 5.11 5.03 | 22.62 22.23) | $C_{20}H_{19}FN_6O$ | 42 |

EXAMPLE 51

(2R,3S/2S,3R)-2-(2,4-Difluorophenyl)-3-(4-[5-methylthio-1,3,4-oxadiazol-2-yl]phenyl)-1-(1,2,4-triazol-1-yl)butan-2-ol

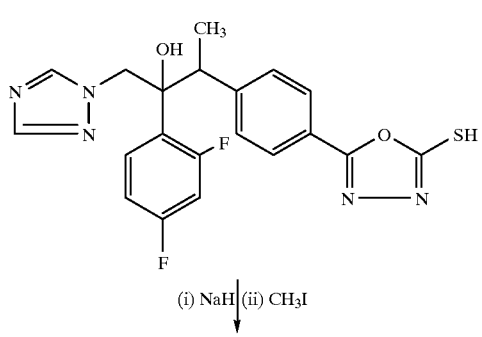

(i) NaH (ii) CH₃I

-continued

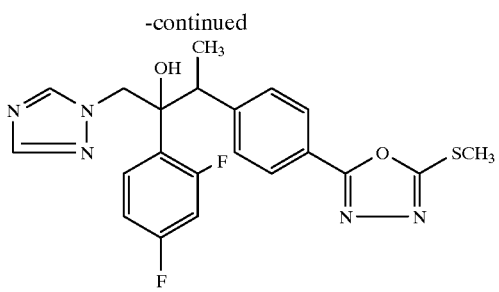

A solution of (2R,3S/2S,3R)-2-(2,4-difluorophenyl)-3-(4-[5-mercapto-1,3,4-oxadiazol-2-yl]phenyl)-1-(1,2,4-triazol-1-yl)butan-2-ol hydrochloride (0.5 g, 1.1 mmol-see Preparation 31) in DMF (5 ml) was treated with sodium hydride (80% dispersion in oil, 0.07 g, 2,4 mmol) and the solution was stirred at room temperature for 0.75 hours. Iodomethane (0.07 ml, 1.1 mmol) was added to the mixture which was stirred for a further hour and then was evaporated under reduced pressure. The residue was partitioned between ethyl acetate (20 ml) and water (20 ml). The organic phase was dried (MgSO$_4$) and evaporated under reduced pressure. The crude product was purified by column chromatography on silica by gradient elution with dichloromethane/methanol (100:0, 98:2, 96:4). Fractions containing the desired product were combined and evaporated under reduced pressure to yield a gum. Trituration of the gum with ether/hexane afforded the title compound (0.23 g, 45%) as a pale yellow solid, which was characterised by $^1$H-N.M.R. spectroscopy (300 MHz, CDCl$_3$): δ=1.14 (d,3H), 2.78 (s,3H), 3.36 (q,1H), 3.85 (d,1H), 4.79 (d,1H), 4.89 (s,1H), 6.7–6.8 (m,2H), 7.48 (m,1H), 7.62 (d,2H), 7.73 (d,2H), 7.95 (s,1H), 8.01 (s,1H).

EXAMPLE 52

(2R,3S/2S,3R)-2-(2,4-Difluorophenyl)-3-(4-[5-methylsulphonyl-1,3,4-oxadiazol-2-yl]phenyl)-1-(1,2,4-triazol-1-yl)butan-2-ol

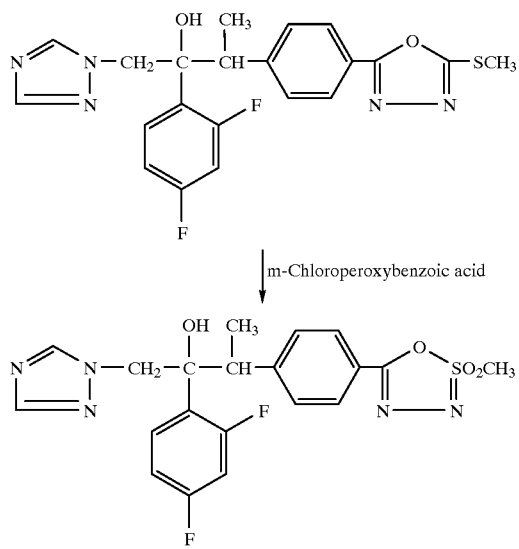

A solution of (2R,3S/2S,3R)-2-(2,4-difluorophenyl)-3-(4-[5-methylthio-1,3,4-oxadiazol-2-yl]phenyl)-1-(1,2,4-triazol-1-yl)butan-2-ol (0.19 g, 0.4 mmol-see Example 51) in dichloromethane (5 ml) was cooled to −70° C. and treated with a solution of m-chloroperoxybenzoic acid (50%, 0.6 g, 1.6 mmol) in dichloromethane (10 ml). The solution was allowed to warm to room temperature and was stirred for 24 hours. The mixture was washed with aqueous sodium hydroxide (2M, 20 ml), dried (MgSO$_4$) and evaporated under reduced pressure.

The residue was chromatographed on silica by gradient elution with dichloromethane/methanol (99:1→90:10). Fractions containing the desired product were combined and evaporated under reduced pressure to yield a foam which was triturated with ether/hexane to give the title compound, (0.12 g, 66%), as a cream-coloured solid, m.p. 180–183° C.

Analysis %: Found: C, 52.93; H, 3.83; N, 14.34. C$_{21}$H$_{19}$F$_2$N$_5$O$_4$S requires: C, 53.04; H, 4.03; N, 14.73.

EXAMPLE 53

(2R,3S/2S,3R)-2-(2,4-Difluorophenyl)-3-(4-[3-methylsulphonyl-1,2,4-triazol-1-yl]phenyl)-1-(1,2,4-triazol-1-yl)butan-2-ol

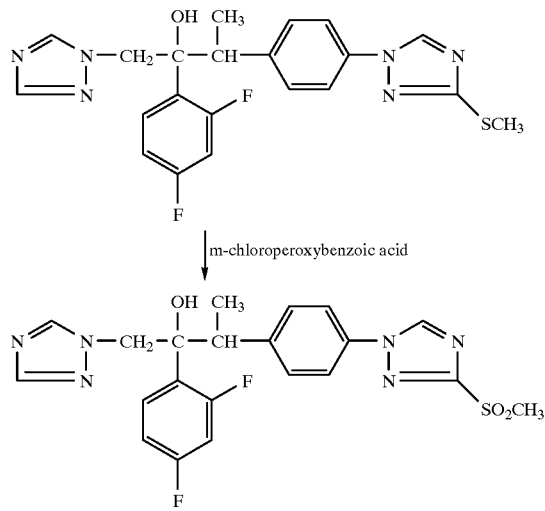

The title compound was prepared from the corresponding methylthio derivative (see Example 22) by a similar method to that of Example 52, and had an m.p. of 139–141° C.

Analysis %: Found: C, 53.26; H, 4.19; N, 17.49. C$_{21}$H$_{20}$F$_2$N$_6$O$_3$S requires: C, 53.16; H, 4.25; N, 17.71.

EXAMPLE 54

(2R,3S/2S,3R)-2-(2,4-Difluorophenyl)-3-(4-[1-ethoxymethyl-3-methylsulphonyl-1,2,4-triazol-5-yl]phenyl)-1-(1,2,4-triazol-1-yl)butan-2-ol

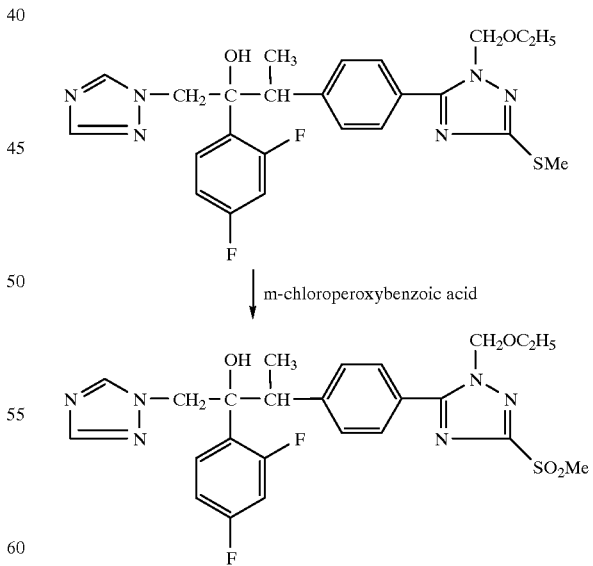

The title compound was prepared from the product of Example 11 by a similar method to that of Example 52.

Analysis %: Found: C, 53.74; H, 5.13; N, 15.72. C$_{24}$H$_{26}$F$_2$N$_6$O$_4$S requires: C, 54.12; H, 4.02; N, 15.78.

EXAMPLE 55

(2R,3S/2S,3R)-2-(2,4-Difluorophenyl)-3-(4-[3-amino-1,2,4-oxadiazol-5-yl)phenyl]-1-(1,2,4-triazol-1-yl)butan-2-ol

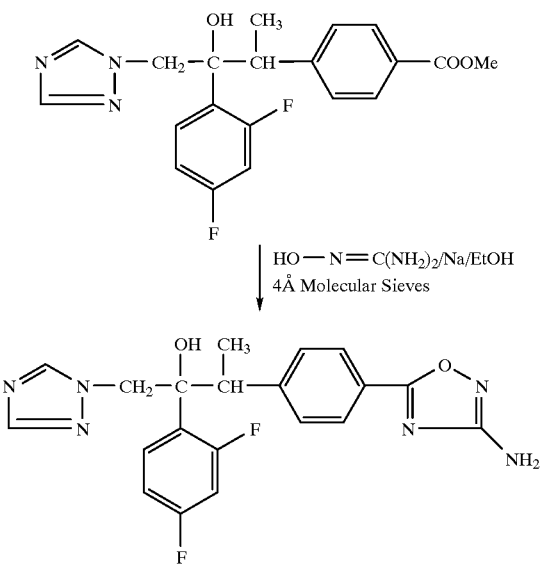

Sodium metal (0.3 g, 13 mmol) was added to a mixture of hydroxy guanidine hemihydrate hemisulphate (0.86 g, 6.5 mmol) and 4 Å molecular sieves (1.3 g) in ethanol (8 ml). After disappearance of all the sodium, (2R,3S/2S,3R)-4-[2-(2,4-difluorophenyl)-2-hydroxy-1-(1,2,4-triazol-1-yl)but-3-yl]benzoic acid methyl ester (0.5 g, 1.3 mmol-see Preparation 23(ii)) was added to the mixture which was heated under reflux for 1 hour. The mixture was neutralised with glacial acetic acid, diluted with water (50 ml) then extracted with ethyl acetate (50 ml). The organic extract was washed with saturated sodium carbonate solution (20 ml), dried (MgSO$_4$) and evaporated under reduced pressure. The residue was chromatographed on silica by elution with ethyl acetate/methanol (95:5). Fractions containing the desired product were combined, evaporated under reduced pressure then triturated with ether/hexane to afford the title compound (0.025 g, 5%) as a colourless solid, m.p. 234–237° C.

Analysis %: Found: C, 58.40; H, 4.48; N, 20.01. $C_{20}H_{18}F_2N_6O_2$ requires: C, 58.24; H, 4.40; N, 20.38.

EXAMPLE 56

(2R,3S/2S,3R)-2-(2,4-Difluorophenyl)-3-(4-[5-amino-1,3,4-oxadiazol-2-yl]phenyl)-1-(1,2,4-triazol-1-yl)butanol

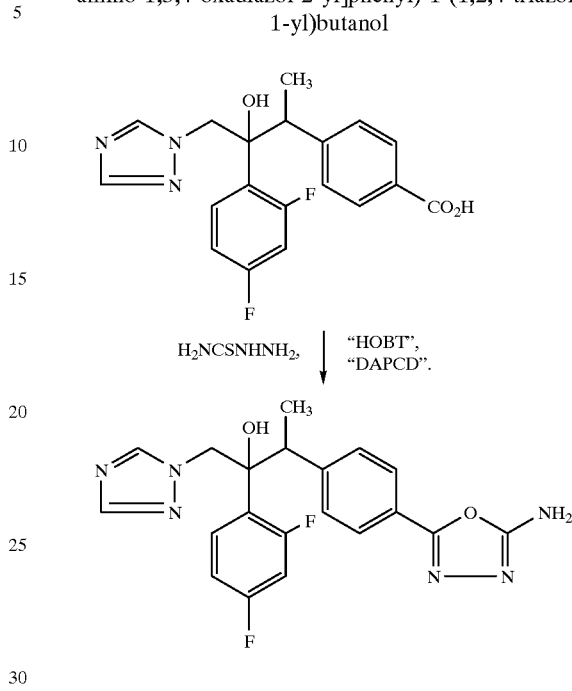

A mixture of (2R,3S/2S,3R)-4-[2-(2,4-difluorophenyl)-2-hydroxy-1-(1,2,4-triazol-1-yl)but-3-yl]benzoic acid (0.51 g, 1.3 mmol-see Preparation 32) 1-hydroxybenzotriazole monohydrate ("HOBT") (0.18 g, 1.3 mmol), thiosemicarbazide (0.12 g, 1.3 mmol) triethylamine (0.37 ml, 2.6 mmol), 1-[3-dimethylaminopropyl]-3-ethylcarbodiimide hydrochloride ("DAPCD") (0.51 g, 2.6 mmol), dimethylformamide (8 ml) and dichloromethane (25 ml) was stirred at room temperature for 2 days. The solvents were removed under reduced pressure and the residue was chromatographed on silica by gradient elution with dichloromethane/methanol (98:2, 95:5, 92:8). Fractions containing the desired product were combined and evaporated under reduced pressure. Trituration with chloroform afforded the title compound as a colourless solid, m.p. 237–242° C.

Analysis %: Found: C, 55.98; H, 4.24; N, 19.88. $C_{20}H_{18}F_2N_6O_2 \cdot \frac{3}{4}H_2O$ requires: C, 56.39; H, 4.61; N, 19.73.

EXAMPLE 57

(2R,3S/2S,3R)-2-(2,4-Difluorophenyl)-3-(5-[2,5-dimethylpyrrol-1-yl)]pyridin-2-yl)-1-(1,2,4-triazol-1-yl)butan-2-ol

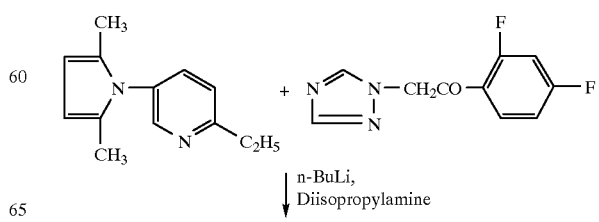

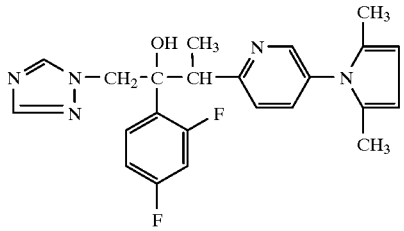

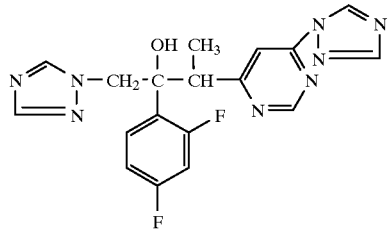

To a solution of diisopropylamine (1.7 ml, 12 mmol) in dry THF (50 ml) at −20° C. under a nitrogen atmosphere was added dropwise a solution of n-butyllithium in hexane (2.5M, 4.9 ml, 12 mmol). After stirring for 0.25 hours, the mixture was cooled to −70° C. and was treated with a solution of 5-(2,5-dimethylpyrrol-1-yl)-2-ethylpyridine (2.38 g, 12 mmol-see Preparation 33) in THF (15 ml). The resulting mixture was stirred at this temperature for 0.75 hours then treated with a solution of 1-(2,4-difluorophenyl)-2-(1,2,4-triazol-1-yl)ethanone (2.6 g, 12 mmol-see e.g. EP-A-0069442) in THF (30 ml). The solution was stirred at this temperature for 0.5 hours and the reaction was quenched by addition of aqueous acetic acid (10%, 70 ml) and allowed to warm to room temperature. The mixture was diluted with water (100 ml) and extracted with ethyl acetate (2×50 ml).

The title compound was prepared from 4-ethyl-6-(1,2,4-triazol-1-yl)pyrimidine (see Preparation 34) using a similar method to the previous Example, m.p. 205–207° C. (from ethyl acetate/methanol).

Analysis %: Found: C, 54.37; H, 3.99; N, 28.08. $C_{18}H_{16}F_2N_8O$ requires: C, 54.27; H, 4.05; N, 28.13.

EXAMPLE 59

2-(2,4-Difluorophenyl)-3-(2-fluoro-4-[1,2,3-triazol-4-yl]phenyl)-1-(1,2,4-triazol-1-yl)butan-2-ol

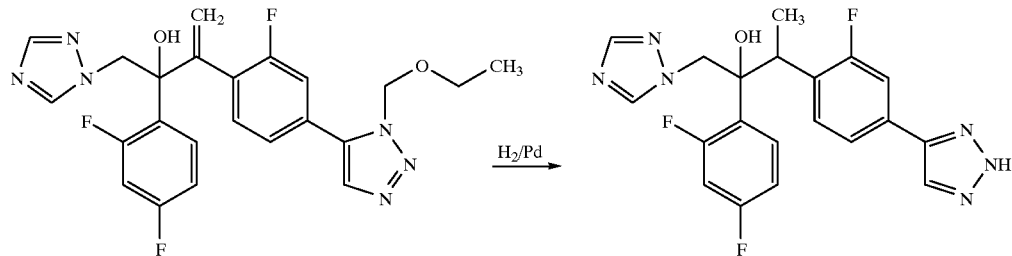

The combined organic extracts were dried (MgSO₄) and evaporated under reduced pressure. The residue was chromatographed on silica by gradient elution with ethyl acetate/hexane (30:70, 50:50) to give the title compound (0.5 g, 10%) as a colourless solid, m.p. 138–139° C.

Analysis %: Found: C, 65.31; H, 5.36; N, 16.58. $C_{23}H_{23}F_2N_5O$ requires: C, 65.23; H, 5.48; N, 16.54.

EXAMPLE 58

(2R,3S/2S,3R)-2-(2,4-Difluorophenyl)-3-(6-[1,2,4-triazol-1-yl]pyrimidin-4-yl)-1-(1,2,4-triazol-1-yl)butan-2-ol

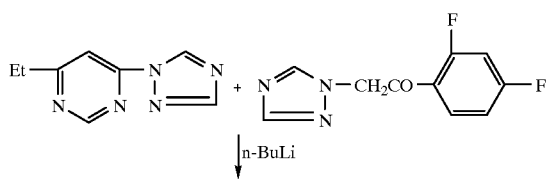

A solution of 2-(2,4-difluorophenyl)-3-(2-fluoro-4-[1-[ethoxymethyl-1,2,3-triazol-5-yl]phenyl)-1-(1,2,4-triazol-1-yl)-3-buten-2-ol(0.26 g, 0.5 mmol-see Preparation 52) in ethanol (20 ml) was hydrogenated at 50 psi (333 kPa) pressure over 10% palladium on charcoal (0.2 g) for 18 hours at 50° C. The mixture was filtered through "Arbocel" (Trade Mark) and the filtrate was concentrated under reduced pressure. The residue was purified by flash chromatography on silica by gradient elution with ethyl acetate/hexane (1:1, 3:1, then 1:0). The product diastereoisomers were not separated, hence fractions containing both isomers were combined and evaporated under reduced pressure to yield the title compound as a colourless foam (0.042 g, 18%). The product was characterised as a 5:1 mixture of the (2R,3S/2S,3R) and (2R,3R/2S,3S) diastereomers by NMR.

¹H-NMR (300 MHz, CDCl₃): δ=1.12(d,2.5H), 1.56(d, 0.5H), 3.90(q,1H), 3.98(d,0.8H), 4.69(d,0.2H), 4.82(s,0.8H), 4.93(s,0.2H), 5.01(d,0.8H), 5.11(d,0.2H), 6.8(m,2H), 7.4–7.65(m,4H), 7.76(s,1H), 7.83(s,1H), 7.98(s,1H), 12.7 (br.s,1H) ppm.

EXAMPLE 60

(2R,3S/2S,3R)-2-(2,4-Difluorophenyl)-3-(4-[5-methyl-1,2,3-triazol-4-yl]phenyl)-1-(1,2,4-triazol-1-yl)butan-2-ol 41 42

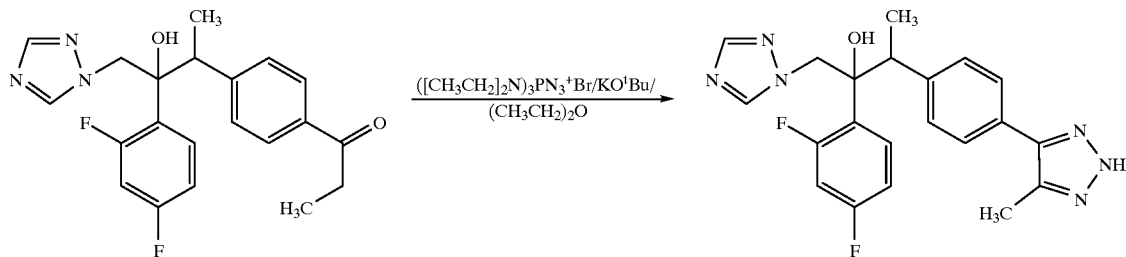

A suspension of azidotris(diethylamino)phosphonium bromide (0.52 g, 1.4 mmol-see Tetrahedron Letters 1990 31 4987 for preparation) in dry ether (10 ml) was treated with a solution of (2R,3S/2S,3R)-2-(2,4-difluorophenyl)-3-(4-propanoylphenyl)-1-(1,2,4-triazol-1-yl)butan-2-ol (0.5 g, 1.3 mmol-see Preparation 47) in diethyl ether (10 ml). Catalytic quantities of potassium tert-butoxide were added until a permanent colour change occurred, the mixture was then stirred at room temperature overnight. The reaction was quenched by addition of saturated ammonium sulphate solution and the layers were separated. The organic phase was dried (MgSO$_4$) and evaporated under reduced pressure. The residue was purified by flash chromatography on silica by elution with ethyl acetate/diethylamine (19:1) followed by ethyl acetate/methanol (19:1). Fractions containing the desired product were combined and evaporated under reduced pressure to yield the title compound (0.05 g, 9%) as a colourless solid, m.p. 169–171° C.

Analysis % Found: C,61.71; H,5.13; N,19.42 C$_{21}$H$_{20}$F$_2$N$_6$O.¼ Et$_2$O requires C,61.68; H,5.14; N,19.62

EXAMPLE 61

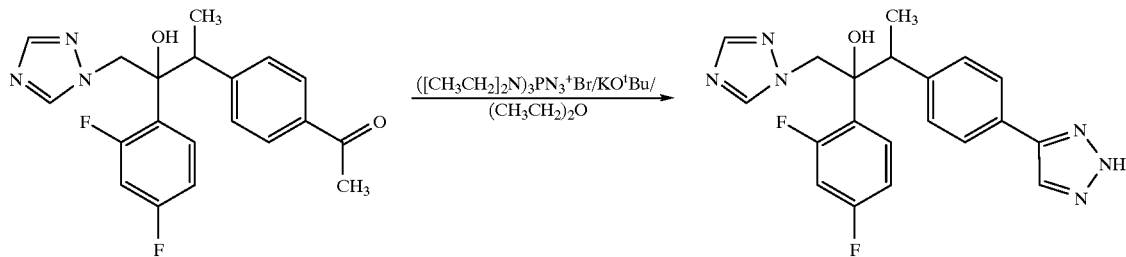

(2R,3S/2S,3R)-2-(2,4-Difluorophenyl)-3-(4-[1,2,3-triazol-4-yl]phenyl)-1-(1,2,4-triazol-1-yl)butan-2-ol The title compound was prepared from (2R,3S/2S,3R)-2-(2,4-difluoro-phenyl)-3-(4-ethanoylphenyl)-1-(1,2,4-triazol-1-yl)butan-2-ol (see Preparation 48) by the method of Example 60. The product was characterised by $^1$H NMR and was identical to the product of Example 15 (2R,3S/2S,3R form).

$^1$H-NMR (300 MHz, CDCl$_3$): δ=1.18(d,3H), 3.39(q,1H), 3.93(d,1H), 4.76(s,1H), 4.82(d,1H), 6.77(m,2H), 7.50(q,1H), 7.60(d,1H), 7.73(s,1H), 7.80(s,1H), 7.81(d,1H), 7.98 (s,1H) ppm.

EXAMPLE 62

(2R,3S/2S,3R)-2-(2,4-Difluorophenyl)-3-(4-[2-ethoxymethyl-1,2,3-triazol-4-yl]phenyl)-1-(1,2,4-triazol-1-yl)butan-2-ol and (2R,3S/2S,3R)-2-(2,4-difluorophenyl)-3-(4-[1-ethoxymethyl-1,2,3-triazol-4-yl]phenyl)-1-(1,2,4-triazol-1-yl)butan-2-ol

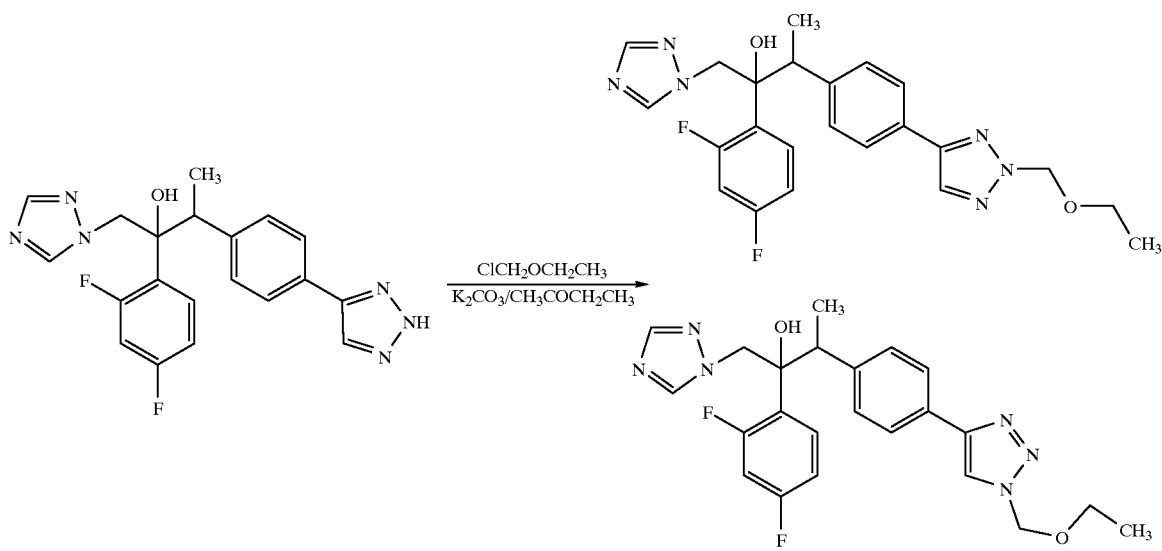

A solution of (2R,3S/2S,3R)-2-(2,4-difluorophenyl)-3-(4-[1,2,3-triazol-4-yl]phenyl)-1-(1,2,4-triazol-1-yl)butan-2-ol (0.5 g, 1.2 mmol-a product of Example 15) in butan-2-one (40 ml) was treated with potassium carbonate (0.35 g, 2,4 mmol) followed by chloromethyl ethyl ether (0.12 ml, 1.2 mmol). The mixture was stirred at room temperature for 18 hours. The solvent was removed under reduced pressure and the residue partitioned between water (10 ml) and ethyl acetate (20 ml). The aqueous phase was extracted with ethyl acetate (2×20 ml) and the combined organic layers were extracted with brine (2×10 ml), dried (Na$_2$SO$_4$) and evaporated under reduced pressure. The colourless solid residue was flash chromatographed on silica by gradient elution with hexane/isopropanol (49:1,9:1). Pure fractions containing each regioisomer were combined and evaporated under reduced pressure. Both title compounds were obtained by trituration with ether as colourless solids. The structure of each regioisomer was assigned by n.O.e measurement.

(2R,3S/2S,3R)-2-(2,4-difluorophenyl)-3-(4-[2-ethoxymethyl-1,2,3-triazol-4-yl]phenyl)-1-(1,2,4-triazol-1-yl)butan-2-ol(0.17 g, 30%) had a m.p. of 118–120° C.

| Analysis % | | | |
|---|---|---|---|
| Found: | C, 60.80; | H, 5.48; | N, 18.03 |
| C$_{23}$H$_{24}$F$_2$N$_6$O$_2$ requires | C, 60.78; | H, 5.32; | N, 18.49 |

(2R,3S/2S,3R)-2-(2,4-difluorophenyl)-3-(4-[1-ethoxymethyl-1,2,3-triazol-4-yl]phenyl)-1-(1,2,4-triazol-1-yl)butan-2-ol (0.0979, 17%) had a m.p. 153–156° C.

| -continued | | | |
|---|---|---|---|
| Analysis % | | | |
| Found: | C, 60.77; | H, 5.42; | N, 18.13 |
| C$_{23}$H$_{24}$F$_2$N$_6$O$_2$ requires | C, 60.78; | H, 5.32; | N, 18.49 |

EXAMPLE 63

(2R,3S/2S,3R)-2-(2,4-Difluorophenyl)-3-(4-[1,2,3-triazol-4-yl]phenyl)-1-(1,2,4-triazol-1-yl)butan-2-ol A solution of (2R,3S/2S,3R)-2-(2,4-difluorophenyl)-3-(4-[1-benzyl-1,2,3-

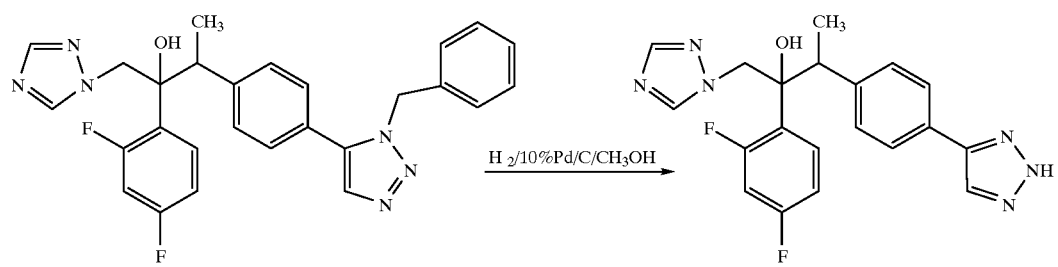

triazol-5-yl]phenyl)-1-(1,2,4-triazol-1-yl)butan-2-ol(0.3 g, 0.6 mmol-a product of Example 28) in methanol (100 ml) was hydrogenated at 50 psi (333 kPa) pressure over 10% palladium on charcoal (0.1 g) for 18 hours at 100° C. The cooled mixture was filtered through "Arbocel" and the filtrate was concentrated under reduced pressure. The residue was purified by flash chromatography on silica by gradient elution with dichloromethane/methanol (39:1, 19:1). Fractions containing the desired product were combined and evaporated under reduced pressure to yield the title compound as a colourless solid (0.18 g, 71%). The product was confirmed to be identical to the product of Example 44 by NMR.

| Analysis % | | | |
|---|---|---|---|
| Found: | C, 61.10; | H, 4.96; | N, 20.50 |
| $C_{20}H_{16}F_2N_6O$ requires | C, 60.59; | H, 4.58; | N, 21.21 |

EXAMPLE 64

2-(2,4-Difluorophenyl)-3-(4-[1,2,3-triazol-4-yl] phenyl)-1-(1,2,4-triazol-1-yl)butan-2-ol

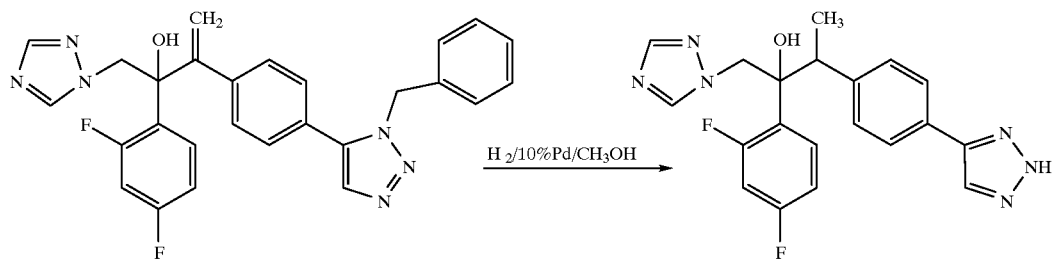

A solution of 2-(2,4-difluorophenyl)-3-(4-[1-benzyl-1,2,3-triazol-5-yl]phenyl)-1-(1,2,4-triazol-1-yl)-3-buten-2-ol (0.15 g, 0.3 mmol-see Preparation 43) in methanol (100 ml) was hydrogenated at 50 psi (333 kPa) pressure over 10% palladium on charcoal (0.1 g) for 18 hours at 100° C. The cooled mixture was filtered through "Arbocel" and the filtrate was concentrated under reduced pressure. The residue was purified by flash chromatography on silica by elution with dichloromethane/methanol (19:1). Fractions containing the desired product were combined and evaporated under reduced pressure to yield the title compound as a gum (0.1 g, 81%). The product was a mixture of diastereomers by NMR.

EXAMPLE 65

2-(2,4-Difluorophenyl)-3-(3-[1,2,3-triazol-4-yl] phenyl)-1-(1,2,4-triazol-1-yl)butan-2-ol

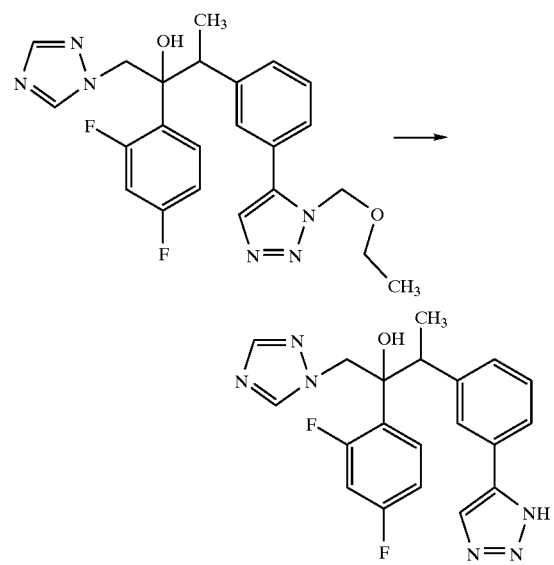

The title compound as a mixture of diastereomers was prepared by a similar method to Example 42 as a colourless solid, m.p. 168–170° C. The starting material was prepared analogously to the method of Example 1 and Preparation 12.

| Analysis % | | | |
|---|---|---|---|
| Found: | C, 60.93; | H, 4.59; | N, 20.94 |
| $C_{20}H_{16}F_2N_6O$ requires | C, 60.59; | H, 4.58; | N, 21.21 |

EXAMPLE 66

(2R,3S)-2-(2,4-Difluorophenyl)-1-(1H-1,2,4-triazol-1-yl-3-[4-(1H-1,2,3-triazol-4-yl)phenyl]-2-butanol

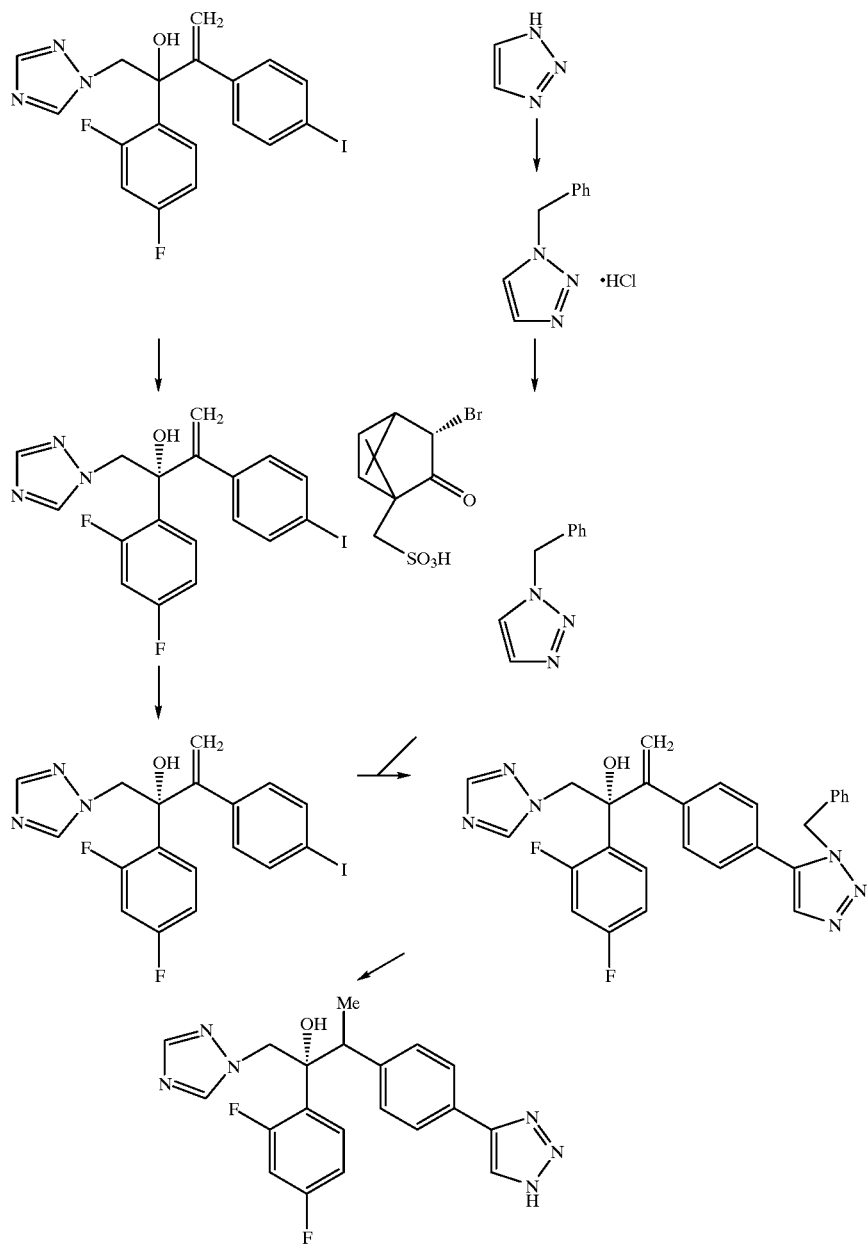

i) (R)-2-(2,4-Difluorophenyl)-3-(4-iodophenyl)-1-(1H-1,2,4-triazol-1-yl)-3-buten-2-ol(+)-3-Bromocamphor-10-sulphonate.

A solution of (+)-3-bromocamphor-10-sulphonic acid (36.3 g, 0.110 moles) in IMS (40 ml) was added to a solution of 2-(2,4-difluorophenyl)-3-(4-iodophenyl)-1-(1H-1,2,4-triazol-1-yl)-3-buten-2-ol (50 g, 0.110 moles) in IMS (300 ml). After seeding, the resulting slurry was granulated for 20 hours at room temperature. A white solid (22 g, 0.03 moles) was collected by filtration after further granulating for 1 hour at low temperature. The chiral purity was assessed as 95% ee by chiral HPLC using a chiralcel OD (trademark) column and eluting with ethanol:hexane, 40:60.

(II) (R)-2-(2,4-Difluorophenyl)-3-(4-iodophenyl)-1-(1H-1,2,4-triazol-1-yl-3-buten-2-ol (R)-2-(2,4-Difluorophenyl)-3-(4-iodophenyl)-1-(1H-1,2,4-triazol-1-yl)-3-buten-2-ol (+)-3-bromocamphor-10-sulphonate (206.5 g, 0.27 moles) was added to methylene chloride (620 ml) and water (620 ml) and basified with 40% NaOH. The mixture was stirred for 15 minutes at room temperature and separated. The aqueous phase was re-extracted with methylene chloride (310 ml). The organic product solution was water washed (620 ml) and concentrated to a volume of 245 ml. To the stirred and seeded concentrate at room temperature was added hexane (2450 ml) at a steady rate. The resulting slurry was granulated at 5° C. for 1 hour. Filtration afforded a white solid (117.4 g, 0.26 moles) which was characterised by $^1$H-NMR spectroscopy.

$^1$H NMR (300 MHz, CDCl$_3$): δ=4.55 (d, J=15 Hz, 1H) 4.90 (d, J=15 Hz, 1H), 5.16 (s, 1H), 5.25 (s, 2H), 6.70 (m,2H), 7.03 (d, J=9 Hz, 2H) 7.43 (dt, J=7 and 9 Hz, 1H), 7.58 (d, J=9 Hz, 2H), 7.79 (s,1H), 7.80 (s, 1H) ppm.

(iii) 1-Benzyl-1H-1,2,3-triazole hydrochloride.

1,2,3-Triazole (79 g, 1.1 mole) and potassium carbonate (138 g, 1 mole) were refluxed in acetone (530 ml). A solution of benzyl bromide (171 g, 1 mole) in acetone (250 ml) was added to the resulting slurry over 1.5 hours maintaining reflux. The reaction was stirred at reflux for a further 1 hour and then cooled to room temperature. One litre of water was added and the acetone removed by evaporating under reduced pressure. The product was extracted with methylene chloride (700 ml) and separated. The aqueous phase was further extracted with methylene chloride (250 ml) and the combined organic extracts washed with water (400 ml). The product solution was concentrated to an oil (162 g). To a stirred solution of the oil in ethyl acetate (305 ml) was added 22% HCl/IPA (166 ml, 1 mole) at a steady rate at room temperature. The resulting slurry was granulated at room temperature for 1 hour and for a further hour at 0° C. The filtered product (144 g, 0.74 moles) was analysed to be 93.3% N-1 isomer by HPLC using a Dynamax C18 column and acetonitrile:water, 65:35 eluent.

(iv) 1-Benzyl-(1H)-1,2,3-triazole

A stirred mixture of 1-benzyl-(1H)-1,2,3-triazole hydrogen chloride (80 g 0.41 moles) in water (320 ml) and ethyl acetate (320 ml) was basified with 20% NaOH (91 ml). The mixture was stirred at room temperature for 10 minutes and separated. The aqueous phase was re-extracted with ethyl acetate (160 ml) and the combined organic product solutions were washed with water (160 ml). The product solution was concentrated to a volume of 195 ml and cooled to room temperature. To the stirred ethyl acetate concentrate was added hexane (585 ml) over 15 minutes. The resulting seeded slurry was granulated at 0° C. for 1 hour. The filtered white solid (62,4 g, 0.39 moles) was characterised by $^1$H-NMR spectroscopy.

$^1$H-NMR (300 MHz, CDCl$_3$): δ=5.55 (s, 2H), 7.25 (m, 2H), 7.35 (m, 3H), 7.45 (s, 1H), 7.70 (s, 1H) ppm.

v) (R)-3-(4-[1-Benzyl-1H-1,2,3-triazol-5-yl]phenyl)-2-(2,4-difluororohenyl)-1-(1H-1,2,4-triazol-1-yl)-3-buten-2-ol nBuLi (1.6N, 24.1 ml, 0.04 moles) was added to a solution of 1-benzyl-(1H)-1,2,3-triazole (6.14 g, 0.04 moles) in THF (370 ml) at −70° C. keeping the temperature below −60° C. and stirred for 30 minutes. Maintaining a temperature below −40° C., a solution of zinc chloride (0.5N, 77.1 ml, 0.04 moles) was added, followed by palladium tetrakis (triphenylphosphine)(15% w/w 0.9 g). Still keeping the temperature below −40° C. a solution of (R)-2-(2,4-difluorophenyl)-3-(4-iodophenyl)-1-(1H-1,2,4-triazol-1-yl)-3-buten-2-ol (6.0 g, 0.013 moles) in THF (36 ml) was added at a steady rate. The reaction was allowed to warm to room temperature and then refluxed for 2 hours. After cooling to room temperature the reaction was quenched with acetic; acid (12 ml) and water (120 ml) keeping the temperature below 25° C. The reaction mixture was evaporated under reduced pressure to remove the THF. The product was extracted with methylene chloride (120 ml) and the aqueous phase further extracted with methylene chloride (50 ml). The combined organic extracts were washed with water (2×120 ml) and concentrated to give an oil (15.6 g). To a stirred filtered solution the oil in ethyl acetate (100 ml) was added 5-sulphosalicyclic acid (3.3 g, 0.13 moles) in IPA (10 ml). The resulting mixture was stirred at room temperature for ½ hour. The resulting filtered solid was repulped in ethyl acetate (50 ml) and recrystallised from IPA (60 ml) to afford a white solid (7.2 g, 0.01 moles). The solid was added to methylene chloride (35 ml) and water (50 ml) and basified with 40% NaOH. The mixture was stirred at room temperature for 15 minutes and separated. The aqueous phase was re-extracted with methylene chloride (25 ml) and the combined organic extracts washed with water (35 ml). The organic product solution was concentrated to an oil (4.9 g) and characterised by $^1$H-NMR spectroscopy.

$^1$H-NMR (300 MHz, CDCl$_3$). δ=4.62 (d, J=14 Hz, 1H), 4.92 (d, J=14 Hz, 1H), 5.31 (d, J=26H$_3$, 2H), 5.35 (s, 1H), 5.48 (s, 2H), 6.66 (m, 2H), 6.98 (m, 2H), 7.10 (d, J=8 Hz, 2H), 7.20 (m, 3H), 7.28 (d, J=8 Hz, 2H), 7.41 (m, 1H), 7.64 (s, 1H), 7.71 (s, 1H), 7.88 (s, 1H) ppm.

(vi) (2R,3S)-2-(2,4-Difluorophenyl)-1-(1H-1,2,4-triazol-1-yl)-3-[4-(1H-1,2,3-triazol-4-yl)phenyl]-2-butanol (R)-3-(4-[1-Benzyl-1H-1,2,3-triazol-5-yl]phenyl)-2-(2,4-difluorophenyl)-1-(1H-1,2,4-triazol-1-yl)-3-buten-2-ol (25.0 g, 0.05 moles) was dissolved in methanol (2400 ml) and hydrogenated at 100° C., 60 psi with 5% Pd/C for 20 hours. After catalyst removal by filtration the product solution was concentrated to a white foam (19.1 g, 0.05 moles). A sample was crystallised from ethanol/water and characterised by $^1$H NMR spectroscopy. It had an m.p. of 121° C.

$^1$H-NMR (300 MHz, CDCl$_3$). δ=1.16 (d, J=7 Hz, 3H), 3.35 (q, J=7 Hz, 1H), 3.94 (d, J=15 Hz, 1H), 4.70 (s, 1H), 4.81 (d, J=14 Hz, 1H), 6.78 (m, 2H), 7.50 (m, 1H), 7.57 (d, J=8 Hz, 2H), 7.70 (s, 1H), 7.74 (s, 1H), 7.80 (d, J=8 Hz, 2H), 7.95 (s, 1H) ppm.

EXAMPLE 67

(2R,3S)-2-(2,4-Difluorophenyl)-3-(4-[1-methylpyrazol-5-yl]phenyl)-1-(1,2,4-triazol-1-yl)butan-2-ol

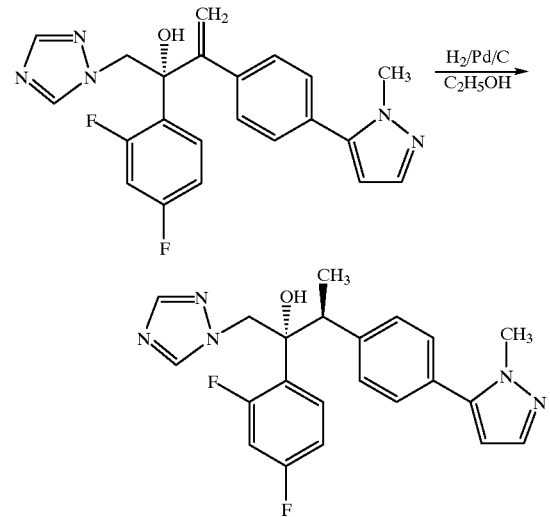

A solution of (2R)-2-(2,4-difluorophenyl)-3-(4-[1-methylpyrazol-5-yl]phenyl)-1-(1,2,4-triazol-1-yl)-3-buten-2-ol (2.0 g, 5 mmol-see Preparation 53) in ethanol (50 ml) was hydrogenated at 50 psi (333 KPa) pressure over 5% palladium on charcoal (0.2 g) for 18 hours at 50° C. A further batch of catalyst (0.2 g) was added, and the hydrogenation was continued for a further 18 hours. The mixture was filtered through "Arbocel" (Trade Mark) and the filtrate evaporated under reduced pressure.

The residue was chromatographed on silica by gradient elution with ethyl acetate/hexane/diethylamine (0:95:5→65:33:2). Fractions containing the desired product were combined and evaporated under reduced pressure. The residue was dissolved and re-evaporated from ethyl acetate (x3) then from ether (x3) to yield a colourless solid. The solid was recrystallised from aqueous ethanol to give the title compound (1.25 g, 62%) as a colourless solid, m.p. 144–145° C., $[\alpha]_D^{25} = -107°$ (c=0.1%, $CH_2Cl_2$).

Analysis % Found: C, 64.26; H, 5.13; N, 17.07. $C_{22}H_{21}F_2N_5O$ requires: C, 64.54; H, 5.17; N, 17.10.

EXAMPLE 68

(2R,3S)-2-(2,4-Difluorophenyl)-3-(4-[4-chloro-1,2,3-triazol-5-yl]phenyl)-1-(1,2,4-triazol-1-yl)butan-2-ol

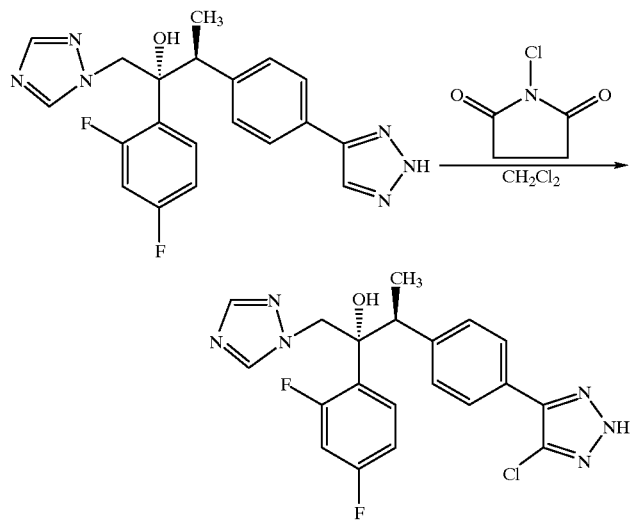

A solution of (2R,3S)-2-(2,4-difluorophenyl)-3-(4-[1,2,3-triazol-4-yl]phenyl)-1-(1,2,4-triazol-1-yl)butan-2-ol (2.0 g, 5 mmol-a product of Example 66) in dichloromethane (100 ml) was treated with N-chlorosuccinimide (0.81 g, 6 mmol). The mixture was stirred and irradiated at room temperature for 3 days then evaporated to dryness under reduced pressure. The residue was partitioned between ethyl acetate (50 ml) and saturated sodium bicarbonate (20 ml). The organic layer was washed with brine (20 ml), dried ($Na_2SO_4$) and evaporated to dryness under reduced pressure.

The residue was chromatographed on silica by gradient elution with hexane/ethyl acetate (2:1→3:2). Fractions containing the desired product were combined and evaporated to yield a colourless oil. The oil crystallised from ethanol/water to give the title compound (1.01 g, 47%) as a colourless solid, m.p. 113–115° C., $[\alpha]_D^{25} = -50°$ (c=0.1%, MeOH).

Analysis % Found: C, 55.91; H, 3.84; N, 19.80. $C_{20}H_{17}ClF_2N_6O$ requires: C, 55.80; H, 3.98; N, 19.51.

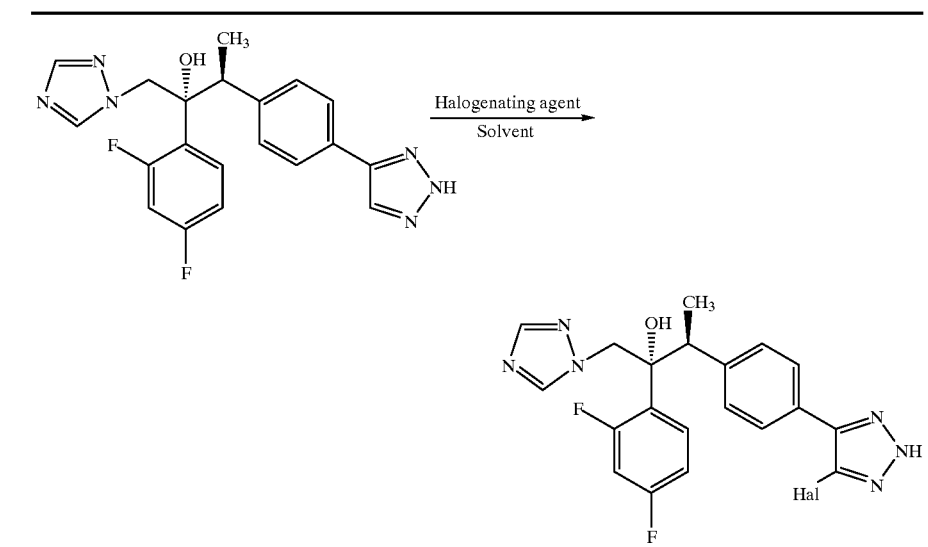

The following examples were prepared by similar methodology to Example 68, with substitution of N-chlorosuccinimide by the appropriate halogenating agent (in Example 71 the reaction was carried out at reflux in acetonitrile)

-continued

| Example No. | Halogenating agent | Hal | M.p. (° C.) | $[\alpha]_D^{25}$ (c = 0.1%, MeOH). | Molecular Formula | Analysis % (Calculated figures in brackets) | | |
|---|---|---|---|---|---|---|---|---|
| | | | | | | C | H | N |
| 69 | N-bromosuccinimide | Br | 123–125 | −54 | $C_2H_{17}BrF_2N_6O$ 1/2 $H_2O$ | 49.64 (49.62) | 3.52 (3.74) | 17.67 (17.36) |
| 70 | N-iodosuccinimide | I | 180–190 | −41 | $C_{20}H_{17}F_2IN_6O$ | (46.46) (45.99) | 3.05 (3.28) | 16.25 (16.09) |
| 71 | Selectfluor ™* | F | 95–97 | −62 | $C_{20}H_{17}F_3N_6O$ | 56.90 (56.74) | 3.91 (4.29) | 20.11 (19.85) |

*see page 20

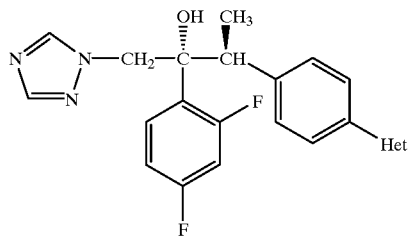

The following compounds were prepared using the method of Example 1, in each case, only the major (2R,3S) enantiomer was isolated.

| Example No. | Het | M.p. (° C.) | $[\alpha]_D^{25}$ (c = 0.1%, MeOH) | Molecular Formula | Analysis % (Calculated figures in brackets) | | |
|---|---|---|---|---|---|---|---|
| | | | | | C | H | N |
| 72 | 1-methyl-4-methylimidazole | 148 | −38 | $C_{22}H_{21}F_2N_5O$ ¼$Et_2O$ | 65.07 (64.60) | 5.73 (5.53) | 16.41 (16.36) |
| 73 | 1-ethyl-5-methylpyrazole | — | — | $C_{23}H_{23}F_2N_5O$ | 64.84 (65.24) | 5.49 (5.47) | 14.14 (16.54) |
| 74 | 1-isopropyl-5-methylpyrazole | — | — | $C_{24}H_{25}F_2N_5O$ | 65.30 (65.89) | 5.71 (5.76) | 14.52 (16.01) |

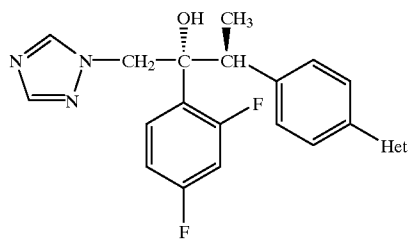

The following compounds were prepared using the method of Example 1, in each case, only the major (2R,3S) enantiomer was isolated.

| Example No. | Het | M.p. (° C.) | $[\alpha]_D^{25}$ (c = 0.1%, MeOH) | Molecular Formula | Analysis % (Calculated figures in brackets) | | |
|---|---|---|---|---|---|---|---|
| | | | | | C | H | N |
| 75 | (1,5-dimethyl-1,2,4-triazol-3-yl) | 162–164 | −11 (in $CH_2Cl_2$) | $C_{21}H_{20}F_2N_6O$ | 61.46 (61.24) | 4.91 (5.04) | 19.58 (19.84) |
| 76 | (1,5-dimethyltetrazol-yl) | 145–147 | −44 | $C_{20}H_{19}F_2N_7O$ | 57.71 (58.39) | 4.47 (4.65) | 23.91 (23.83) |
| 77 | (1-benzyl-5-methyltetrazol-yl) | 85–87 | −36 | $C_{26}H_{23}F_2N_7O$ | 63.61 (64.06) | 5.11 (4.76) | 20.08 (20.11) |

EXAMPLE 78

(2R,3S)-2-(2,4-Difluorophenyl)-3-(4-[tetrazol-5-yl] henyl)-1-(1,2,4-triazol-1-yl)butan-2-ol

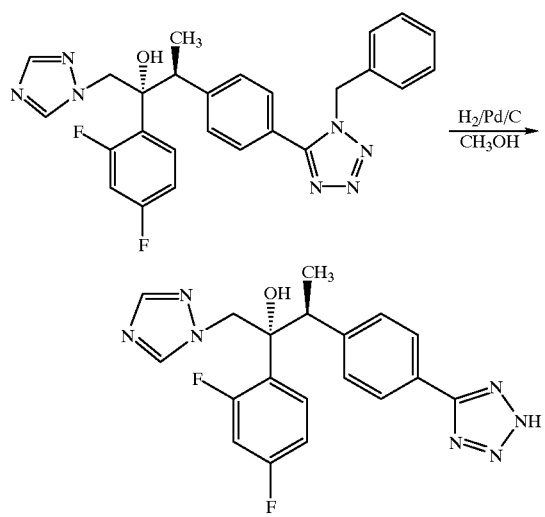

A solution of (2R,3S)-2-(2,4-difluorophenyl)-3-(4-[1-benzyltetrazol5-yl]phenyl)-1-(1,2,4-triazol-1-yl) butan-2-ol (1.0 g, 2 mmol-product of Example 77) in methanol (30 ml) was hydrogenated at 100 psi (666 KPa) pressure over 5% palladium on charcoal (0.2 g) for 18 hours at 50° C. The mixture was filtered through Arbocel™ and the filtrate evaporated under reduced pressure.

The residue was chromatographed on silica by elution with dichloromethane/methanol/acetic acid (95:5:1). Fractions containing the desired product were combined and evaporated under reduced pressure. The residue was precipitated from ethanol with water to give the title compound (0.68 g, 85%) as a colourless solid, m.p. 117–120° C., $[\alpha]_D^{25}$ =−47° (c=0.1%, $CH_3OH$).

Analysis % Found: C, 56.82; H, 4.31; N, 22.84. $C_{19}H_{17}F_2N_7O$ ¼ H2O requires: C, 56.78; H, 4.38; N, 24.40.

EXAMPLE 79

(2R,3S/2S,3 R)-2-(2,4-Difluorolphenyl)-3-(5-[pyrazol-4-yl]pyridin-2-yl)-1-(1,2,4-triazol-1-yl) butan-2-ol

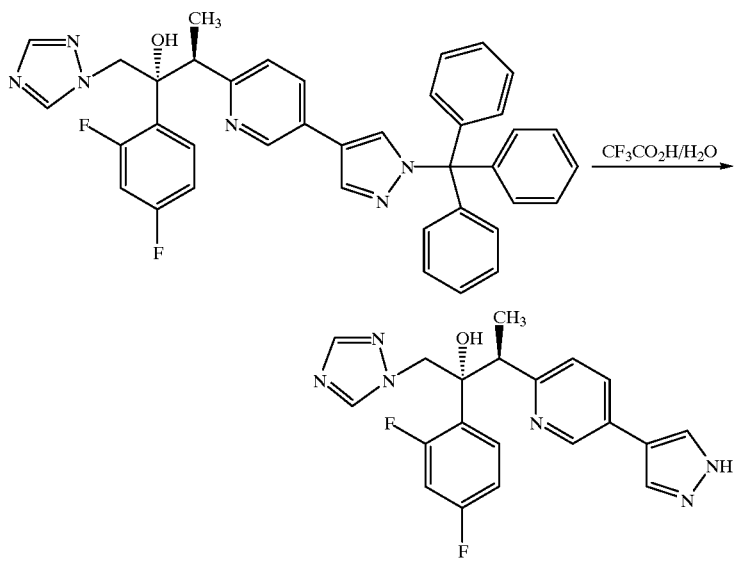

Solid (2R,3S/2S,3SR)-2-(2,4-difluorophenyl)-3-(5-[1-triphenylmethyl-4-pyrazolyl]pyridin-2-yl)-1-(1,2,4-triazol-1-yl)butan-2-ol (0.65 g, 1 mmol) was added to a mixture of trifluoroacetic acid (1.8 ml) and water (0.3 ml) at 0° C. The solution was stirred at 0° C. for 1 hour before quenching with saturated sodium carbonate solution (30 ml). The mixture was extracted three times with ethyl acetate (25 ml) and the combined organic layers were dried (Na$_2$SO$_4$), then evaporated under reduced pressure.

The residue was chromatographed on silica by gradient elution with dichloromethane/ methanol (100:0→95:5). Fractions containing the desired product were combined and evaporated under reduced pressure. The crude product was dissolved in ether and evaporated to give a colourless solid. The solid was recrystallised from hexane/ethyl acetate to give the title compound (0.25 g, 63%) as a colourless solid, m.p. 186–189° C.

Analysis % Found: C, 60.44; H, 4.10; N, 21.26. C$_{20}$H$_{18}$F$_2$N$_6$O requires: C, 60.60; H, 4.58; N, 21.20

EXAMPLE 80

(2R,3S/2S,3R)-2-(2,4-Difluorophenyl)-3-(5-[imidazol-1-yl]pyridin-2-yl)-1-(1,2,4-triazol-1-yl)butan-2-ol

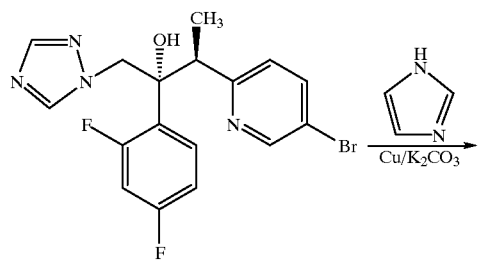

-continued

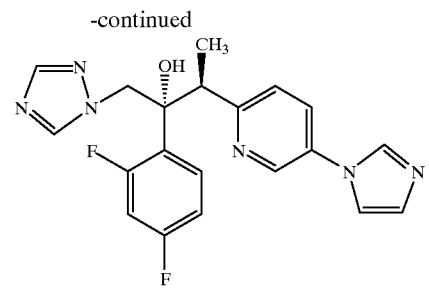

An intimate mixture of (2R,3S/2S,3R)-2-(2,4-difluorophenyl)-3-(5-bromopyridin-2-yl)-1-(1,2,4-triazol-1-yl)butan-2-ol (0.5 g, 1.2 mmol), copper bronze (0.16 g, 2.5 mmol), imidazole (0.42 g, 6 mmol) and potassium carbonate (0.34 g, 2.5 mmol) was heated with stirring to 140° C. for 2 hours. The cooled mixture was suspended in a mixture of dichloromethane (100 ml) and an aqueous solution of ethylenediaminetetraacetic acid disodium salt (5%, 100 ml) and stirred at room temperature for 1 hour. The suspension was filtered through Hyflo™, and the layers were separated. The organic phase was washed with brine (20 ml), dried (Na$_2$SO$_4$) and evaporated under reduced pressure.

The residue was chromatographed on silica by gradient elution with dichloromethane/methanol (100:0→97:3) Fractions containing the desired product were combined and evaporated under reduced pressure. The crude product was dissolved in ether and evaporated to give a the title compound (0.07 g, 14%) as a colourless solid, m.p. 161–163° C.

Analysis % Found: C, 60.52; H, 4.46; N, 21.87 C$_{20}$H$_{18}$F$_2$N$_6$O requires: C, 60.60; H, 4.58; N, 21.20

EXAMPLE 81

(2R,3S/2S,3R)-2-(2,4-Difluorophenyl)-3-(5-[pyrazol-1-yl]pyridin-2-yl)-1-(1,2,4-triazol-1-yl)butan-2-ol The title compound was prepared from pyrazole by a similar method to that of Example 80, as a colourless solid, m.p. 121–123° C.

Analysis % Found: C, 59.68; H, 4.49; N, 20.82
$C_{20}H_{18}F_2N_6O$ ½ $H_2O$ requires: C, 59.63; H, 4.72; N, 20.73

EXAMPLE 82

(2R,3S/2S,3R)-2-(2,4-Difluorophenyl)-3-(5-[1-ethoxymethyl-1,2,3-triazol-5-yl]pyridin-2-yl)-1-(1,2,4-triazol-1-yl)butan-2-ol

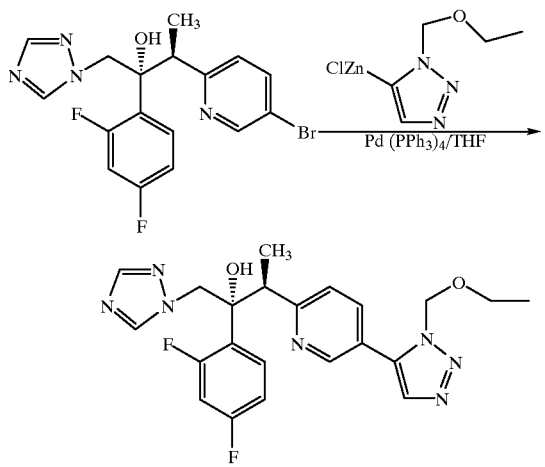

A solution of n-butyllithium in hexane (2.5M, 2.7 ml, 6.8 mmol) was added to a solution of 1-ethoxymethyl-1,2,3-triazole (0.86 g, 6.8 mmol) in dry THF (25 ml) under a nitrogen atmosphere at −70° C. The mixture was stirred for 0.25 hour and treated with a solution of zinc chloride in THF (0.5M, 13.7 ml, 6.8 mmol) then allowed to warm to room temperature. To this mixture was added tetrakis (triphenylphosphine)palladium (0) (0.08 g, 0.1 mmol) and (2R,3S/2S,3R)-2-(2,4-difluorophenyl)-3-(5-bromopyridin-2-yl)-1-(1,2,4-triazol-1-yl)butan-2-ol (0.7 g, 1.7 mmol) and the mixture was heated under reflux for 0.5 hours. Two additional batches of the palladium catalyst (0.08 g) were added before conversion was achieved. The reaction was then heated under reflux for 18 hours. The cooled reaction was quenched with an aqueous solution of ethylenediaminetetraacetic acid disodium salt (5%, 50 ml) and the layers were separated. The aqueous phase was further extracted with ethyl acetate (2×50 ml) and the combined layers were dried ($Na_2SO_4$) and evaporated under reduced pressure.

The residue was chromatographed on silica by gradient elution with dichloromethane/methanol (100:0→97.5:2.5). Fractions containing the desired product were combined and evaporated under reduced pressure to give the title compound (0.62 g, 80%) as a colourless foam.

Analysis % Found: C, 58.47; H, 5.15; N, 21.33
$C_{22}H_{23}F_2N_7O_2$ requires: C, 58.02; H, 5.09; N, 21.53

EXAMPLES 83–86

The following examples were prepared from the appropriate 1-methyl or 1-ethoxymethyl heterocycle and (2R,3S)- or(2R,3S/2S,3R)-2-(2,4-difluorophenyl)-3-(5-bromopyridin-2-yl)-1-(1,2,4-triazol-1-yl)butan-2-ol using a similar method to that of Example 82.

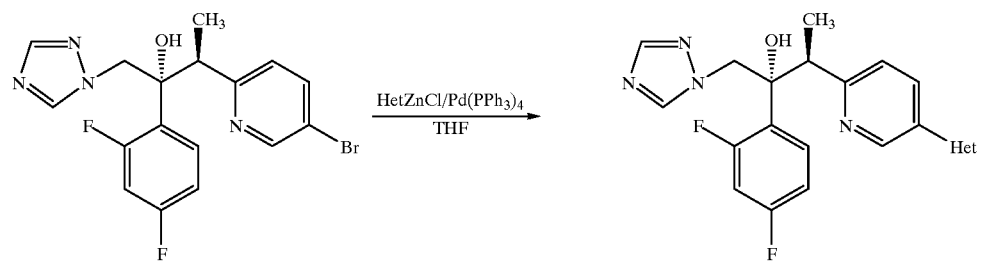

| Example No. | Het | Stereochemistry | M.p. (° C.) | $[\alpha]_D^{25}$ (c = 0.1%, MeOH) | Molecular Formula | Analysis % (Calculated figures in brackets) | | |
|---|---|---|---|---|---|---|---|---|
| | | | | | | C | H | N |
| 83 | (1-methyl imidazole, CH3) | 2R,3S/2S,3R | 128–130 | racemic | $C_{21}H_{20}F_2N_6O$ | 60.97 (61.46) | 4.83 (4.91) | 20.29 (20.48) |
| 84 | (ethoxymethyl triazole) | 2R,3S/2S,3R | Oil | racemic | $C_{22}H_{23}F_2N_7O_2$ | Characterised by $^1H$ N.N.R. (see later) | | |

-continued

| # | Structure | Config | Form | [α] | Formula | C | H | N |
|---|---|---|---|---|---|---|---|---|
| 85 | 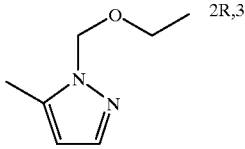 | 2R,3S | Gum | −49 | $C_{23}H_{24}F_2N_6O_2$ ⅛$Et_2O$ | 60.68 (60.91) | 5.52 (5.58) | 17.94 (17.91) |
| 86 | 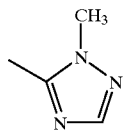 | 2R,3S | Foam | −51 | $C_{20}H_{19}F_2N_7O$ | 58.05 (58.39) | 4.73 (4.65) | 23.81 (23.83) |
| 87 | 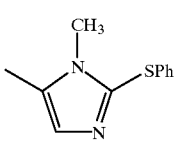 | 2R,3S/2S,3R | — | racemic | $C_{27}H_{24}F_2N_6OS$ | Characterised by $^1$H N.M.R. (see later) | | |

EXAMPLE 84

$^1$H-NMR(300 MHz, CDCl$_3$) δ=1.14 (d, 3H), 1.26 (t, 3H), 3.80 (m, 3H), 4.15 (d, 1H), 4.72 (d, 2H), 5.57 (s, 2H), 6.80 (m, 2H), 7.06 (s, 1H), 7.50 (d, 1H), 7.54 (s, 1H), 7.59 (m, 1H), 7.94 (s, 1H), 8.01 (s, 1H) 8.30 (dd, 1H), 9.11 (d, 1H), ppm.

EXAMPLE 87

$^1$H-NMR(300 MHz, CDCl$_3$) δ=1.12 (d, 3H), 3.68 (s, 3H), 3.72 (q, 1H), 4.17 (d, 1H), 4.75 (d, 1H), 6.7–6.85 (m, 2H), 7.1–7.3 (m, 9H), 7.48 (s, 1H), 7.60 (m, 2H), 7.75 (dd, 1H), 7.92 (s, 1H), 8.60 (d, 1H)ppm.

EXAMPLE 88

(2R,3S/2S,3R)-2-(2,4-Difluorophenyl)-3-(5-[1,2,3-triazol-4-yl]pyridin-2-yl)-1-(1,2,4-triazol-1-yl)butan-2-ol A solution of (2R,3S/2S,3R)-2-(2,4-difluorophenyl)-3-(5-[1-ethoxymethyltriazol-5-yl]pyridin-2-yl)-1-(1,2,4-triazol-1-yl)butan-2-ol (0.09 g, 0.2 mmol-product of Example 82) in ethanol (8 ml) was diluted with water (4 ml) and treated with concentrated hydrochloric acid (1 ml). The mixture was warmed to 80° C. for 1.5 hours then reduced in volume to 3 ml and diluted with water (10 ml). The solution was neutralised with saturated sodium bicarbonate solution, with formation of a colourless precipitate. The suspension was extracted with ethyl acetate (3×30 ml) and the combined extracts washed with brine (20 ml), dried (Na$_2$SO$_4$) and evaporated under reduced pressure. The residue was recrystallised from ethyl acetate to give the title compound (0.05 g, 65%) as colourless solid, m.p. 196–197° C.

Analysis % Found: C, 56.91; H, 4.28; N, 24.60 $C_{19}H_{17}F_2N_7O$ requires: C, 57.43; H, 4.31; N, 24.67

EXAMPLES 89–90

The following examples were prepared from the appropriate (2R,3S)- or (2R,3S/2S,3R)-2-(2,4-difluorophenyl)-3-(1-ethoxymethylheterocyclyl-5-pyridin-2-ly)-1-(1,2,4-triazol-1-ly)butan-2-ol using a similar method to that of Example 88.

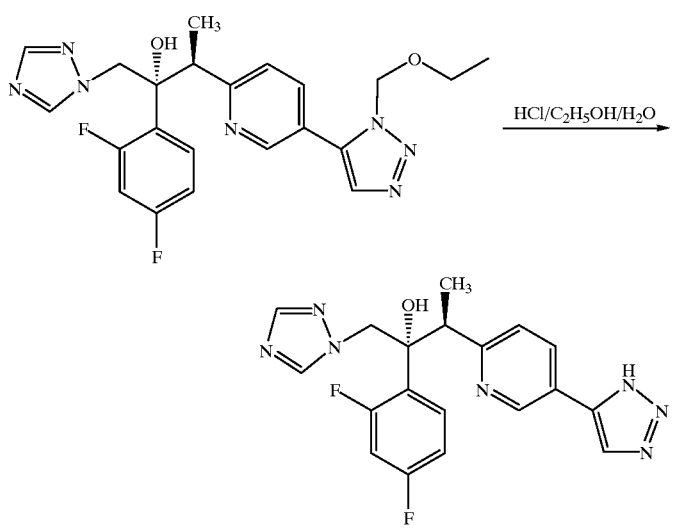

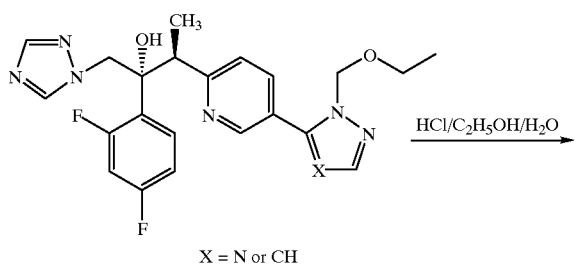

X = N or CH

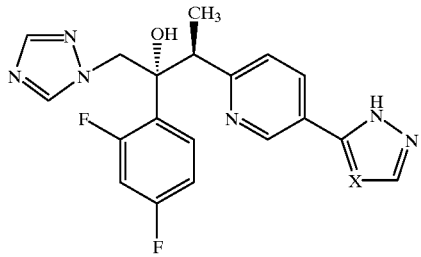

| Example No. | Het | Stereo | M.p. (° C.) | $[\alpha]_D^{25}$ (c = 0.1%, MeOH). | Molecular Formula | Analysis % (Calculated figures in brackets) | | |
| --- | --- | --- | --- | --- | --- | --- | --- | --- |
| | | | | | | C | H | N |
| 89 | 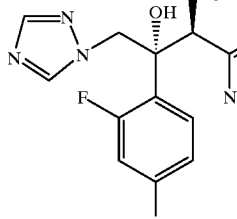 | 2R,3S/2S,3R | Foam | racemic | $C_{19}H_{17}F_2N_7O$ ½ $Et_2O$ ½$H_2O$ | 56.87 (56.88) | 4.69 (5.23) | 21.80 (21.91) |
| 90 | 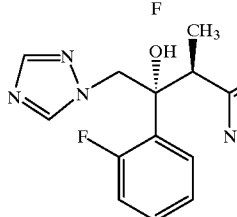 | 2R,3S | Foam | −51 | $C_{20}H_{18}F_2N_6O$ ¼ $Et_2O$ ½$H_2O$ | 59.32 (59.50) | 4.65 (5.11) | 19.94 (19.82) |

EXAMPLE 91

(2R,3S)-2-(2,4-Difluorophenyl)-3-(5-[1-methylpyrazol-5-yl]pyridin-2-yl)-1-(1,2,4-triazol-1-yl)butan-2-ol and (2R,3S)-2-(2,4-Difluorophenyl)-3-(5-[1-methylpyrazol-3-yl]pyridin-2-yl)-1-(1,2,4-triazol-1-yl)butan-2-ol dihydrochloride dihydrate

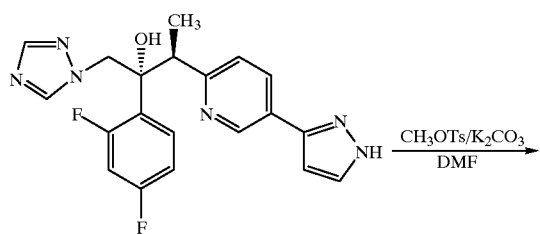

-continued

Methyl p-toluene sulphonate (0.38 g, 2 mmol) was added to a stirred suspension of (2R,3S)-2-(2,4-difluorophenyl)-3-(pyridin-2-yl)-1-(1,2,4-triazol-1-yl)butan-2-ol (0.4 g, 1 mmol, the product of Example 90) and potassium carbonate (0.56 g, 4 mmol) in DMF (10 ml). The mixture was stirred for 3 days at room temperature then poured into water (100 ml) and extracted with ethyl acetate (3×30 ml). The combined organic layers were washed with brine (30 ml), dried (Na$_2$SO$_4$) and evaporated under reduced pressure.

The residue was chromatographed on silica by gradient elution with dichloromethane/methanol (100:0→98:2). Fractions containing the upper spot by tlc (dichloromethane/ methanol 98:2 R$_f$=0.50) were combined and evaporated under reduced pressure. The oily product was dissolved in ether and precipitated by addition of ethereal HCl. The solvent was removed under reduced pressure and the solid suspended in ether and re-evaporated three times to yield (2R,3S)-2-(2,4-difluorophenyl)-3-(S-[1-methylpyrazol-3-yl]pyridin-2-yl)-1-(1,2,4-triazol-1-yl)butan-2-ol dihydrochloride dihydrate (0.17 g, 33%) m.p. 163–167° C., $[\alpha]_D^{25}$=+12.4 (c=0.1%, C$_2$H$_5$OH).

Analysis % Found: C, 49.80; H, 4.63; N, 16.34 C$_{21}$H$_{20}$F$_2$N$_6$O.2HCl.2H$_2$O requires: C, 50.31; H, 4.83; N, 16.76

Fractions containing the lower spot by tlc (dichloromethane/methanol 98:2R$_f$=0.48) were combined and evaporated to give (2R,3S)-2-(2,4-difluorophenyl)-3-(5-[1-methylpyrazol-5-yl]pyridin-2-yl)-1-(1,2,4-triazol-1-yl) butan-2-ol (0.015g, 3%) as colourless foam. This product was identical to the product of Example 83 by tlc and $^1$H-NMR spectroscopy.

EXAMPLE 92–93

The following examples were prepared from (2R,3S)-2-(2,4-difluorophenyl)-3-(5-[pyrazol-3-yl]-5-pyridin-2-yl)-1-(1,2,4-triazol-1-yl)butan-2-ol using a similar method to that of Example 91. In each case, only the 1-substituted-3-pyrazolyl derivative was isolated.

EXAMPLE 94

(2R,3S/2S,3R)-2-(2,4-Difluorophenyl)-3-(2-[1-methylpyrazol-5-yl]pyridin-5-yl)-1-(1,2,4-triazol-1-yl)butan-2-ol

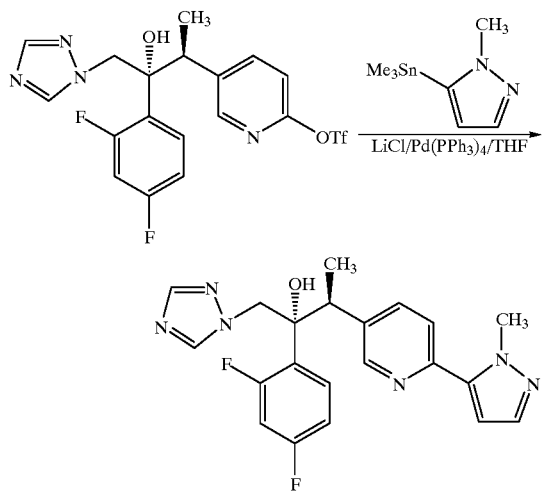

A solution of (2R,3S/2S,3R)-2-(2,4-difluorophenyl)-3-(2-trifluoromethylsulphonyloxy-pyridin-5-yl)-1-(1,2,4-triazol-1-yl)butan-2-ol (0.3 g, 0.6 mmol), (1-methyl-5-pyrazolyl)-trimethylstannane (0.6 g, 2,4 mmol), lithium chloride (0.08 g, 1.8 mmol) and tetrakis(triphenyl-phosphine)palladium (0) (0.04 g, 0.03 mmol) in dioxane (15 ml) was heated under a

| Example No. | RX | R | M.p. (° C.) | $[\alpha]_D^{25}$ (c = 0.1%, MeOH). | Molecular Formula | Analysis % (Calculated figures in brackets) | | |
|---|---|---|---|---|---|---|---|---|
| | | | | | | C | H | N |
| 92 | ClCH$_2$CN | CH$_2$CN | Foam | −41.5 | C$_{22}$H$_{19}$F$_2$N$_7$O ⅛Et$_2$O | 60.37 (60.77) | 4.63 (4.59) | 22.02 (22.05) |
| 93 | BrCH$_2$CONH$_2$ | CH$_2$CONH$_2$ | 143–144 | — | C$_{22}$H$_{21}$F$_2$N$_7$O$_2$ ¼H$_2$O | 57.62 (57.69) | 4.80 (4.73) | 21.72 (21.41) | nitrogen atmosphere for 24 hours. Water (20 ml) was added and the solution basified with aqueous ammonia solution. The mixture was extracted with dichloromethane (50 ml) and the organic layer dried (MgSO$_4$) and evaporated under reduced pressure.

The residue was chromatographed on silica by gradient elution with dichloromethane/methanol (100:0→99:1). Fractions containing the desired product were combined and evaporated under reduced pressure. The crude product was triturated in ether/hexane to give the title compound (0.18 g, 70%) as a colourless solid, m.p. 158–160° C.

Analysis % Found: C, 61.46; H, 4.91; N, 19.58 C$_{21}$H$_{20}$F$_2$N$_6$O requires: C, 61.24; H, 5.04; N, 19.84

EXAMPLE 95

(2R,3S/2S,3R)-2-(2,4-Difluorophenyl)-3-(5-[1-methylimidazol-5-yl]pyridin-2-yl)-1-(1,2,4-triazol-1-yl)butan-2-ol

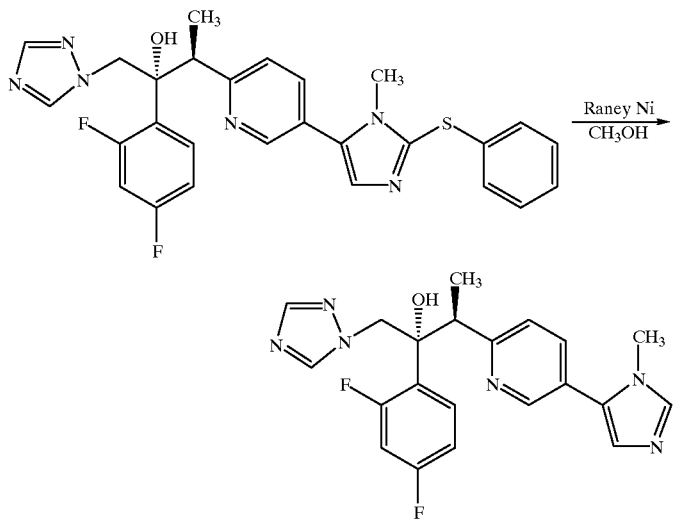

The title compound was prepared from (2R,3S/2S,3R)-2-(2,4-difluorophenyl)-3-(5-[1-methyl-2-phenylthioimidazol-5-yl]pyridin-2-yl)-1-(1,2,4-triazol-1-yl)butan-2-ol by a similar method to Example 35, as a colourless foam.

Analysis % Found: C, 58.87; H, 5.18; N, 19.61 C$_{21}$H$_{20}$F$_2$N$_6$O. H$_2$O requires: C, 58.87; H, 4.85; N, 19.28

EXAMPLE 96

(2R,3S)-2-(2,4-Difluorophenyl)-3-(4-[3-mercapto-4-methyl-1,2,4-triazol-5-yl]phenyl)-1-(1,2,4-triazol-1-yl)butan-2-ol

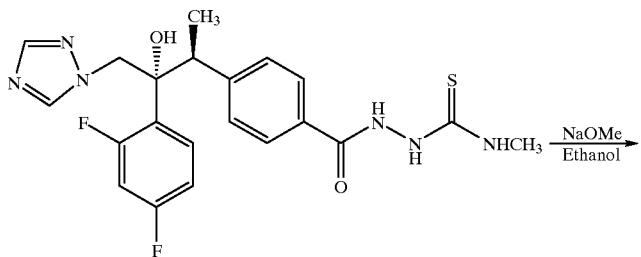

A solution of N-methyl-4-{2-[2,4-difluorophenyl]-2-hydroxy-1-[1,2,4-triazol-1-yl]but-3-yl}benzoylthiosemicarbazide (2.1 g, 4.5 mmol) in ethanol (50 ml) was heated under reflux and treated with sodium methoxide solution (30%, 5.5 mmol) in portions over 24 hours. The mixture was reduced in volume to 20 ml under reduced pressure and partitioned between ethyl acetate (100 ml) and water (50 ml). The aqueous layer was further extracted with ethyl acetate (3×50 ml) and the organic extracts combined, washed with brine (50 ml), dried ($Na_2SO_4$) and evaporated under reduced pressure.

The residue was chromatographed on silica by gradient elution with ethyl acetate/hexane (1:1→3:2). Fractions containing the desired product were combined and evaporated under reduced pressure. The crude product was triturated in ether to give the title compound (0.66 g, 33%) as a colourless solid, m.p. 131–134° C., $[\alpha]_D^{25}=-38°$ (c=0.1%, $CH_3OH$).

$^1$H-NMR (300 MHz, $CDCl_3$) δ=1.2 (d, 3H), 3.5 (q, 1H), 3.8 (d, 1H), 4.8 (d, 1H), 4.95 (d, 1H), 6.80 (m, 2H), 7.50 (m, 1H), 7.6 (d, 2H), 7.7 (d, 2H), 7.75 (s, 1H), 7.8 (s, 1H), 11.0(br.s, 1H) ppm.

EXAMPLE 97

(2R,3S)-2-(2,4-Difluorophenyl)-3-(4-[4-methyl-1,2,4-triazol-3-yl]phenyl)-1-(1,2,4-triazol-1-yl)butan-2-ol

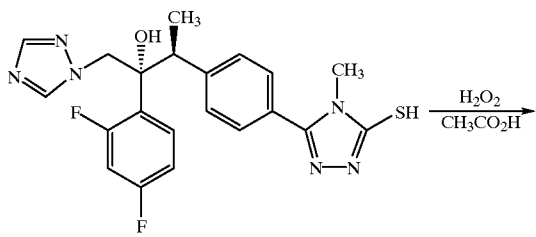

-continued

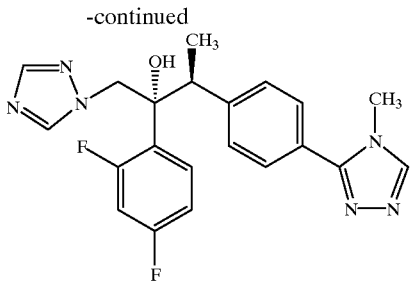

A solution of (2R,3S)-2-(2,4-difluorophenyl)-3-(4-[3-mercapto-4-methyl-1,2,4-triazol-5-yl]phenyl)-1-(1,2,4-triazol-1-yl)butan-2-ol (0.6 g, 1.4 mmol) in acetic acid (10 ml) was heated under reflux and treated with aqueous hydrogen peroxide (30%, 0.5 ml, 8 mmol) dropwise. After a further 0.5 hour at reflux, the mixture was cooled to room temperature and evaporated under reduced pressure. The residue was partitioned between ethyl acetate (20 ml) and saturated sodium bicarbonate solution (20 ml). The organic phase was washed with brine (20 ml), dried ($Na_2SO_4$) and evaporated under reduced pressure.

The residue was chromatographed on silica by elution with dichloromethane/methanol (96:4). Fractions containing the desired product were combined and evaporated under reduced pressure. The crude product was recrystallised from ethyl acetate/hexane to give the title compound (0.17 g, 30%) as a colourless solid, m.p. 118–120° C., $[\alpha]_D^{25}=-48°$ (c=0.1%, $CH_3OH$).

Analysis % Found: C, 60.14; H, 5.05; N, 20.00 $C_{21}H_{20}F_2N_6O$. ½$H_2O$ requires: C, 60.60; H, 4.90; N, 20.10

EXAMPLE 98

(2R,3S)-2-(2,4-Difluorophenyl)-3-(4-[3-methylpyrazol-4-yl]phenyl)-1-(1,2,4-triazol-1-yl)butan-2-ol

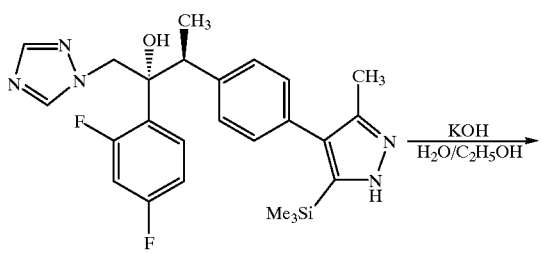

A solution of potassium hydroxide (0.26 g, 4.6 mmol) in water (2.8 ml) was added to a solution of (2R,3S)-2-(2,4-difluorophenyl)-3-(4-[3-methyl-5-trimethylsilylpyrazol-4-yl]phenyl)-1-(1,2,4-triazol-1-yl)butan-2-ol (0.22 g, 0.45 mmol) in ethanol (12 ml) and the mixture was heated under reflux for 4 hours. The cooled mixture was evaporated under reduced pressure and the residue partitioned between ethyl acetate (20 ml) and water (25 ml). The aqueous phase was further extracted with ethyl acetate (2×20 ml) and the combined organic layers were washed with brine (20 ml), dried(Na$_2$SO$_4$) and evaporated under reduced pressure.

The residue was chromatographed on silica by gradient elution with dichloromethane/methanol (100:0→96:4). Fractions containing the desired product were combined and evaporated under reduced pressure. The crude product was recrystallised from ethyl acetate/hexane to give the title compound (0.11 g, 56%) as a colourless solid, [α]$_D^{25}$=−50° (c=0.1%, CH$_3$OH).

Analysis % Found: C, 64.2; H, 4.9; N, 16.7 C$_{22}$H$_{22}$F$_2$N$_5$O. requires: C, 64.5; H, 5.2; N, 17.1

EXAMPLE 99

(2R,3S/2S,3R)-2-(2,4-Difluorophenyl-3-(5-[1,2,3-triazol-2-yl]pyridin-2-yl)-1-(1,2,4-triazol-1-yl)butan-2-ol

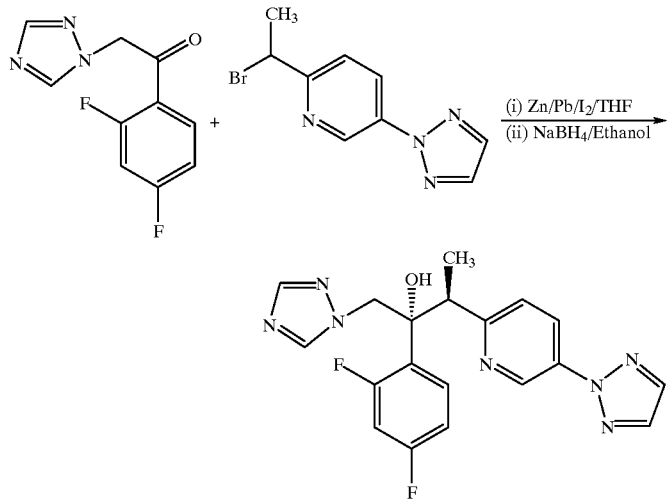

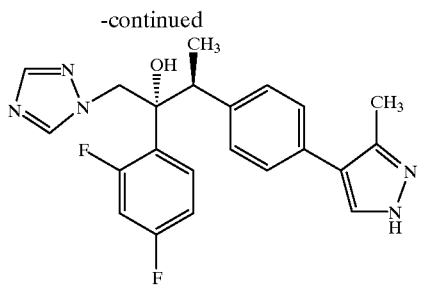

A solution of 2-(1-bromoethyl)-5-(1,2,3-triazol-2-yl)pyridine (0.75 g, 3 mmol) and 1-(2,4-difluorophenyl)-2-(1,2,4-triazol-1-yl)ethanone (0.66 g, 3 mmol) in THF (10 ml) was added dropwise to a stirred suspension of zinc (0.58 g, 9 mmol) and lead dust (0.03 g) in THF (8 ml) under a nitrogen atmosphere. Iodine (0.38 g, 1.5 mmol) was added in one portion and the mixture stirred at room temperature for 1 hour. A solution of ethylenediaminetetraacetic acid disodium salt (5%, 10 ml) was used to quench the reaction which was stirred for a further 0.5 hours at room temperature. Ethyl acetate (30 ml) and water (30 ml) were added and the mixture filtered through Hyflo™, to enable the layers to be separated. The organic phase was washed with brine (3×30 ml), dried (Na$_2$SO$_4$) and evaporated under reduced pressure.

The residue was chromatographed on silica by gradient elution with dichloromethane/ methanol (100:0→98:2).

Fractions containing the desired product were combined and evaporated under reduced pressure to give an oil, which was triturated with ether to give a colourless solid (0.42 g), which was characterised as a mixture of the desired product and the starting ethanone derivative.

The impure product was dissolved in ethanol (30 ml) and treated with sodium borohydride (0.05 g, 1.3 mmol). After 1 hour, the solvent was removed under reduced pressure and the residue partitioned between ethyl acetate (20 ml) and saturated sodium carbonate solution (30 ml). The aqueous phase was extracted with ethyl acetate (2×20 ml) and the combined organic layers were washed with brine (20 ml), dried($Na_2SO_4$) and evaporated under reduced pressure.

The residue was chromatographed on silica by gradient elution with dichloromethane/ methanol (100:0→99:1). Fractions containing the desired product were combined and evaporated under reduced pressure. The crude product was triturated with ether to give the title compound (0.12 g, 10%) as a colourless solid, m.p. 170–171° C.

Analysis % Found: C, 57.39; H, 4.10; N, 25.00 $C_{19}H_{17}F_2N_7O$. requires: C, 57.43; H, 4.31; N, 24.67

The following Preparations illustrate the preparation of certain of the starting materials used in the previous Examples:

PREPARATION 1

2-(2,4-Difluorophenyl)-3-(4-[1,2,3-triazol-2-yl] phenyl)-1-(1,2,4-triazol-1-yl)-3-buten-2-ol and 2-(2, 4-difluorophenyl)-3-(4-[1,2,3-triazol-1-yl]phenyl)-1-1,2,4-triazol-1-yl)-3-butan-2-ol

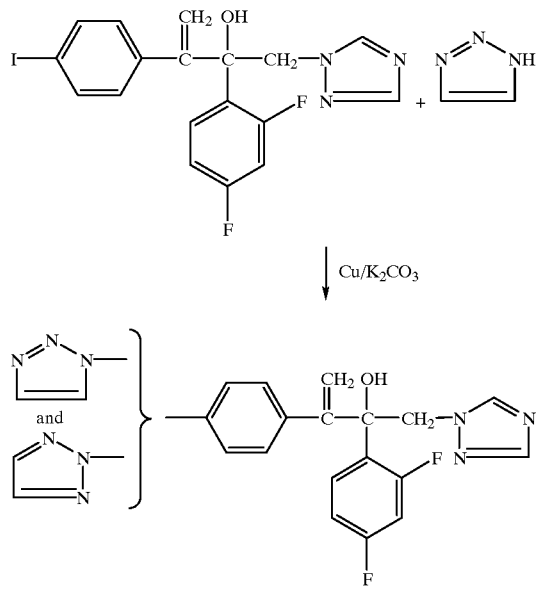

An intimate mixture of 2-(2,4-difluorophenyl)-3-(4-iodophenyl)-1-(1,2,4-triazol-1-yl)-3-buten-2-ol (2.0 g, 4.4 mmol-see Preparation 20), copper powder (0.6 g, 9.4 mmol), potassium carbonate (1.0 g, 7.3 mmol) and 1,2,3-triazole (2.6 g, 37.6 mmol) was stirred at 140° C. for 8 hours. The mixture was cooled to 100° C. and treated with a suspension of ethylenediaminetetraacetic acid disodium salt (10 g, 26.8 mmol) in water (100 ml). The suspension was basified with saturated sodium carbonate solution and was extracted with dichloromethane. The organic phase was dried ($MgSO_4$) and evaporated under reduced pressure. The residue was chromatographed on silica by elution with ethyl acetate/hexane (70:30). Fractions containing the faster-running spot were combined and evaporated under reduced pressure to give the 1,2,3-triazol-2-yl isomer (420 mg, 24%) as a colourless foam, which was characterised by $^1$H-N.M.R. spectroscopy (300 MHz, $CDCl_3$): δ=4.62 (d,1H); 4.97 (d,1H); 5.22 (s,1H); 5.32 (s,2H); 6.73 (m,2H); 7.42 (d,2H); 7.48 (m,1H); 7.79 (s,2H); 7.81 (d,2H); 7.96 (s,1H); 8.00 (s,1H) ppm.

Further elution of the column with ethyl acetate gave, after evaporation under reduced pressure, the major 1,2,3-triazol-1-yl isomer (650 mg, 37%). A sample of this product was recrystallised from ethyl acetate/hexane, m.p. 172–173° C.

Analysis %: Found: C, 61.12; H, 4.04; N, 21.14. $C_{20}H_{16}F_2N_6O$ requires: C, 60.91; H, 4.09; N, 21.31.

$^1$H-N.M.R. (300 MHz, $CDCl_3$): δ=4.62 (d,1H), 4.98 (d,1H), 5.34 (s,1H), 5.37 (s,2H), 6.76 (m,2H), 7.47 (d,2H), 7.49 (m,1H), 7.66 (d,2H), 7.83 (s,1H), 7.86 (s,2H), 7.98 (s,1H) ppm.

PREPARATIONS 2–7

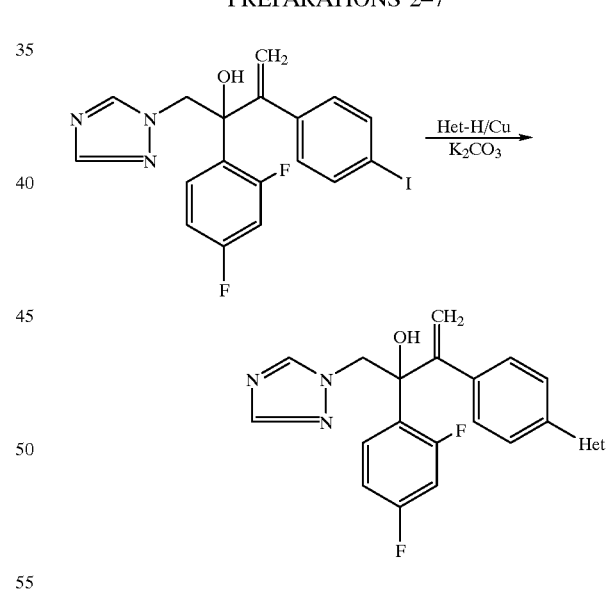

The following compounds were prepared similarly to the method of Preparation 1 using the appropriate heterocycle in place of 1,2,3-triazole.

| Prep No. | Het | m.p. (° C.) | Analysis % (Theoretical in brackets) C | H | N | Molecular formula | $^1$H-N.M.R. (300 MHz) δ[ppm] |
|---|---|---|---|---|---|---|---|
| 2 | 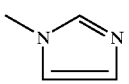 | 204–205 | 63.98 (64.12 | 4.31 4.36 | 17.79 17.80) | $C_{21}H_{17}F_2N_5O$ | |
| 3 | 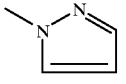 | Oil | | | | $C_{21}H_{17}F_2N_5O$ | 4.62(d, 1H), 4.96(d, 1H), 5.18 (brs, 1H), 5.31(s, 2H), 6.48(m, 1H), 6.73(m, 2H), 7.39(d, 2H), 7.48(m, 1H), 7.61(d, 2H), 7.72(d, 1H), 7.80(s, 1H), 7.83(s, 1H), 7.92(d, 1H). |
| 4 | 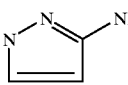 | Oil | | | | $C_{21}H_{18}F_2N_6O$ | 3.81(brs, 2H), 4.61(d, 1H), 4.95(d, 1H), 5.30(s, 2H), 6.64–6.80(m, 2H), 7.25 (m, 1H), 7.30(d, 2H), 7.44 (d, 2H), 7.45(m, 1H), 7.65 (d, 1H), 7.80(s, 1H), 7.81 (s, 1H). |
| 5 | 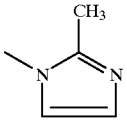 | Oil | | | | $C_{22}H_{19}F_2N_6O$ | 2.38(s, 3H), 4.61(d, 1H), 4.98(d, 1H), 5.28(s, 1H), 5.30(d, 2H), 6.70–6.80(m, 2H), 7.00(m, 2H), 7.21 (d, 2H), 7.40(d, 2H), 7.45 (m, 1H), 7.80(s, 1H), 7.82 (s, 1H). |
| 6 | 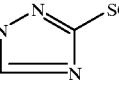 | Oil | | | | $C_{21}H_{18}F_2N_6OS$ | 2.63 (s, 3H), 4.60(d, 1H), 4.97(d, 1H), 5.24(s, 1H), 5.30(d, 2H), 6.70–6.80 (m, 2H), 7.41(d, 2H), 7.45 (m, 1H), 7.54(d, 2H), 7.80 (d, 2H), 8.43(s, 1H). |
| 7 | 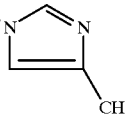 | 108–111 | 63.70 (63.45 | 4.91 4.81 | 16.36 16.81) | $C_{22}H_{19}F_2N_5O \cdot \tfrac{1}{2}H_2O$ | |

PREPARATION 8

3-[4-(3-Acetamidopyrazol-1-yl)phenyl]-2-(2,4-difluorophenyl)-1-(1,2,4-triazol-1-yl)-3-buten-2-ol

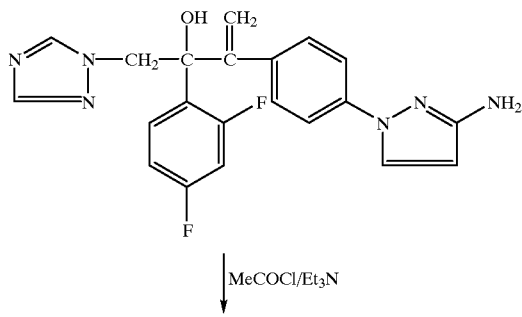

| MeCOCl/Et$_3$N

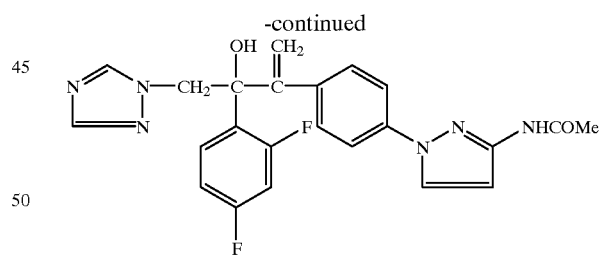

The product of Preparation 4 (0.7 g, 1.7 mmol) was dissolved in dichloromethane (15 ml) then treated with triethylamine (0.25 ml, 1.8 mmol) followed by acetyl chloride (0.13 ml, 1.8 mmol). The mixture was stirred at room temperature for 18 hours, diluted with dichloromethane (50 ml) then washed twice with water (20 ml). The organic phase was dried (MgSO$_4$) then evaporated under reduced pressure to give the title compound (0.7 g, 91%), which was characterised by $^1$H-N.M.R. spectroscopy.

$^1$H-N.M.R. (300 MHz, CDCl$_3$): δ=2.18 (t,3H), 4.63 (d,1H), 4.95 (d,1H), 5.29 (s,3H), 6.72 (m,2H), 6.93 (d,1H), 7.35 (d,2H), 7.42 (m,1H), 7.43 (d,2H), 7.79 (d,1H), 7.80 (s,1H), 7.82 (s,1H), 8.39 (s,1H) ppm.

PREPARATION 9

3-[4-(3-Methylsulphonamidopyrazol-1-yl)phenyl]-2-(2,4-difluorophenyl)-1-(1,2,4-triazol-1-yl)-3-buten-2-ol

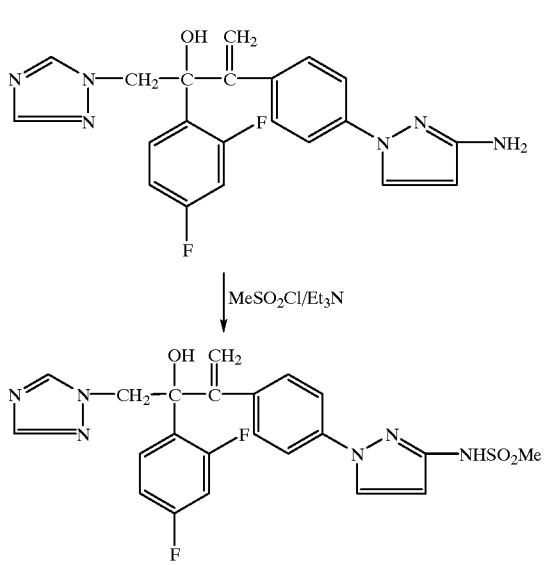

The title compound was prepared by the method of Preparation 8 using methanesulphonyl chloride in place of acetyl chloride. The crude product was triturated with ether to give the title compound, m.p. 130–140° C., which was characterised by $^1$H-N.M.R. $^1$H-N.M.R. (300 MHz, CDCl$_3$): δ=3.11 (s,3H), 4.62 (d,$_1$H), 4.97 (d,1H), 5.20–5.30 (m,3H), 6.42 (d,1H), 6.70–6.80 (m,2H), 6.99 (s,1H), 7.36 (d,2H), 7.42 (m,2H), 7.44 (d,2H), 7.80 (d,1H), 7.81 (s,1H), 7.84 (s,1H) ppm.

PREPARATION 10

2-(2,4-Difluorophenyl)-3-(4-[3-{3-methylureido}-pyrazol}-1-yl]phenyl)-1-(1,2,4-triazol-1-yl)-3-buten-2-ol

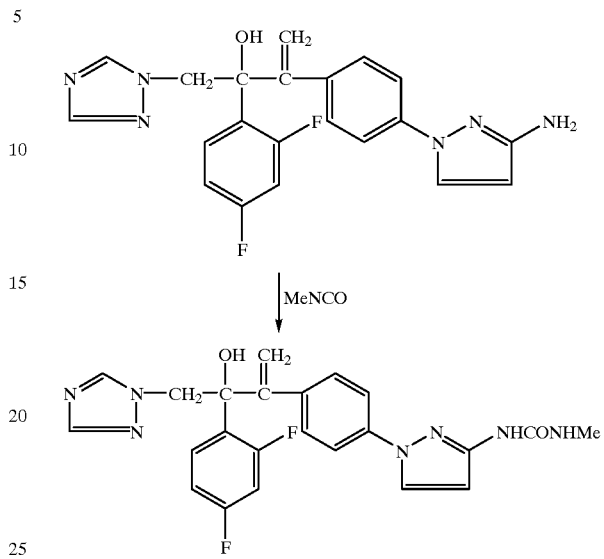

The product of Preparation 4 (0.7 g, 17 mmol) was dissolved in dichloromethane (15 ml) and treated with methyl isocyanate (0.15 ml, 2.5 mmol). The solution was stirred at room temperature for 18 hours and was then washed twice with water (20 ml), dried (MgSO$_4$) and evaporated under reduced pressure. The residue was purified by flash chromatography by elution with ethyl acetate/methanol (19:1). Fractions containing the desired product were combined and evaporated under reduced pressure to give the title compound (0.36 g, 45%).

Analysis %: Found: C, 58.12; H, 4.57; N, 20.49; C$_{23}$H$_{21}$F$_2$N$_7$O$_2$ requires: C, 58.22; H, 4.46; N, 20.66.

PREPARATION 11

2-(2,4-Difluorophenl)-3-(4-[1H-1,2,3-triazol-4-yl]phenyl)-1-(1,2,4-triazol-1-yl)-3-buten-2-ol

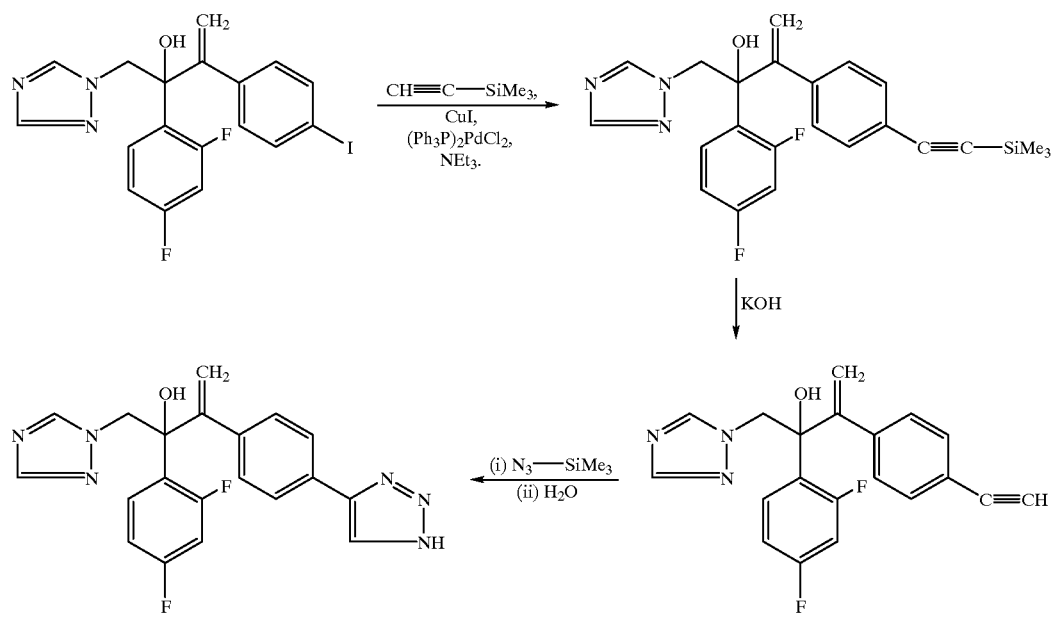

(i) A mixture of 2-(2,4-difluorophenyl)-3-(4-iodophenyl)-1-(1,2,4-triazol-1-yl)-3-buten-2-ol (7.0 g, 15.5 mmol-see Preparation 20), trimethylsilylacetylene (2.6 ml, 18.5 mmol), cuprous iodide (0.015 g, 0.15 mmol), bis(triphenylphosphine) palladium (II) dichloride (0.21 g, 0.3 mmol) and triethylamine (80 ml) was stirred at room temperature under a nitrogen atmosphere for 24 hours. Volatile materials were removed under reduced pressure and the residue was partitioned between dichloromethane (200 ml) and a solution of ethylenediaminetetraacetic acid (2 g) in water (100 ml). The organic phase was dried (MgSO$_4$) and evaporated under reduced pressure. The crude product was chromatographed on silica by elution with dichloromethane:methanol (95:5). Fractions containing the desired product were combined and evaporated under reduced pressure to give 2-(2,4-difluorophenyl)-3-(4-[trimethylsilylethynyl]phenyl)-1-(1,2,4-triazol-1-yl)-3-buten-2-ol (6.4 g, 98%) as a yellow foam which was characterised by $^1$H-N.M.R. spectroscopy, (300 MHz, CDCl$_3$): δ=0.22 (s,9H), 4.57 (d,1H), 4.89 (d,1H), 5.16 (s,1H), 5.26 (d,2H), 6.60–6.80 (m,2H), 7.21 (d,2H), 7.38 (d,2H), 7.42 (m,1H), 7.80 (s,2H) ppm.

(ii) The product from part (i) was dissolved in a mixture of aqueous potassium hydroxide (1M, 15 ml) and methanol (30 ml) and stirred at room temperature for 3 hours. The mixture was evaporated under reduced pressure and the residue was partitioned between dichloromethane (100 ml) and water (50 ml). The organic phase was dried (MgSO$_4$) and evaporated under reduced pressure. The residue was chromatographed on silica by elution with ethyl acetate/methanol. Fractions containing the desired product were combined and evaporated under reduced pressure to give 2-(2,4-difluorophenyl)-3-(4-ethynylphenyl)-1-(1,2,4-triazol-1-yl)-3-buten-2-ol (4.8 g, 93%) as a yellow foam which was characterised by $^1$H-N.M.R. spectroscopy (300 MHz, CDCl$_3$): δ=3.08 (s,1H), 4.58 (d,1H), 4.92 (d,1H), 5.19 (brs,1H), 5.29 (s,1H), 6.60–6.80 (m,2H), 7.24 (d,2H), 7.39 (d,2H), 7.41 (m,1H), 7.80 (s,1H), 7.82 (s,1H) ppm.

(iii) A sample of the product of part (ii) (2.5 g, 7 mmol) and azidotrimethyl silane (5 ml) was heated under reflux for 20 hours, additional azidotrimethyl silane (3×5 ml) being added at 6 hourly intervals. Excess azidotrimethylsilane was then removed under reduced pressure. The residue was dissolved in dichloromethane (50 ml); the resulting solution was washed with water (3×20 ml), dried (MgSO$_4$) and evaporated under reduced pressure. The crude product (2.5 g) was purified by chromatography on silica by gradient elution with dichloromethane:methanol (98:2, 96:4, 90:10).

Fractions containing the desired product were combined and evaporated under reduced pressure to give the title compound (1.0 g, 37%) as an orange foam, which was characterised by $^1$H-N.M.R. spectroscopy (300 MHz, CDCl$_3$): δ=4.62 (d,1H), 4.96 (d,1H), 5.30 (s,1H), 5.32 (d,2H), 6.70–6.80 (m,2H), 7.38 (d,2H), 7.46 (m,1H), 7.72 (d,2H), 7.80 (s,1H), 7.83 (s,1H), 7.94 (s,1H) ppm.

PREPARATION 12

2-(2,4-Difluorophenyl)-3-(4-[1-ethoxymethyl-1,2,4-triazol-5-yl]phenyl)-1-(1,2,4-triazol-1-yl)-3-buten-2-ol

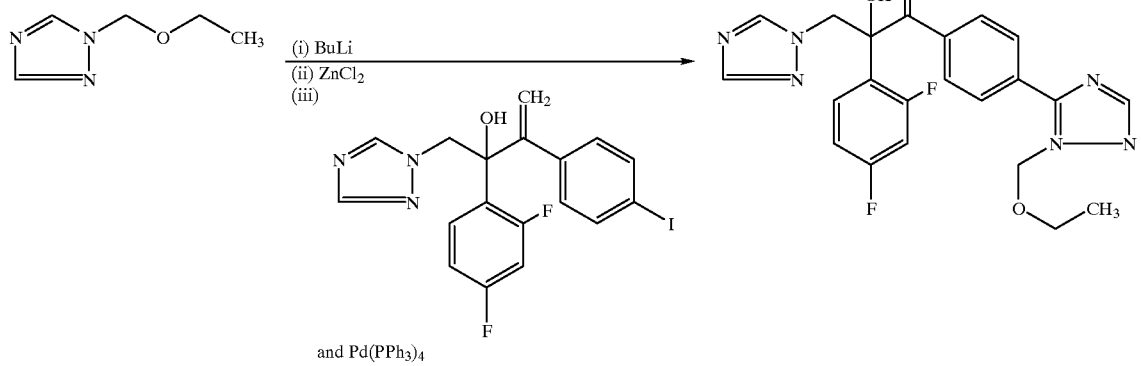

A solution of 1-ethoxymethyl-1,2,4-triazole (0.79 g, 6.2 mmol-see Preparation 27) in tetrahydrofuran (THF) (8 ml) was stirred under a nitrogen atmosphere at −70° C. before treatment with a solution of n-butyllithium in hexane (2.5M, 2.5 ml, 6.2 mmol) The mixture was stirred for 0.25 hours and treated with a solution of anhydrous zinc chloride (1.2 g, 9.3 mmol) in THF (8 ml), then was allowed to warm to room temperature. To this mixture was added tetrakis(triphenylphosphine)palladium (0) (0.06 g, 0.06 mmol) and 2-(2,4-difluorophenyl)-3-(4-iodophenyl)-1-(1,2,4-triazol-1-yl)-3-buten-2-ol (0.7 g, 1.5 mmol-see Preparation 20) and the mixture was heated under reflux for 4 hours. After being cooled, a suspension of ethylenediaminetetraacetic acid disodium salt (10 g, 27 mmol) was added, the mixture was adjusted to pH8 with saturated sodium carbonate solution and extracted with dichloromethane (2×100 ml). The combined extracts were dried (MgSO$_4$) and evaporated under reduced pressure. The residue was chromatographed on silica by gradient elution with dichloromethane:methanol (98:2, 97:3, 95:5). Fractions containing the desired product were combined, evaporated under reduced pressure and the residue was triturated with ether to afford the title compound (0.55 g, 78%) as a colourless solid, m.p. 160–162° C.

Analysis %: Found: C, 61.43; H, 4.82; N, 18.71. $C_{23}H_{22}F_2N_6O_2$ requires: C, 61.05; H, 4.90; N, 18.58.

PREPARATIONS 13–18

The following intermediates were prepared using the method of Preparation 12 from the appropriate 1-methyl or 1-ethoxymethylheterocycle and 2-(2,4-difluorophenyl)-3-(4-iodophenyl)-1-(1,2,4-triazol-1-yl)-3-buten-2-ol.

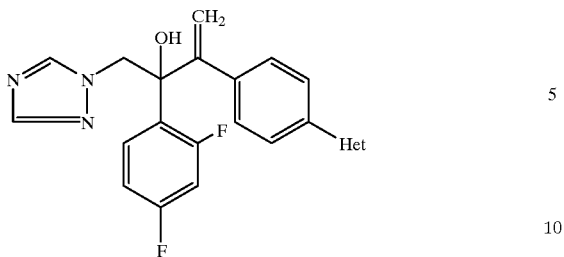

In the case of Preparation 17, the starting material was 4-bromo-1-ethoxymethylpyrazole.

| Prep No. | Het | m.p. (° C.) | Analysis % (Theoretical in brackets) C | H | N | Molecular formula | Optical rotation (where relevant) |
|---|---|---|---|---|---|---|---|
| 13 | (1-methyl-imidazol-2-yl with CH₃) | 248–250 | 64.33 (64.14 | 4.77 4.77 | 16.61 17.00) | $C_{22}H_{19}F_2N_5O \cdot \frac{1}{4}H_2O$ | |
| 14 | (triazole with OCH₂CH₃ and SCH₃) | — | 56.85 (56.80 | 4.85 4.97 | 16.47 16.56) | $C_{24}H_{24}F_2N_6O_2S \cdot \frac{1}{2}H_2O$ | |
| 15A | (triazole with OCH₂CH₃) (R, S) form | 153–155 | 60.86 (61.05 | 4.71 4.90 | 18.55 18.58) | $C_{23}H_{22}F_2N_6O_2$ | |
| 15B | (triazole with OCH₂CH₃) (R) form | 133–135 | 61.22 (61.05 | 4.84 4.90 | 18.37 (18.58) | $C_{23}H_{22}F_2N_6O_2$ | $[\alpha]_D^{25} = -44°$ |
| 15C | (triazole with OCH₂CH₃) (S) form | 133–135 | 61.06 (61.05 | 4.85 4.90 | 18.66 18.58) | $C_{23}H_{22}F_2N_6O_2$ | $[\alpha]_D^{25} = +47°$ |
| 16 | (imidazole with OCH₂CH₃) | 149–150 | 64.15 (63.85 | 4.95 5.14 | 15.65 15.51) | $C_{24}H_{23}F_2N_6O_2$ | |

-continued

| Prep No. | Het | m.p. (°C.) | Analysis % (Theoretical in brackets) C | H | N | Molecular formula | Optical rotation (where relevant) |
|---|---|---|---|---|---|---|---|
| 17 | 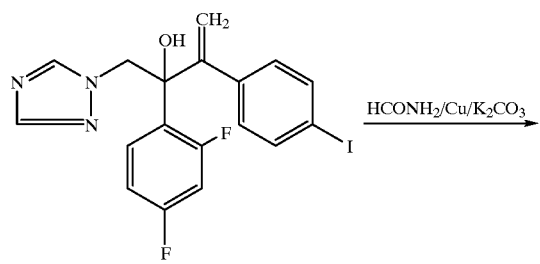 | 121–124 | 63.70 (63.85 | 5.04 5.14 | 15.39 15.51) | $C_{24}H_{23}F_2N_6O_2$ | |
| 18 | 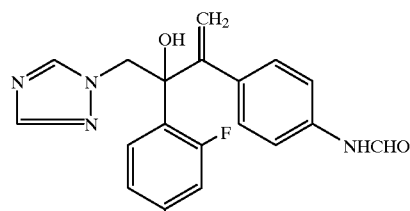 | Foam | 64.15 (64.38 | 4.79 4.86 | 12.16 12.51) | $C_{30}H_{27}F_2N_6O_2S$ | |

PREPARATION 19

2-(2,4-Difluorophenyl)-3-(4-formamidophenyl)-1-(1,2,4-triazol-1-yl)butan-2-ol

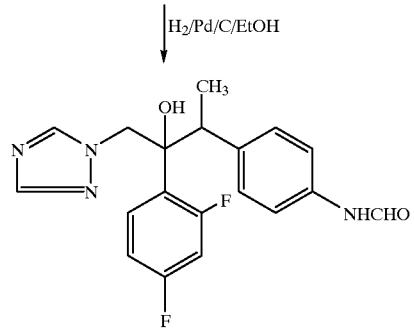

(i) An intimate mixture of 2-(2,4-difluorophenyl)-3-(4-iodophenyl)-1-(1,2,4-triazol-1-yl)-3-buten-2-ol (12 g, 26 mmol-see Preparation 20), formamide (18 ml, 0.25 mmol), copper (3.6 g, 57 mmol) and potassium carbonate (6.0 g, 43 mmol) was heated, with stirring, to 140° C. for 2 hours. The mixture was cooled to 100° C. and treated with a suspension of ethylenediaminetetracetic acid disodium salt (25 g, 6.7 mmol) in water (250 ml). After further cooling to room temperature, the mixture was extracted with dichloronithane (2×200 ml). The combined organic extracts were dried (MgSO₄) and evaporated under reduced pressure to give 2-(2,4-difluorophenyl)-3-(4-formamidophenyl)-1-(1,2,4-triazol-1-yl)but-3-en-2-ol (5.3 g, 55%), which was used crude in the next step.

(ii) The crude product from (i) in ethanol (150 ml) was hydrogenated over 10% palladium on charcoal (1.0 g) at 30 psi (2000 kPa) pressure for 5 hours. The mixture was filtered through "Arbocel" (Trade Mark) and the filtrate was evaporated under reduced pressure to give the title compound (4.4 g, 83%) as a foam. The product of this Preparation was used crude in Example 32.

PREPARATION 20

2-(2,4-Difluorophenyl)-3-(4-iodophenyl)-1-(1,2,4-triazol-1-yl)-3-buten-2-ol

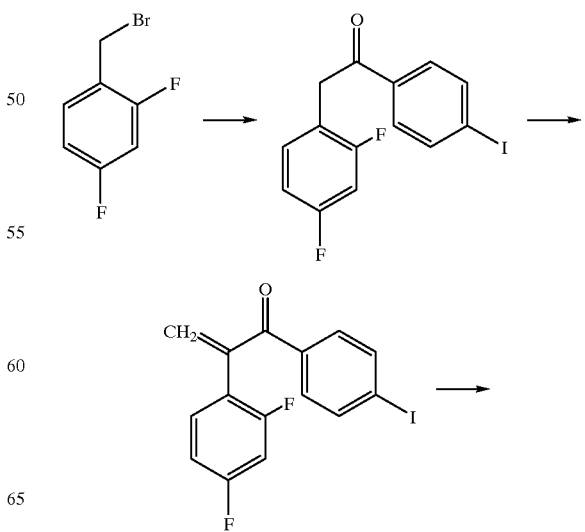

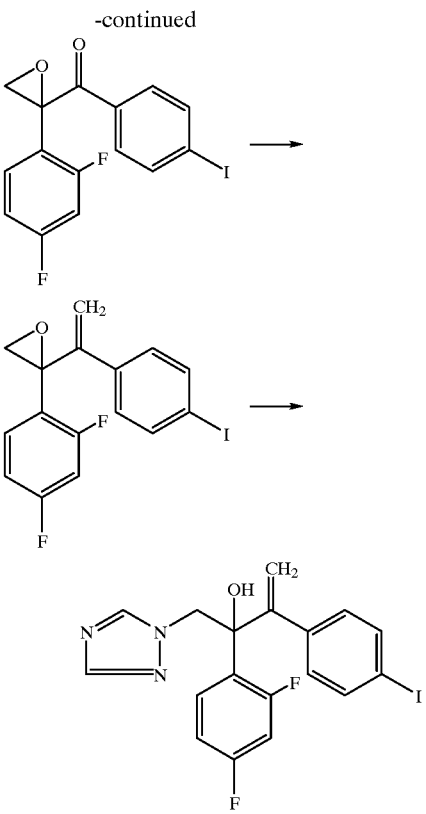

(i) 2-(2,4-Difluorophenyl)-1-(4-iodophenyl)ethanone 2,4-Difluorobenzyl bromide (23.7 ml, 0.114 mol) was added dropwise to a stirred mixture of magnesium turnings (8.1 g, 0.183 mol) in dry ether (300 ml) under nitrogen. The mixture was warmed initially until initiation of the reaction occurred, and thereafter said bromide was added at such a rate to maintain a gentle reflux. After 1 hour, the resulting solution of the Grignard reagent was added dropwise at −78° C. to a solution of O,N-dimethyl-4-iodobenzenehydroxamic acid (see Preparation 30) (45.71 g, 0.157 mol) in dry ether (300 ml), and the mixture was allowed to warm slowly to room temperature overnight. The mixture was partitioned between saturated aqueous ammonium chloride and ethyl acetate, and the organic solution was separated, dried (MgSO$_4$) and concentrated under reduced pressure, to give the title compound as a white solid, 38.71 g (69%), which was characterised by $^1$H-N.M.R. spectroscopy.

$^1$H-N.M.R. (300 MHz, CDCl$_3$): δ=4.23 (s,2H), 6.83 (m,2H), 7.17 (dt, J=7 and 8.5 Hz, 1H), 7.72 (d, J=9 Hz, 2H), 7.84 (d, J=9 Hz, 2H) ppm.

(ii) 2-(2,4-Difluorophenyl)-1-(4-iodophenyl)prop-2-enone

Bis(dimethylamino)methane (8.78 ml, 0.075 mol) was added dropwise to a stirred suspension of 2-(2,4-difluorophenyl)-1-(4-iodophenyl)ethanone (17.73 g, 0.0495 mol) in acetic anhydride (23.1 ml, 0.248 mol) at room temperature. There was an exothermic reaction, and the temperature of the mixture rose to 60° C. After the end of the addition, the mixture was stirred at room temperature for 35 minutes, and then iced water was added to hydrolyse the excess acetic anhydride. After a further 30 minutes, the product was extracted into ethyl acetate, and the extracts were washed with dilute hydrochloric acid, saturated aqueous sodium bicarbonate, dried (MgSO$_4$), and concentrated under reduced pressure, to give the title compound as a white solid (17.03 g, 93%), which was characterised by $^1$H-N.M.R. spectroscopy. $^1$H-N.M.R. (300 MHz, CDCl$_3$): δ=5.90 (s,1H), 6.14 (s,1H), 6.84 (ddd, J=12, 8 and 2 Hz), 6.95 (dt, J=2 and 8 Hz), 7.39 (dt, J=7 and 9 Hz, 1H), 7.59 (d, J=9 Hz, 2H), 7.83 (d, J=9 Hz, 2H) ppm.

(iii) 2-(2,4-Difluorophenyl)-2-(4-iodobenzoyl)oxirane

Benzyltrimethylammonium hydroxide (3.44 ml, 40% aqueous solution, 8.2 mmol) was added in one portion to a solution of 2-(2,4-difluorophenyl)-1-(4-iodophenyl)prop-2-enone (37.3 g, 100.8 mmol) and t-butylhydroperoxide (36.6 ml, 3M in trimethylpentane, 109 mmol) in toluene (550 ml) at room temperature. After 2 hours, the mixture was washed with water (2×500 ml), dried (MgSO$_4$) and concentrated under reduced pressure to give the title compound as a white solid (37.46 g, 96%), which was characterised by $^1$H-N.M.R. spectroscopy. $^1$H-N.M.R. (300 MHz, CDCl$_3$): δ=3.22 (d, J=5H, 1H), 3.42 (d, J=5 Hz, 1H), 6.80 (ddd, J=12, 8 and 2 Hz, 1H), 6.93 (dt, J=2 and 8 Hz, 1H), 7.47 (dt, J=7 and 9 Hz, 1H), 7.70 (d, J=9 Hz, 2H), 7.77 (d, J=9 Hz, 2H) ppm.

(iv) 2-(2,4-Difluorophenyl)-2-[1-(4-iodophenyl)ethenyl]oxirane n-Butyllithium (50 ml, 2.5M in hexane, 125 mmol) was added dropwise over 10 minutes to a stirred suspension of methyltriphenylphosphonium bromide (45.0 g, 126 mmol) in dry THF (600 ml) under nitrogen at −70° C. The mixture was allowed to warm to −20° C., over 20 minutes, then a solution of 2-(2,4-difluorophenyl)-2-(4-iodobenzoyl)oxirane (37.46 g, 97 mmol) in dry THF (200 ml) was added over 5 minutes. The mixture was allowed to warm to room temperature and stirred for 84 hours. 10% Aqueous ammonium chloride (500 ml) was added, and the mixture was concentrated under reduced pressure. The product was extracted into ethyl acetate and the combined extracts were dried (MgSO$_4$) and concentrated under reduced pressure. The solid residue was treated with boiling hexane (3×500 ml), and the residual solid discarded. The hexane solutions were combined, filtered through a short pad of silica gel, and concentrated under reduced pressure to give the title compound as a yellow oil (34.3 g, 92%), which was characterised by $^1$H-N.M.R. spectroscopy.

$^1$H-N.M.R. (300 MHz, CDCl$_3$): δ=3.13 (d, J=5 Hz, 1H), 3.17 (d, J=5 Hz, 1H), 5.45 (m,2H), 6.72 (m,1H), 6.80 (m,1H), 7.14 (d, J=9 Hz, 2H), 7.39 (dt, J=7 and 9 Hz, 1H), 7.60 (d, J=9 Hz, 2H) ppm.

(v) 2-(2,4-Difluorophenyl)-3-(4-iodophenyl)-1-(,2,4-triazol-1-yl)-3-buten-2-ol

Sodium 1,2,4-triazole (12.15 g, 133 mmol) was added to a solution of (2,4-difluorophenyl)-2-[1-(4-iodophenyl)ethenyl]oxirane (34.3 g, 89 mmol) in dry DMF (350 ml) under nitrogen at 70° C. The mixture was stirred for 5 hours, cooled, and the solvent removed under reduced pressure. The residue was partitioned between ether (800 ml) and water (2×500 ml). The organic solution was dried (MgSO$_4$), filtered, and silica gel (60–200μ, 75 g) was added. The ether was removed under reduced pressure and the residual solid was applied to the top of a silica gel column (40–60μ, 300 g) and the product was eluted using hexane and increasing amounts of ethyl acetate (0–75%). The product was obtained as a white foam, (23.8 g, 61%), which was characterised by ¹H-N.M.R. spectroscopy.

¹H-N.M.R. (300 MHZ, CDCl₃): δ=4.55 (d, J=15 Hz, 1H), 4.90 (d, J=15 Hz, 1H), 5.16 (s,1H), 5.25 (s,2H), 6.70 (m,2H), 7.03 (d, J=9 Hz, 2H), 7.43 (dt, J=7 and 9 Hz, 1H), 7.58 (d, J=9 Hz, 2H), 7.79 (s,1H), 7.80 (s,1H) ppm.

The title compound was resolved by chiral hplc using a "Chiralpak AD" (Trade Mark) column by elution with hexane/ethanol (95:5). Fractions containing each single enantiomer were combined and evaporated under reduced pressure, the residues were each chromatographed on silica by elution with dichloromethane/methanol (95:5), then triturated with ether.

Peak 1 (assigned as 2S stereochemistry) had m.p. 110–111° C. $[\alpha]_D^{25}$=+41°.

Peak 2 (assigned as 2R stereochemistry) had m.p. 111–112° C. $[\alpha]_D^{25}$=49°.

Analytical hplc indicated >99% ee for each enantiomer.

The (−) enantiomer had an analysis % as follows: Found: C, 47.52; H, 2.97; N, 9.09; $C_{18}H_{14}F_2IN_3O$ requires: C, 47.70; H, 3.11; N, 9.27.

The (+) enantiomer had an analysis % as follows: Found: C, 47.88; H, 3.02; N, 9.29; $C_{18}H_{14}F_2IN_3O$ requires: C, 47.70; H, 3.11; N, 9.27.

PREPARATION 21

2-(2,4-Difluorophenyl)-1-(1,2,4-triazol-1-yl)-3-[4-(1,2,4-triazol-1-yl)phenyl]-3-buten-2-ol

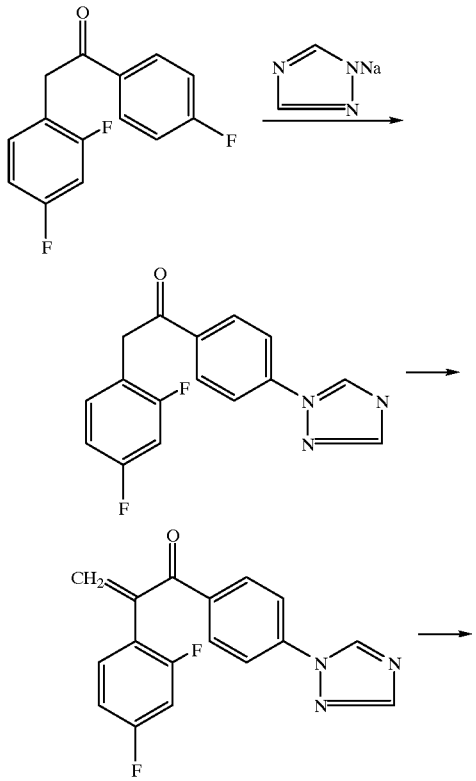

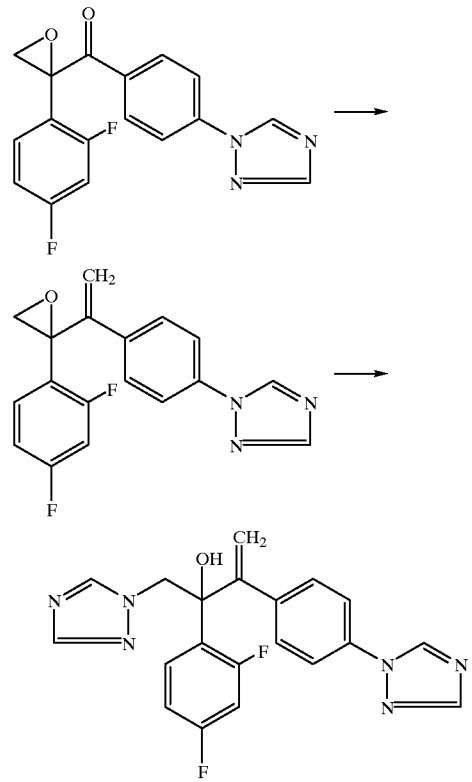

(i) 2-(2,4-Difluorophenyl)-1-[4-(1,2,4-triazol-1-yl)phenyl]-1-ethanone

A mixture of 2-(2,4-difluorophenyl)-1-(4-fluorophenyl)-1-ethanone (5.0 g, 20 mmol-see EP-A-0069442), sodium 1,2,4-triazole (2.18 g, 24 mmol) and N,N-dimethylacetamide (100 ml) was stirred at 100° C. for 18 hours. The mixture was diluted with xylene (300 ml) and concentrated under reduced pressure. The residue was dissolved in ethyl acetate (500 ml) and washed with water (3×50 ml). The organic solution was dried (MgSO₄) and concentrated under reduced pressure. Purification by flash chromatography (eluting with ethyl acetate:dichloromethane 1:1) gave a white solid (1.05 g, 18%), which was characterised by ¹H-N.M.R. spectroscopy.

¹H-N.M.R. (300 MHz, CDCl₃): δ=4.31 (s,2H), 6.88 (m,2H), 7.22 (m,1H), 7.84 (d, J=9 Hz, 2H), 8.14 (s,1H), 8.17 (d, J=9 Hz, 2H), 8.66 (s,1H) ppm.

(ii) 2-(2,4-Difluorophenyl)-1-[4-(1,2,4-triazol-1-yl)phenyl]prop-2-enone

By the method of Preparation 20(ii), 2-(2,4-difluorophenyl)-1-[4-(1,2,4-triazol-1-yl)phenyl]ethan-1-one (1.05 g, 3.51 mmol) was converted into 2-(2,4-difluorophenyl)-1-[4-(1,2,4-triazol-1-yl)phenyl]prop-2-enone (1.04 g, 92%), as a yellow solid, which was characterised by ¹H-N.M.R. spectroscopy.

¹H-N.M.R. (300 MHz, CDCl₃): δ=5.93 (s,1H), 6.16 (s,1H), 6.81 (m,1H), 6.93 (dt, J=2 and 8 Hz, 1H), 7.40 (dt, J=7 and 9 Hz, 1H), 7.79 (d, J=9 Hz, 2H), 8.02 (d, J=9 Hz, 2H), 8.13 (s,1H), 8.64 (s,1H) ppm.

(iii) 2-(2,4-Difluorophenyl)-2-[4-(1,2,4-triazol-1-yl)benzoyl]oxirane

By the method of Preparation 20(iii), 2-(2,4-difluorophenyl)-1-[4-(1,2,4-triazol-1-yl)-phenyl]prop-2- enone (1.04 g, 3.34 mmol) was converted into 2-(2,4-difluorophenyl)-2-[4-(1,2,4-triazol-1-yl)benzoyl]oxirane (1.01 g, 92%), as a white solid, which was characterised by $^1$H-N.M.R. spectroscopy.

$^1$H-N.M.R. (300 MHz, CDCl$_3$): δ=3.24 (d, J=4 Hz, 1H), 3.45 (d, J=4 Hz, 1H), 6.80 (ddd, J=2, 8 and 12 Hz, 1H), 6.95 (dt, J=2 and 8 Hz, 1H), 7.49 (dt, J=7 and 9 Hz, 1H), 7.75 (d, J=9 Hz, 2H), 8.12 (s,1H), 8.17 (d, J=9 Hz, 2H), 8.63 (s,1H) ppm.

(iv) 2-(2,4-Difluorophenyl)-2-[1-{4-(1,2,4-triazol-1-yl)phenyl}ethenyl]oxirane

By the method of Preparation 20(iv), 2-(2,4-difluorophenyl)-2-[4-(1,2,4-triazol-1-yl)-benzoyl]oxirane (1.00 g, 3.05 mmol) was converted into 2-(2,4-difluorophenyl)-2-[1-{4-(1,2,4-triazol-1-yl)phenyl}ethenyl]oxirane (570 mg, 57%), as a solid, after purification by flash chromatography (hexane:ethyl acetate 60:40), which was characterised by $^1$H-N.M.R. spectroscopy.

$^1$H-N.M.R. (300 MHz, CDCl$_3$): δ=3.19 (s,2H), 5.52 (m,2H), 6.72 (ddd, J=2, 8 and 12 Hz, 1H), 6.80 (dt, J=2 and 8 Hz, 1H), 7.42 (dt, J=7 and 9 Hz, 1H), 7.54 (d, J=9 Hz, 2H), 7.59 (d, J=9 Hz, 2H), 8.08 (s,1H), 8.53 (s,1H) ppm.

(v) 2-(2,4-Difluorophenyl)-1-(1,2,4-triazol-1-yl)-3-[4-(1,2,4-triazol-1-yl)phenyl]-3-buten-2-ol By the method of Preparation 20(v), 2-(2,4-difluorophenyl)-2-[1-{4-(1,2,4-triazol-1-yl)phenyl}ethenyl] oxirane (570 mg, 1.75 mmol) was treated with sodium 1,2,4-triazole in DMF (10 ml) at 70° C. for 8 hours, to give 2-(2,4-difluorophenyl)-1-(1,2,4-triazol-1-yl)-3-[4-(1,2,4-triazol-1-yl)phenyl]-3-buten-2-ol (620 mg, 89%), as a solid, which was characterised by $^1$H-N.M.R. spectroscopy.

$^1$H-N.M.R. (300 MHz, CDCl$_3$): δ=4.62 (d, J=13 Hz, 1H), 4.97 (d, J=13 Hz, 1H), 5.32 (m,3H), 6.74 (m,2H), 7.43 (d, J=9 Hz, 2H), 7.46 (m,1H), 7.57 (d, J=9 Hz, 2H), 7.81 (s,1H), 7.83 (s,1H), 8.09 (s,1H), 8.53 (s,$_1$H) ppm.

PREPARATION 22

2-(2,4-Difluorophenyl)-1-(1,2,4-triazol-1-yl)-3-[2-(1,2,4-triazol-1-yl)pyridin-5-yl]-3-buten-2-ol

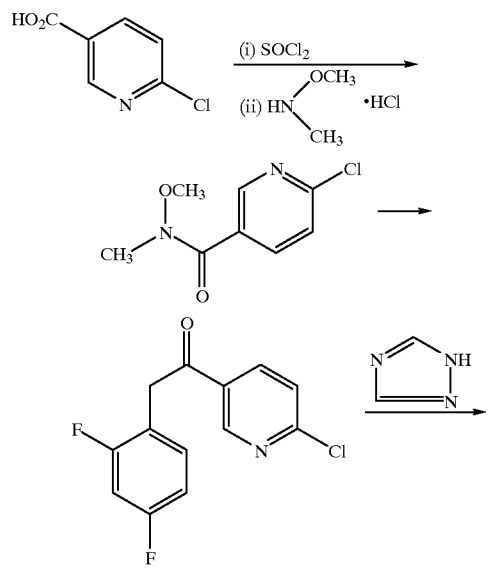

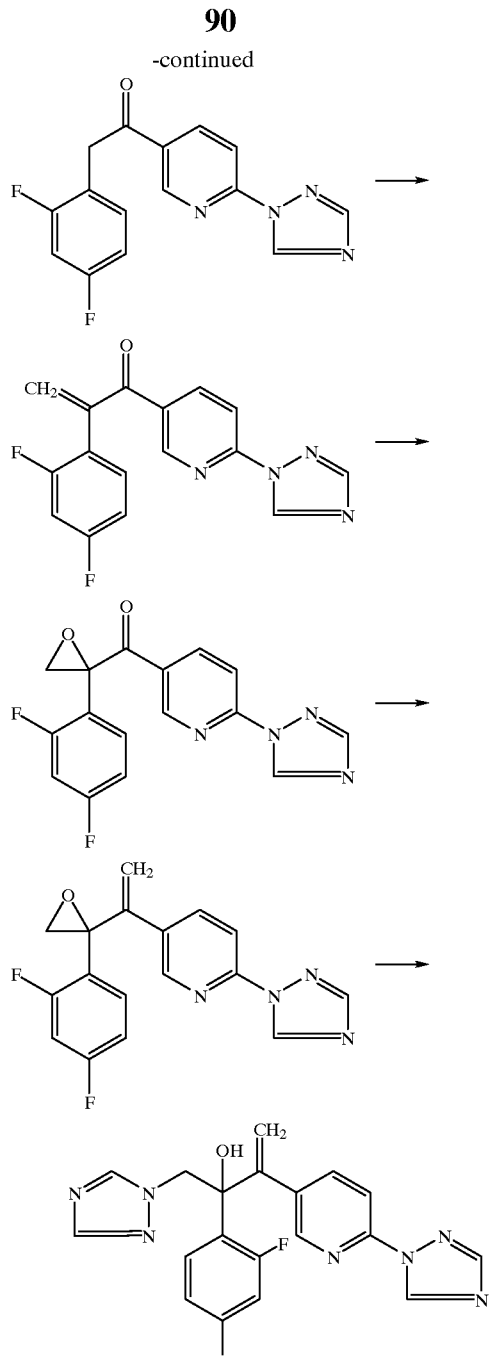

(i) O,N-Dimethyl-2-chloropyridine-5-hydroxamic acid

A suspension of 6-chloronicotinic acid (80 g, 0.5 mol) in thionyl chloride (400 ml) was heated under reflux for 3 hours to give a yellow solution. The mixture was concentrated under reduced pressure, the residue was dissolved in dichloromethane (600 ml) and treated with N,O-dimethylhydroxylamine hydrochloride (56.5 g, 0.58 mol). The suspension was cooled in ice then treated dropwise with triethylamine (220ml, 1.5 mol) and stirred for 1 hour at room temperature. The mixture was filtered, the filtrate was washed with aqueous sodium hydroxide (2N, 200 ml), dried over magnesium sulphate then concentrated under reduced pressure. The resulting liquid was distilled under reduced pressure to yield the title compound (90 g), b.p. 106–110° C. (0.5 mm Hg), which was characterised by $^1$H-N.M.R. spectroscopy.

$^1$H-N.M.R. (CDCl$_3$): δ=3.38(s), 3.56(s), 7.18(d), 8.00 (dd), 8.78(d).

(ii) 1-(2-Chloropyridin-5-yl)-2-(2,4-difluorophenyl) ethanone

The title product was prepared from the product of part (i) above by a similar method to that described in Preparation 20(i), m.p. 93–95° C.

Analysis %: Found: C, 58.01; H, 2.99; N, 5.17; C$_{13}$H$_8$ClF$_2$NO requires: C, 58.33; H, 3.01; N, 5.23.

(iii) 2-(2,4-Difluorophenyl)-1-[2-(1,2,4-triazol-1-yl) pyridin-5-yl ethanone

A mixture of the product of part (II) (1.06 g, 4 mmol), potassium carbonate (0.54 g, 4 mmol) and 1,2,4-triazole (0.34 g, 5 mmol) in DMF (10 ml) was heated to 70° C. for 4 hours. The mixture was cooled and partitioned between ethyl acetate (50 ml) and water (50 ml). The organic extract was washed with water (50 ml), dried (MgSO$_4$) and concentrated under reduced pressure. Trituration of the crude product with diethyl ether afforded the title compound, (0.3 g, 25%), m.p. 140–142° C.

Analysis %: Found: C, 60.31; H, 3.54; N, 18.17; C$_{15}$H$_{10}$F$_2$N$_4$O requires: C, 60.00; H, 3.36; N, 18.66.

(iv) 2-(2,4-Difluorophenyl)-1-[2-(1,2,4-triazol-1-yl) pyridin-5-yl]prop-2-enone

The title compound was prepared from the product of part (iii) by a similar method to that described in Preparation 20(ii) as a yellow solid (3.1 g, 79%), m.p. 136–138° C.

Analysis %: Found: C, 61.10; H, 3.25; N. 17.76; C$_{16}$H$_{10}$F$_2$N$_4$O requires: C, 61.54; H, 3.23; N,.17.94.

(v) 2-(2,4-Difluorophenl)-2-[2-(1,2,4-triazol-1-yl) pyridin-5-carbonyl]oxirane

The title compound was prepared from the product of part (iv) by a similar method to that described in Preparation 20(iii) as a yellow solid (3.1 g, 96%), m.p. 122–124° C.

Analysis %: Found: C, 58.86; H, 2.94; N, 16.92; C$_{16}$H$_{10}$F$_2$N$_4$O$_2$ requires: C, 58.54; H, 3.07; N, 17.07.

(vi) 2-(2,4-Difluorophenyl)-2-[1-(2-(1,2,4-triazol-1-yl)pyridin-5-yl)ethenyl]oxirane The title compound was prepared from the product of part (v) by a similar method to that described in Preparation 20(iv) as a colourless solid (2.8 g, 86%), m.p. 120–122° C.

Analysis %: Found: C, 62.87; H, 3.68; N, 17.18; C$_{17}$H$_{12}$F$_2$N$_4$O requires: C, 62.58; H, 3.71; N, 17.17.

(vii) 2-(2,4-Difluorophenyl)-1-(1,2,4-triazol-1-yl)-3-[2-(1,2,4-triazol-1-yl)pyridin-5-yl]-3-buten-2-ol The title compound was prepared from the product of part (vii) by a similar method to that described in Preparation 20(v) as a colourless solid (2.5 g, 75%) m.p. 153–156° C.

Analysis %: Found: C, 58.11; H, 3.46; N, 24.42; C$_9$H$_0$F$_2$N$_7$O requires: C, 57.72; H, 3.82; N, 24.80.

PREPARATION 23

(2R(3S)2S3R)-4-[2-(2,4-Difluorophenyl)-2-hydroxy-1-(1,2,4-tiazol-1-yl)but-3-yl] benzoylhdrazide

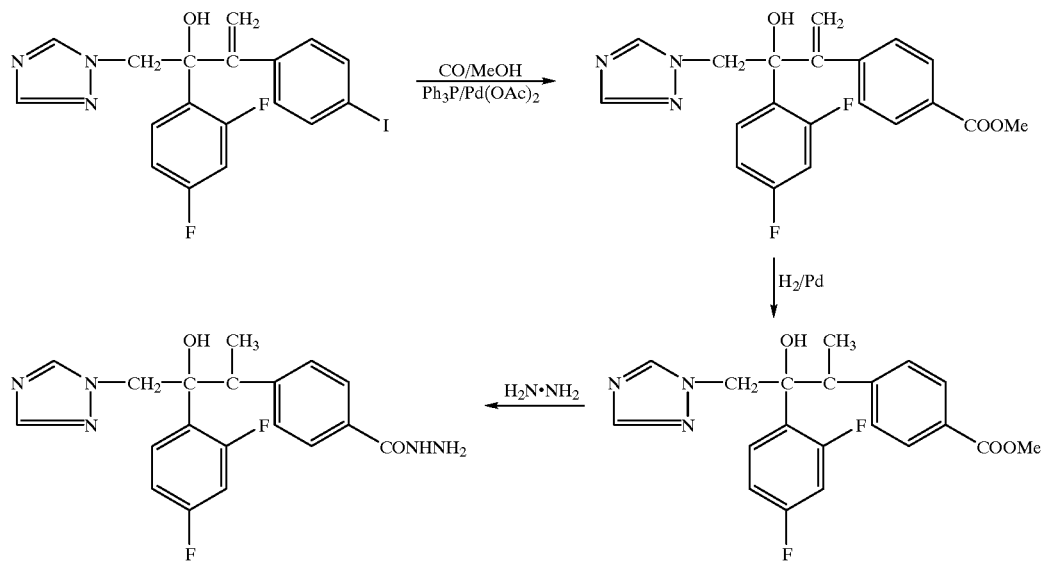

(i) 4-[2-(2,4-Difluorophenyl)-2-hydroxy-1-(1,2,4-triazol-1-yl)-3-buten-3-yl]benzoic acid methyl ester A mixture of 2-(2,4-difluorophenyl)-3-(4-iodophenyl)-1-(1,2,4-triazol-1-yl)-3-buten-2-ol (2.0 g, 4.4 mmol-see Preparation 20), palladium acetate (0.3 g), triphenylphosphine (0.23 g) and triethylamine (2 ml) was dissolved in methanol (20 ml). The mixture was heated to 100° C. under 50 psi (344.7 kPa) carbon monoxide for 4 hours, then partitioned between dichloromethane (50 ml) and water (20 ml). The organic phase was dried (MgSO$_4$) and evaporated under reduced pressure. The residue was purified by flash chromatography using gradient elution with dichloromethanel-methanol (100:0→98:2→96:4). Fractions containing the desired product were combined and evaporated under reduced pressure to give 4-[2-(2,4-difluorophenyl)-2-hydroxy-1-(1,2,4-triazol-1-yl)-3-buten-3-yl]benzoic acid methyl ester (1.7 g, 99%) as a foam. This intermediate was characterised by $^1$H-N.M.R. spectroscopy.

$^1$H-N.M.R. (300 MHz, CDCl$_3$): δ=3.90 (s,3H), 4.59 (d,1H), 4.92 (d,1H), 5.25 (s,1H), 5.31 (s,1H), 5.35 (s,1H), 6.70 (m,1H), 6.74 (m,1H), 7.36 (d,1H), 7.44 (q,1H), 7.80 (d,1H), 7.02 (s,1H), 7.94 (s,11H) ppmn.

(ii) (2R,3S/2S,3R)-4-[2-1,2,4-Difluorophenyl)-2-hydroxy-1-(1,2,4-triazol-1-yl)but-3-yl]benzoic acid methyl ester The product from part (i) was hydrogenated using the method of Example 1. The crude product was triturated with ether to give the title compound as a colourless solid.

Analysis %: Found: C, 61.90; H, 4.88; N, 10.79; C$_{20}$H$_0$F$_2$N$_0$O, requires: C, 62.01; H, 4.94; N, 10.85.

(iii) (2R,3S/2S,3R)-4-[2-(2,4-Difluorophenyl)-2-hydroxy-1-]1,2,4-triazol-1-yl)but-3-yl] benzoylhydrazide A solution of the product from part (II) (0.5 g, 1.3 mmol) in methanol (5 ml) was treated with hydrazine hydrate (0.25 ml, 8 mmol). The mixture was heated under reflux for 36 hours. The mixture was cooled to room temperature and was diluted with ether. The title compound (0.3 g, 60%) was collected by filtration and was characterised by $^1$H-N.M.R. spectroscopy (300 MHz, CDCl$_3$): δ=1.12 (d,3H), 3.38 (q,1H), 3.80 (d,1H), 4.13 (brs,2H), 4.79 (d,1H), 4.84 (s,$_1$H), 6.76 (m,2H), 7.37 (s,1H), 7.46 (m,1H), 7.60 (d,2H), 7.74 (m,4H) ppm.

PREPARATION 24

2-(2,4-Difluorophenyl)-3-(2-[imidazol-1-yl]pyridin-5-yl)-1-(1,2,4-triazoI-1-yl)-3-buten-2-ol

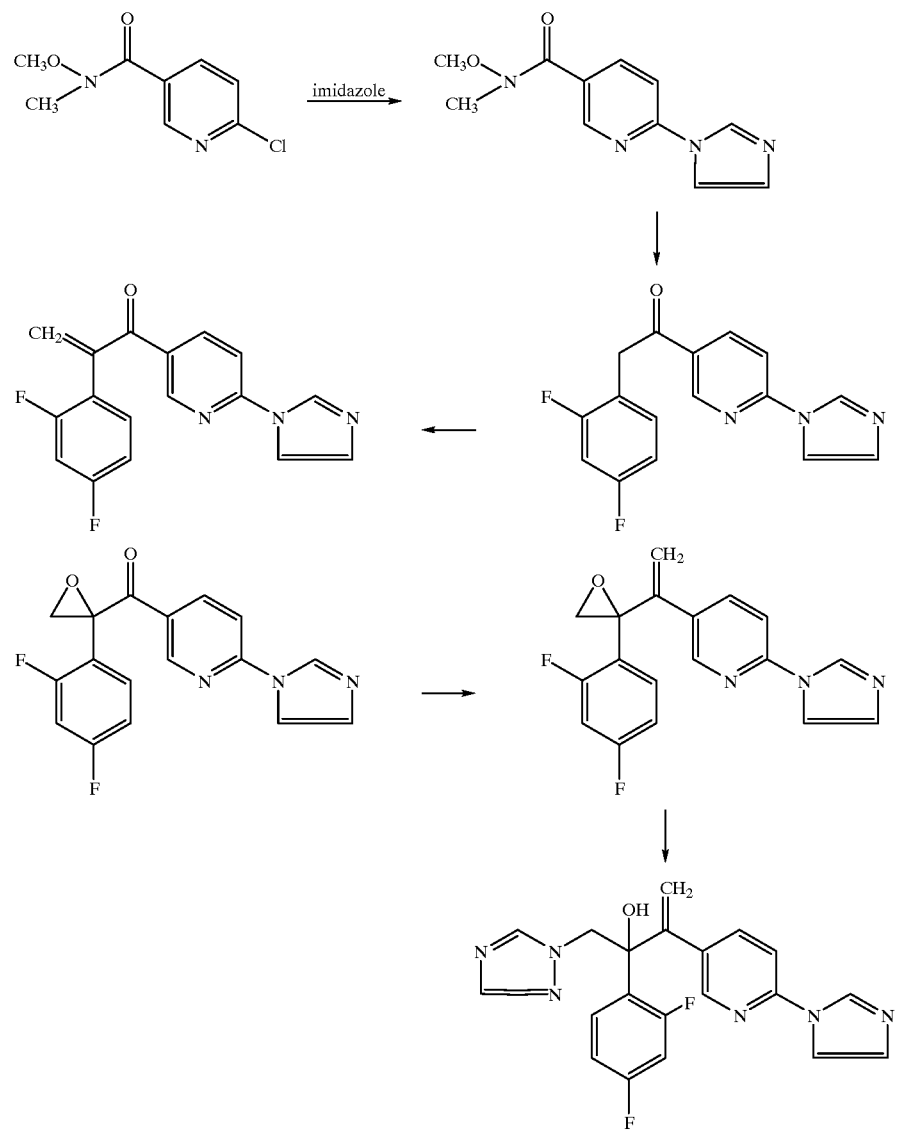

(i) O,N-Dimethyl-2-(imidazol-1-yl)pyridine-5-hydroxamic acid

A suspension of O,N-dimethyl-2-chloropyridine-5-hydroxamic acid (10.0 g, 50 mmol-see Preparation 22(i)), imidazole (4.1 g, 60 mmol) and potassium carbonate (6.9 g, 50 mmol) in N,N-dimethylacetamide (200 ml) was stirred at 140° C. for 24 hours. The mixture was evaporated under reduced pressure and the residue was partitioned between dichloromethane (100 ml) and water (100 ml). The organic phase was washed with water (100 ml) and brine (50 ml) then dried ($MgSO_4$) and evaporated under reduced pressure. The crude product was purified by column chromatography on silica using gradient elution with ethyl acetate/hexane (1:1,1:0). Fractions containing the desired product were combined and evaporated under reduced pressure to give the title compound (8.2 g, 71%) as an orange oil. A sample was triturated with ether to afford a colourless solid, m.p. 69–70° C.

Analysis %: Found: C, 56.94; H, 5.17; N, 23.77; $C_9H_2N_4O_2$ requires: C, 56.89; H, 5.21; N, 24.12.

(ii) 2-(2,4-Difluorophenyl)-1-(2-[imidazol-1-yl]pyridin-5-yl)ethanone

A solution of the product from part (i) (6.5 g, 28 mmol) in THF (100 ml) was stirred under a nitrogen atmosphere at −70° C. and was treated with a solution of 2,4-difluorobenzylmagnesium bromide [from 2,4-difluorobenzyl bromide (8.1 g, 39 mmol) and magnesium (1.0 g, 42 mmol) using the method of Preparation 20(i)] in ether (100 ml). The mixture was stirred at −70° C. for 0.5 hours and was allowed to warm to room temperature before the addition of dilute hydrochloric acid (2N, 100 ml). The layers were separated and the aqueous phase was extracted with dichloromethane (100 ml). The combined organic extracts were dried ($MgSO_4$) and evaporated under reduced pressure to yield the title compound as a pale yellow solid which was characterised by
$^1$H-N.M.R. spectroscopy (300 MHz, $CDCl_3$): δ=4.28 (s,2H), 6.85 (m,2H), 7.23 (m,2H), 7.48 (d,2H), 7.71 (s,$_1$H), 8.41 (dd,1H), 8.50 (s,1H), 9.11 (d,1H) ppm.

(iii) 2-(2,4-Difluorophenyl)-1-(2-[imidazol-1-yl]pyridin-5-yl)-2-propen-1-one The title compound was prepared from the product of part (ii) by a similar method to that described in Preparation 20(ii) as a yellow solid, m.p. 115–116° C.

Analysis %: Found: C, 65.43; H, 3.71; N, 13.54; $C_{17}H_{11}F_2N_3O$ requires: C, 65.59; H, 3.56; N, 13.50.

(iv) 2-(2,4-Difluorophenyl)-2-(2-[imidazol-1-yl]pyridin-5-carbonyl)oxirane

The title compound was prepared from the product of part (iii) by a similar method to that described in Preparation 20(iii) as an orange oil, which was characterised by $^1$H-N.M.R. spectroscopy (300 MHz, $CDCl_3$): δ=3.08 (d,1H), 3.41 (d,1H), 6.83 (m,1H), 6.97 (m,1H), 7.39 (d,1H), 7.49 (m,1H), 7.64 (s,1H), 8.39 (brs,1H), 8.40 (s,1H), 8.43 (dd,1H), 9.12 (d,1H) ppm.

(v) 2-(2,4-Difluorophenyl)-2-[1-[2-(imidazol-1-yl)pyridin-5-yl]ethenyl]oxirane The title compound was prepared from the product of part (iv) by a similar method to that described in Preparation 20(iv) as a yellow oil, which was used crude in the following step.

(vi) 2-(2,4-Difluorophenyl)-3-(2-[imidazol-1-yl]pyridin-5-yl)-1-(1,2,4-triazol-1-yl)-3-buten-2-ol The title compound was prepared by a similar method to that described in Preparation 20(v) as a colourless solid, m.p. 145–148° C.

| Analysis %: | | | |
|---|---|---|---|
| Found: | C, 60.37; | H, 3.55; | N, 19.92; |
| $C_{20}H_{16}F_2N_6O$.1/5 ethyl acetate requires: | C, 60.63; | H, 4.31; | N, 20.40. |

The presence of ethyl acetate was confirmed by $^1$H-N.M.R. spectroscopy (300 MHz, $CDCl_3$): δ=1.29 (t, part H), 2.02 (s, part H), 4.12 (q, part H), 4.64 (d,1H), 5.09 (d,1H), 5.40 (s,1H), 5.45 (s,1H), 5.52 (s,$_1$H), 6.75 (m,2H), 7.20 (s,1H), 7.23 (d,1H), 7.45 (m,1H), 7.61 (s,1H), 7.84 (dd,1H), 7.85 (s,1H), 7.88 (s,1H), 8.35 (s,1H), 8.37 (d,1H) ppm.

PREPARATION 25

2-(2,4-Difluorophenyl)-3-(4-[5-amino-1,3,4-thiadiazol-2-yl]phenyl)-1-(1,2,4-triazol-1-yl)-3-buten-2-ol

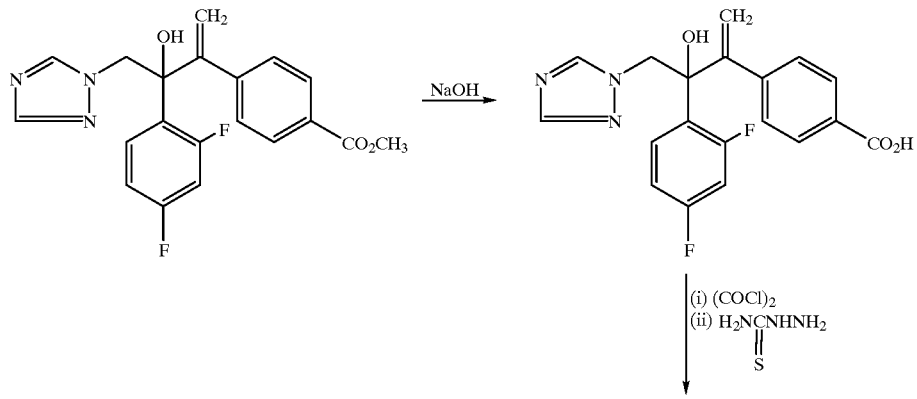

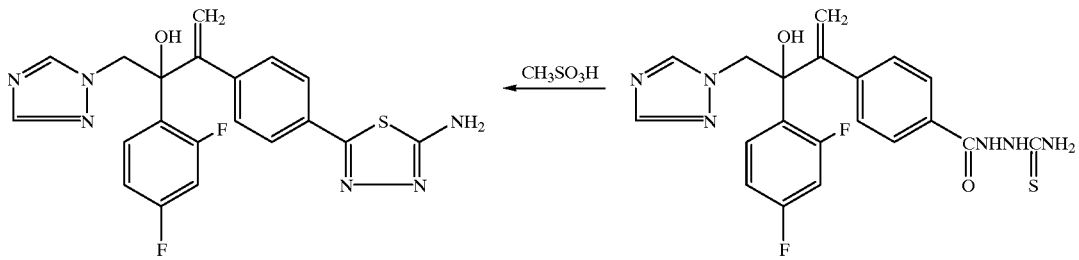

(i) A solution of 4-(2-[2,4-difluorophenyl]-2-hydroxy-1-(1,2,4-triazol-1-yl)-3-buten-3-yl) benzoic acid methyl ester (see Preparation 23 part (i)) (3.44 g, 9 mmol) in a mixture of methanol (50 ml) and aqueous sodium hydroxide (2M, 9 ml, 18 mmol) was heated under reflux for 3 hours. The cooled solution was evaporated under reduced pressure and the residue was dissolved in water (30 ml). The aqueous solution was extracted with ethyl acetate (3×30 ml) before acidification with hydrochloric acid (2M). The aqueous phase was further extracted with ethyl acetate (3×30 ml). The combined organic extracts were washed with brine (3×20 ml), dried ($Na_2SO_4$) and evaporated under reduced pressure to yield 4-{2-[2,4-difluorophenyl]-2-hydroxy-1-(1,2,4-triazol-1-yl)-3-buten-3-yl} benzoic acid (3.2 g, 96%). Recrystallisation of a sample from ethyl acetate/hexane/methanol afforded an off-white solid, m.p. 189–190° C.

Analysis %: Found: C, 61.41; H, 3.99; N, 11.21; $C_{13}H_{15}F_2N_3O_3$ requires: C, 61.45; H, 4.07; N, 11.32.

(ii) A sample of the product from part (i) (370 mg, 1 mmol) was suspended in dichloromethane (15 ml), and was treated with dimethylformamide (1 drop) and oxalyl chloride (0.1 ml, 1.1 mmol). The solution was stirred at room temperature for 1 hour and was evaporated under reduced pressure. The residue. was dissolved in dichloromethane (15 ml) and treated with thiosemicarbazide (0.1 g, 1 mmol) and sodium carbonate (0.1 g, 1 mmol). The mixture was stirred at room temperature for 24 hours then filtered. The filtrate was absorbed onto silica and chromatographed by gradient elution with ethyl acetate/methanol (97:3, 95:5, 94:6). Fractions containing the desired product were combined and evaporated under reduced pressure. The crude product was triturated with ether to give 4-{2-[2,4-difluorophenyl]-2-hydroxy-1-[1,2,4-triazol-1-yl]-3-buten-3-yl}benzoylthiosemicarbazide (0.21 g, 47%) as a colourless solid which was characterised by $^1$H-N.M.R. spectroscopy (300 MHz, DMSO). δ=4.83 (Abq, 2H), 5.32 (s,1H), 5.58 (s,1H), 6.57 (s,1H), 6.77 (m,1H), 6.98 (m,1H), 7.11 (m, 1H), 7.30 (d,2H), 7.58 (brs, 1H), 7.60 (s,1H), 7.62 (d,2H), 7.78 (brs, 1H), 8.19 (s, 1H), 9.22 (brs, 1H), 10.22 (brs,1H) ppm.

(iii) The product from part (II) (0.15 g, 0.3 mmol) in toluene (8 ml) was treated with methanesulphonic acid (0.04 ml) and the mixture was heated under reflux for 3 hours. The solvents were removed under reduced pressure and the residue was partitioned between saturated sodium carbonate solution (10 ml) and dichloromethanelmethanol (10:1, 50 ml). The organic layer was dried ($MgSO_4$) and evaporated under reduced pressure. The crude product was purified by column chromatography on silica using gradient elution with dichloromethane/methanol (98:2, 95:5, 90:10). Fractions containing the desired product were combined and evaporated under reduced pressure to give a foam which yielded the title compound (0.03 g, 20%) upon trituration with ether as a colourless solid, m.p. 118–121° C.

Analysis %: Found: C, 55.98; H, 3.59; N, 19.40; $C_{20}H_{16}F_2N_6OS$ requires: C, 56.33; H, 3.78; N, 19.71.

PREPARATION 26

1-Ethoxymethyl-3-methylthio-1,2,4-triazole

A suspension of 5-methylthio-1,2,4-triazole (6.19, 53 mmol) and chloromethyl ethyl ether (2.5 ml, 26 mmol) in toluene (40 ml) was stirred at room temperature for 24 hours. The mixture was filtered and the filtrate was evaporated under reduced pressure. The residue was chromatographed on silica by elution with ethyl acetate/diethylamine (95:5) to yield the title compound (1.1 g, 27%), as a colourless oil, which was characterised by $^1$H-N.M.R. spectroscopy (300 MHz, $CDCl_3$): δ=1.20 (t,3H), 2.59 (s,3H), 3.60 (q,2H), 5.41 (s,2H), 8.17 (s,1H) ppm.

PREPARATION 27

1-Ethoxymethyl-1,2,4-triazole

The title compound was prepared from 1,2,4-triazole by a similar method to that of Preparation 26, as a colouriess oil, which was characterised by $^1$H-N.M.R. spectroscopy (300 MHz, $CDCl_3$): δ=1.23 (t,3H), 3.58 (q,2H), 5.50 (s,2H), 8.01 (s,1H), 8.28 (s,1H) ppm.

PREPARATION 28

4-Bromo-1-ethoxymethylpyrazole

The title compound was prepared from 4-bromopyrazole by a similar method to that of Preparation 26, as a colourless oil, which was characterised by $^1$H-N.M.R. spectroscopy (300 MHz, $CDCl_3$): δ=1.17 (t,3H), 3.50 (q,2H), 5.39 (s,2H), 7.49 (s,1H), 7.69 (s,1H) ppm.

PREPARATION 29

1-Ethoxymethyl-1,2.3-triazole

The title compound was prepared from 1,2,3-triazole by a similar method to that of Preparation 26, as a colourless oil, which was characterised by $^1$H-N.M.R. spectroscopy (300 MHz, $CDCl_3$): 6 1.19 (t,3H), 3.56 (q,2H), 5.71 (s,2H), 7.77 (ABq, 2H) ppm.

PREPARATION 30

O,N-Dimethyl-4-iodobenzenehydroxamic acid

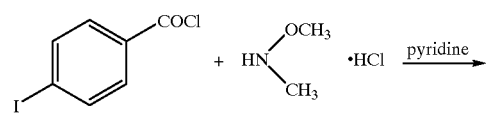

-continued

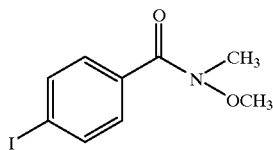

A solution of pyridine (104 g, 1.32 mol) in dichloromethane (150 ml) was added dropwise to a suspension of 4-iodobenzoyl chloride (251 g, 0.94 mol) and N,O-dimethylhydroxylamine hydrochloride (97 g, 0.94 mol) in dichloromethane (850 ml) at 0° C. The mixture was allowed to warm to room temperature and was stirred for 18 hours. The solution was evaporated under reduced pressure, the residue was dissolved in ethyl acetate (IL), and was then washed with dilute hydrochloric acid (2N, 3×400 ml) and saturated sodium bicarbonate solution (300 ml) and dried ($Na_2SO_4$). The organic extract was evaporated under reduced pressure. The residue was purified by distillation to yield the title product (241 g, 93%), as a yellow oil b.p. 130° C. (0. Imm Hg), which was characterised by $^1$H-N.M.R. spectroscopy (300 MHz, $CDCl_3$): δ=3.32 (s,3H), 3.50 (s,3H), 7.40 (d,2H), 7.72 (d,2H) ppm.

PREPARATION 31

(2R,3S/2S,3R)-2-(2,4-Difluorophenyl)-3-(4-[5-mercapto-1,3,4-oxadiazol-2-yl]lphenyl)-1-(1,2,4-triazol-1-yl)butan-2-ol

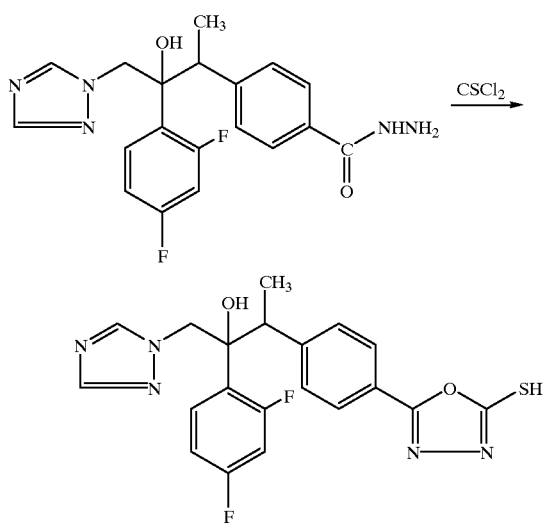

A solution of (2R,3S/2S,3R)-4-(2-[2,4-difluorophenyl]-2-hydroxy-1-(1,2,4-triazol-1-yl)but-3-yl)benzoylhydrazide (0.77 g, 2 mmol-see Preparation 23) in 1,4-dioxan (15 ml) was treated with thiophosgene (0.25 g, 2,4 mmol) and the mixture was stirred at room temperature for 18 hours. The mixture was evaporated under reduced pressure and the residue was partitioned between a mixture of ethyl acetate/methanol (95:5, 50 ml) and water (30 ml), after adjustment to pH5 with dilute ammonium hydroxide solution. The organic phase was dried ($MgSO_4$) and evaporated under reduced pressure. The crude product was purified by column chromatography on silica by gradient elution with dichloromethane/methanol (100:0, 98:2, 95:5, 90:10). Fractions containing the desired product were combined and evaporated under reduced pressure to yield the title compound (0.5 g, 60%), as a pale yellow foam, which was characterised by $^1$H-N.M.R. (300 MHz, DMSOd.): δ=1.06 (d,3H), 3.59 (q,1H), 3.93 (d,1H), 4.80 (d,$_1$H), 5.75 (s,1H), 6.92 (m,1H), 7.10–7.30 (m,2H), 7.60 (s,1H), 7.62 (d,2H), 7.88 (d,2H), 8.15 (s,1H), 14.70 (brs,1H) ppm.

PREPARATION 32

(2R,3S/2S,3R)-4-[2-(2,4-Difluorophenyl)-2-hydroxy-1-(1,2,4-triazol-1-yl)but-3-yl]benzoic acid A solution of (2R,3S/2S,3R)-4-[2-(2,4-difluorophenyl)-2-hydroxy-1-(1,2,4-triazol-1-yl)but-3-yl] benzoic acid methyl ester (0.8 g, 2 mmol-see Preparation 23(ii)) in a mixture of aqueous sodium hydroxide (2N, 2.1 ml, 4 mmol) and methanol (20 ml) was heated under reflux for 3 hours. The mixture was evaporated under reduced pressure and the residue was partitioned between ethyl acetate (50 ml) and dilute hydrochloric acid (5 ml). The organic phase was dried ($MgSO_4$) and evaporated under reduced pressure. The crude product was triturated with ether to yield the title compound (0.72 g, 94%), m.p. 243–245° C., as a colourless solid.

Analysis %: Found: C, 60.84; H, 4.56; N, 11.02; $C_{19}H_{17}F_2N_3O_3$ requires: C, 61.12; H, 4.59; N, 11.26.

PREPARATION 33

5-(2,5-Dimethylpyrrol-1-yl)-2-ethylpyridine

A mixture of 2-ethylpyridin-5-amine (3.2 g, 26 mmol), 2,5-hexanedione (3.0 g, 26 mmol) and acetic acid (1 ml) in toluene (50 ml) was heated under reflux for 24 hours. The solvent was removed under reduced pressure and the residue was partitioned between dichloromethane (50 ml) and water (20 ml). The aqueous phase was basified with aqueous sodium hydroxide (2M) and then extracted with dichloromethane (50 ml). The extract was dried ($MgSO_4$) and evaporated under reduced pressure. The crude product was purified by column chromatography on silica by elution with dichloromethane/methanol (95:5) to give the title compound (2.38 g, 46%) as a colourless oil, which was characterised by $^1$H-N.M.R. spectroscopy.

$^1$H-N.M.R. (300 MHz, $CDCl_3$): δ=1.38 (t,3H), 2.02 (s,6H), 2.91 (q,2H), 5.93 (s,2H), 7.25 (d,1H), 7.44 (dd,1H), 8.41 (d,1H) ppm.

PREPARATION 34

4-Ethyl-6-(1,2,4-triazol-1-yl)pyrimidine

A mixture of 4-chloro-6-ethylpyrimidine (1.42 g, 10 mmol) and 1H-1,2,4-triazole (1.4 g, 20 mmol) was heated to 120° C. with stirring to give a yellow oil, which deposited an orange solid. The mixture was maintained at 120° C. for 0.2 hours, cooled to 70° C. and dissolved in methanol (10 ml). The solution was diluted with dichloromethane (50 ml) and was washed with saturated sodium bicarbonate solution (20 ml). The aqueous phase was extracted with dichloromethane (2×20 ml) and the combined organic layers were dried ($MgSO_4$) and evaporated under reduced pressure. The crude product was purified by column chromatography on silica by elution with ethyl acetate to give the title compound (1.44 g, 82%) as a yellow solid, m.p. 75–76° C., which was characterised by $^1$H-N.M.R. spectroscopy.

$^1$H-N.M.R. ($CDCl_3$): δ=1.38 (t,3H), 2.90 (q,2H), 7.74 (s,1H), 8.13 (s,1H), 8.98 (s,1H), 9.22 (s,1H) ppm.

PREPARATION 35

2-(2-Chlorophenyl)-3-(4-iodophenyl)-1-(1,2,4-triazol-1-yl)-3-buten-2-ol

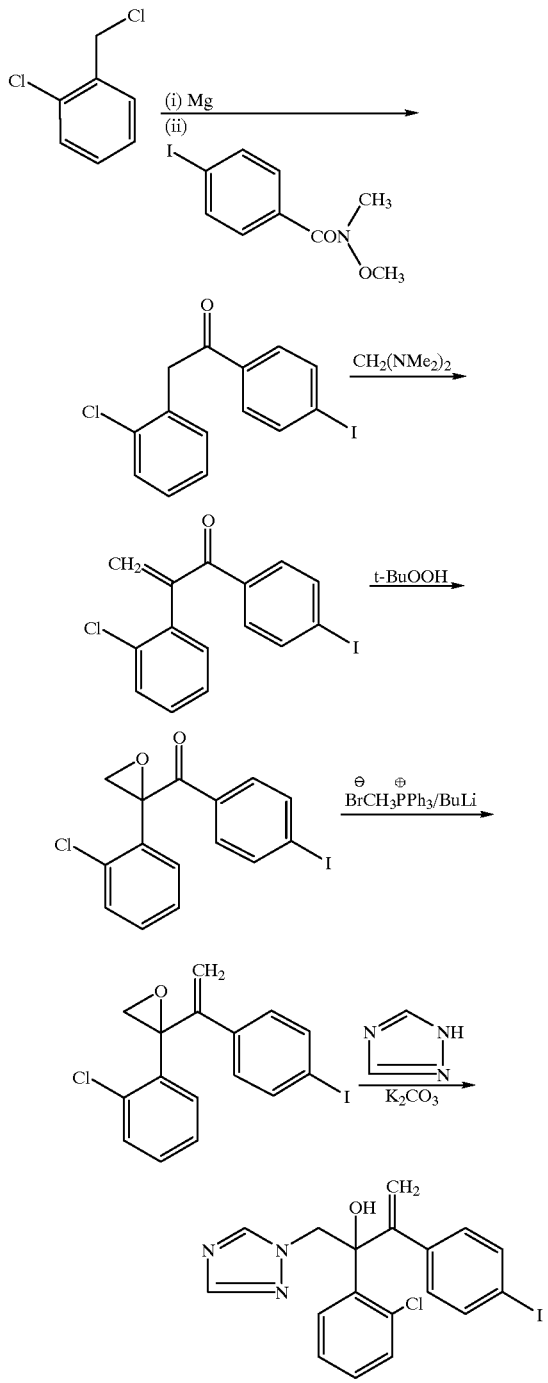

(i) 2-(2-Chlorophenyl)-1-(4-iodophenyl)ethanone

The title compound was prepared from α,2-dichlorotoluene and O,N-dimethyl-4-iodobenzenehydroxamic acid (see Preparation 30) by a similar method to that of Preparation 20(i) as a colourless solid, m.p. 105–106° C., which was characterised by $^1$H-N.M.R. spectroscopy.

$^1$H-N.M.R. (CDCl$_3$, 300 MHz): δ=4.40 (s,2H), 7.27 (s,3H), 7.42 (m,1H), 7.74 (d,2H), 7.82 (d,2H) ppm.

(ii) 2-(2-Chlorophenyl)-1-(4-iodophenyl)prop-2-enone

The title compound was prepared using the product of part (i) by a similar method to Preparation 20(ii) as a colourless solid, m.p. 101–103° C., which was characterised by $^1$H-N.M.R. spectroscopy.

$^1$H-N.M.R. (300 MHz, CDCl$_3$): δ=5.93 (s,1H), 6.10 (s,1H), 7.20–7.40 (m,4H), 7.65 (d,2H), 7.83 (d,2H) ppm.

(iii) 2-(2-Chlorophenyl)-2-(4-iodobenzoyl)oxirane

The title compound was prepared from the product of part (ii) by a similar method to Preparation 20(iii), as a colourless foam, which was characterised by $^1$H-N.M.R. spectroscopy.

$^1$H-N.M.R. (300 MHz, CDCl$_3$): δ=3.22 (d,1H), 3.49 (d,1H), 7.20–7.40 (m,3H), 7.57 (m,1H), 7.71 (d,2H), 7.77 (d,2H) ppm.

(iv) 2-(2-Chlorophenyl)-2-(1-[4-iodophenyl]ethenyl)oxirane

The title compound was prepared from the product of part (iii) by a similar method to Preparation 20(iv), as a colourless oil, which was characterised by $^1$H-N.M.R. spectroscopy.

$^1$H-N.M.R. (300 MHz, CDCl$_3$): δ=3.01 (d,1H), 3.12 (d,1H), 5.26 (s,1H), 5.32 (s,1H), 7.17 (d,2H), 7.25 (m,2H), 7.34 (m,1H), 7.52 (m,1H), 7.62 (d,2H) ppm.

(v) 2-(2-Chlorophenyl)-3-(4-iodophenyl)-1-(1,2,4-triazol-1-yl)-3-buten-2-ol

The title compound was prepared from the product of part (iv) by a similar method to Preparation 20(v), as a colourless solid, m.p. 128–130° C.

Analysis %: Found: C, 47.89; H, 3.16; N, 9.23; C$_{18}$H$_0$ClN$_3$O requires: C, 47.84; H, 3.33; N, 9.30.

PREPARATION 36

2-(2-Fluorolphenyl)-3-(4-iodophenyl)-1-(1,2,4-triazol-1-yl)-3-buten-2-ol

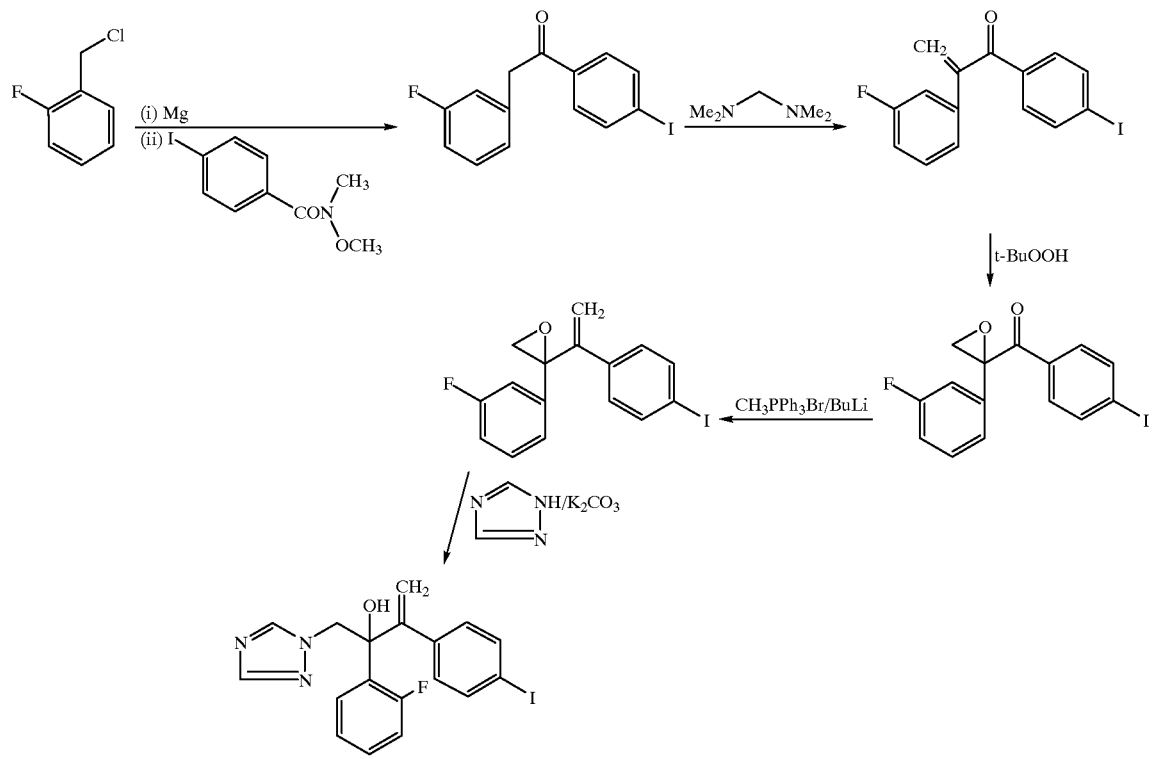

(i) 2-(2-Fluorophenyl)-1-(4-iodophenyl)ethanone

The product was prepared from 2-fluorobenzyl bromide and O,N-dimethyl-4-iodobenzenehydroxamic acid (see Preparation 30) by a similar method to Preparation 20(i) as a colourless solid, m.p. 112–114° C.

Analysis %: Found: C, 49.91; H, 2.98; $C_{14}H_{10}FIO$ requires: C, 49.56; H, 2.95.

(ii) 2-(2-Fluorophenyl)-1-(4-iodophenyl)prop-2-enone

The title compound was prepared using the product of part(i) by a similar method to Preparation 20(ii) as a colourless solid, m.p. 92–93° C.

Analysis %:
Found: C, 51.64; H, 2.73;
$C_{155}H_{10}FIO$ requires: C, 51.28; H, 2.85.

(iii) 2-(2-Fluorophenyl)-2-(4-iodobenzoyl)oxirane

The title compound was prepared from the product of part (ii) by a similar method to Preparation 20(iii), as a colourless solid, m.p. 75–76° C.

Analysis %: Found: C, 49.11; H, 2.77; $C_{15}H_{10}FIO_2$ requires: C, 49.05; H, 2.72.

(iv) 2-(2-Fluorophenyl)-2-(1-[4-iodophenyl]ethenyl)oxirane

The title compound was prepared from the product of part (iii) by a similar method to Preparation 20(iv), as a colouriess oil, which was characterised by $^1$H-N.M.R. spectroscopy.

$^1$H-N.M.R. (300 MHz, CDCl$_3$): δ=3.16 (ABq,2H), 5.45 (d,2H), 6.98 (t,1H), 7.09 (t,1H), 7.16 (d,2H), 7.23 (m,1H), 7.45 (m,1H), 7.60 (d,2H) ppm.

(v) 2-(2-Fluorophenyl)-3-(4-iodophenyl)-1-(1,2,4-triazol-1-yl)-3-buten-2-ol

The title compound was prepared from the product of part (iv) by a similar method to Preparation 20(v), as a colourless solid, m.p. 117–118° C.

Analysis %: Found: C, 50.35; H, 3.52; N, 9.66; $C_{18}H_{15}FIN_3O$ requires: C, 49.77; H, 3.46; N, 9.70.

$^1$H-N.M.R. (300 MHz, CDCl$_3$): δ=4.58 (d,1H), 4.96 (d,1H), 5.1 (brs,1H), 5.24 (d,2H), 6.90–7.05 (m,2H), 7.05 (d,2H), 7.22 (m,1H), 7.45 (m,1H), 7.63 (d,2H), 7.80 (s,1H), 7.82 (s,1H) ppm.

PREPARATIONS 37–39

The following compounds were prepared using the method of Preparation 1 or Preparation 12, as specified in the Table.

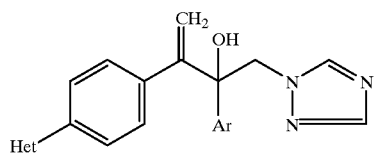

| Prep No. | Het | Ar | m.p. (° C.) | Analysis % (Theoretical in brackets) | | | Molecular formula | Method of Preparation No. |
|---|---|---|---|---|---|---|---|---|
| | | | | C | H | N | | |
| 37 | N-methylimidazole | 2-Cl-phenyl | Foam | Characterised by N.M.R. data - see below | | | $C_{21}H_{18}ClN_6O$ | 1 |
| 38 | 1-(ethoxymethyl)-5-methyl-1,2,3-triazole | 2-Cl-phenyl | 104–105 | 61.01 (61.26 | 4.94 5.10 | 18.70 18.65) | $C_{23}H_{23}ClN_6O_2$ | 12 |
| 39 | 1-(ethoxymethyl)-5-methyl-1,2,3-triazole | 2-F-phenyl | 142–145° | 63.55 (63.59 | 5.47 5.30 | 19.39 19.35) | $C_{23}H_{23}FN_6O_2$ | 12 |

PREPARATION 37

$^1$H—N.M.R. (300 MHz, CDCl$_3$): δ = 4.64 (d); 4.69 (d); 4.77 (d); 5.30 (s); 5.44 (s); 5.46 (d); 5.57 (s); 7.00–7.90 (multiplets) ppm. [N.B. compound was micture of rotamers].

PREPARATION 40 (Alternative to Preparation 29)

1-Ethoxymethyl-1 2,3-triazole

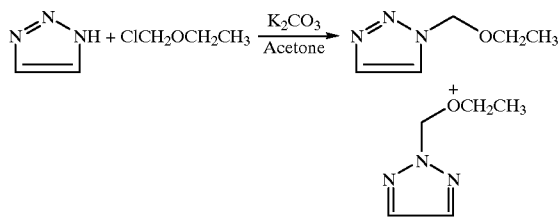

Chloromethyl ethyl ether (125 g, 1.3 mole) was added dropwise over 1½ hours to a mechanically stirred suspension of 1,2,3-triazole (91.4 g, 1.3 mole) and potassium carbonate (183 g, 1.3 mole) in acetone (1500 ml) with ice-bath cooling. The mixture was allowed to warm to room temperature and was stirred for 18 hours. The solvent was removed under resolved pressure and the residue was dissolved in water (1 L). The aqueous solution was extracted with dichloromethane (3×300 ml) and the organic extracts were combined. The dichloromethane solution was washed with brine (3×300 ml) and the organic phase was dried (Na$_2$SO$_4$) and evaporated under reduced pressure to give a pale yellow oil.

The oil was distilled under reduced pressure to give, initially, 2-ethoxymethyl-1,2,3-triazole (57 g, 34%) b.p. <90° C. (3 mm Hg).

$^1$H-N.M.R. (300 MHz, CDCl$_3$): δ=1.17 (t,3H), 3.60 (q,2H), 5.70 (s,2H), 7.70 (s,2H) ppm.

Analysis %: Found: C, 47.36; H, 7.23; N, 32.62; C$_5$H$_9$N$_3$O requires: C, 47.19; H, 7.14; N, 33.05.

Further distillation gave the title compound (73 g, 43%), b.p. 92–93° C., (3 mm Hg). $^1$H-N.M.R. (300 MHz, CDCl$_3$): δ=1.15 (t,3H), 3.56 (q,2H), 5.70 (s,2H), 7.77 (s,1H), 7.79 (s,1H) ppm.

Analysis %: Found: C, 46.30; H, 7.52; N, 33.29; C$_5$H$_9$N$_3$O requires: C, 47.19; H, 7.14; N, 33.05.

PREPARATION 41

2-(2,4-Difluorophenyl)-1-(1,2,4-triazol-1-yl)-3-[4-(1-{2-methoxyethoxymethyl}-1,2,3-triazol-5-yl) phenyl]-3-buten-2-ol The following compound was prepared similarly to the method of Preparation 12 using the triazole from Preparation 42:

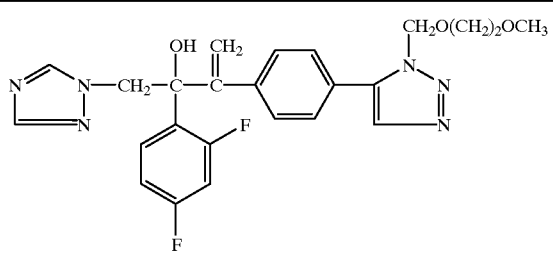

m.p. 124–127° C.

Analysis %:

| Found: | C, 59.79; H, 4.86; N, 17.14; |
|---|---|
| Calculated for $C_{24}H_{24}F_2N_6O_3$: | C, 59.75; H, 5.01; N, 17.42. |

Analysis %: Found: C, 59.79; H, 4.86; N. 17.14; Calculated for $C_{24}H_{24}F_2N_6O_3$: C, 59.75; H, 5.01; N, 17.42.

PREPARATION 42

1-(2-Methoxyethoxymethyl)-1,2,3-triazole

The title compound was prepared from 1,2,3-triazole and 2-methoxyethoxymethyl chloride, by a similar method to that of Preparation 40, as a colourless oil which was characterised by $^1$H-NMR spectroscopy (300 MHz, CDCl$_3$): δ=3.31(s,3H), 3.46(m,2H), 3.62(m,2H), 5.77(s,2H), 7.73(s,1H),7.75(s,1H) ppm.

PREPARATION 43

2-(2,4-Difluorophenyl)-3-(4-[1-benzyl-1,2,3-triazol-5-yl]phenyl)-1-(1,2,4-triazol-1-yl)-3-buten-2-of The following compound was prepared as a racemate similarly to the method of Preparation 12 using 1-benzyl-1,2,3-triazole, m.p. 105–108° C.

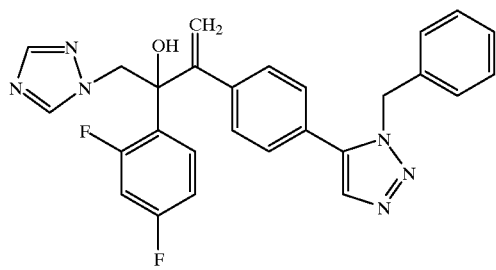

Analysis %

| Found: | C,66.69; | H,4.59; | N,17.56 |
|---|---|---|---|
| $C_{27}H_{22}F_2N_6O$ requires | C,66.93; | H,4.58; | N,17.35 |

PREPARATION 44

2-(2,4-Difluorophenyl)-3-(4-[1-[2-hydroxyethoxymethyl]-1,2,3-triazol-5-yl]phenyl)-1-(1,2,4-triazol-1-yl)-3-buten-2-ol The following compound was prepared similarly to the method of Preparation 12 using the triazole from Preparation 45:

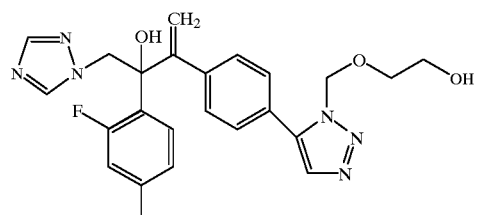

The product was isolated as a colourless oil, which was characterised by NMR. $^1$H-NMR (300 MHz, CDCl$_3$): δ=3.6–3.8(m,4H), 4.64(d,1H), 4.96(d,1H), 5.26(s,1H), 5.34(s,2H), 5.74(s,1H),5.78(s,1H),7.4–7.55(m,5H),7.7–7.8(m,2H),7.80(m,3H)ppm.

PREPARATION 45

1-Hydroxyethoxymethyl-1,2,3-triazole

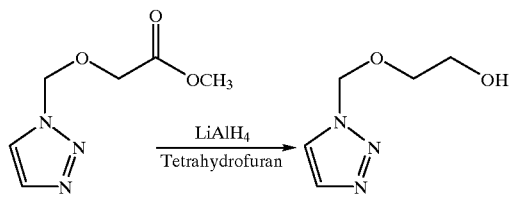

A solution of methyl 1,2,3-triazol-1-ylmethoxyacetate (0.72 g, 4.2 mmol-see Preparation 46) in tetrahydrofuran (10 ml) was added dropwise to a suspension of lithium aluminium hydride (0.16 g, 4.2 mmol) at 0° C. The mixture was allowed to warm to room temperature overnight and was quenched by addition of water (0.32 ml) followed by aqueous sodium hydroxide solution (15%,0.32 ml) and water (1 ml). After a further hour, the supernatant liquid was collected by filtration and the residue was washed with tetrahydrofuran (10 ml). The filtrate was evaporated under reduced pressure and the residue was purified by flash chromatography on silica by elution with dichloromethanelmethanol (19:1). Fractions containing the desired product were combined and evaporated under reduced pressure to yield the title compound as an oil (0.30 g, 52%) which was characterised by NMR.

$^1$H-NMR (300 MHz, CDCl$_3$): δ=2.05(t,1H), 3.6–3.8(m, 4H), 5.80(s,2H), 7.78(s,2H) ppm.

PREPARATION 46

Methyl 1,2,3-triazol-1-ylmethoxyacetate

The title compound was prepared from 1,2,3-triazole and methyl chloromethoxyacetate by a similar method to that of Preparation 40 as a colourless oil which was characterised by NMR. $^1$H-NMR (300 MHz, CDCl$_3$): δ=3.76 (s,3H), 4.16 (s,2H), 5.84 (s,2H), 7.80 (d,2H) ppm.

PREPARATION 47

(2R,3S/2S,3R)-2-(2,4-Difluorophenyl)-3-(4-propanoylphenyl)-1-(1,2,4-triazol-1-yl)butan-2-ol

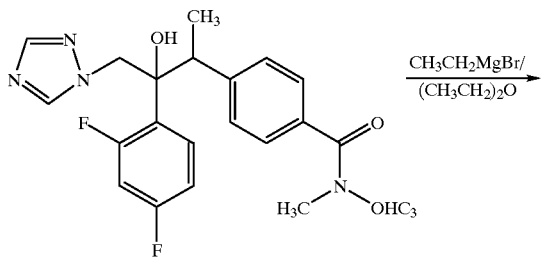

A solution of N,O-dimethyl-4-(2-[2,4-difluorophenyl]-2-hydroxy-1-(1,2,4-triazol-1-yl)but-3-yl benzenehydroxamic acid (2.70 g, 6.5 mmol-see Preparation 49) in dry ether (100 ml) was cooled to 0° C. under a nitrogen atmosphere and treated with a solution of ethyl magnesium bromide in ether (1.0M, 15 ml, 15 mmol). The solution was stirred at room temperature for 18 hours, quenched with saturated ammonium chloride solution (50 ml) and the layers were separated. The aqueous phase was extracted with ethyl acetate (100 ml) and the organic layers were combined, dried (MgSO$_4$) and evaporated under reduced pressure. The residue was purified by flash chromatography on silica by gradient elution with ethyl acetate/hexane (1:1, 1:0). Fractions containing the desired product were combined and evaporated under reduced pressure to yield the title compound (0.5 g, 20%) as a colourless solid, m.p. 171–172° C.

| Analysis % | | | |
|---|---|---|---|
| Found: | C, 65.04; | H, 5.63; | N, 10.88 |
| C$_{20}$H$_{16}$F$_2$N$_6$O$_2$ requires | C, 64.45; | H, 5.45; | N, 10.91 |

PREPARATION 48

(2R,3S/2S,3R)-2-(2,4-Difluorophenyl)-3-(4-acetylphenyl)-1-(1,2,4-triazol-1-yl)butan-2-ol

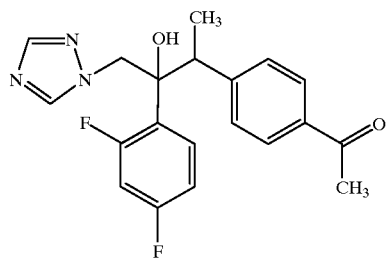

The title compound was prepared by a similar method to Preparation 47 using methyl-magnesium bromide, as a colourless solid

| Analysis % | | | |
|---|---|---|---|
| Found: | C, 64.43; | H, 5.09; | N, 11.31 |
| C$_{20}$H$_{19}$F$_2$N$_3$O$_2$ requires | C, 64.69; | H, 5.12; | N, 11.32 |

PREPARATION 49

N,O-Dimethyl-4-(2-[2,4-difluorophenyl]-2-hydroxy-1-[1,2,4-triazol-1-yl]but-3-yl)benzene hydroxamic acid

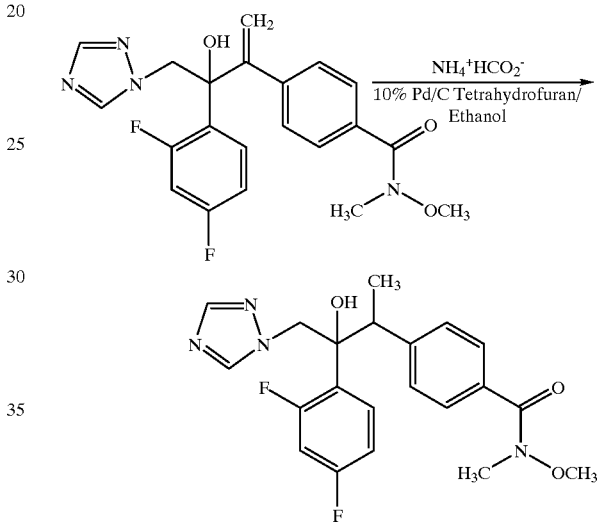

A mixture of N,O-dimethyl-4-(2-[2,4-difluorophenyl]-2-hydroxy-1-[1,2,4-triazol-1-yl]-3-buten-3-yl) benzene hydroxamic acid (0.9 g, 2.2 mmol-see Preparation 50), 10% palladium on charcoal (0.2 g) and ammonium formate (0.68 g, 11 mmol) was suspended in a tetrahydrofuran/ethanol (1:1, 40 ml) solution and heated under reflux for 3 hours. The cooled suspension was filtered through "Arbocel" and the filtrate was concentrated under reduced pressure. The residue was dissolved in ethyl acetate (50 ml) and the solution was washed with saturated sodium carbonate solution (20 ml) and brine (20 ml), then dried (Na$_2$SO$_4$) and evaporated under reduced pressure. The residue was purified by flash chromatography on silica by gradient elution with dichloromethane followed by dichloromethane/methanol (39:1). Fractions containing the desired product were combined and evaporated under reduced pressure to yield the title compound (0.5 g, 55%) as a colourless foam.

| Analysis % | | | |
|---|---|---|---|
| Found: | C, 60.17; | H, 5.40; | N, 13.11 |
| C$_{21}$H$_{22}$F$_2$N$_4$O$_3$ requires | C, 60.57; | H, 5.32; | N, 13.45 |

PREPARATION 50

N,O-Dimethyl-4-(2-[2,4difluorophenyl]-2-hydroxy-1-[1,2,4-triazol-1-yl]but-3-en-3-yl) benzene hydroxamic acid

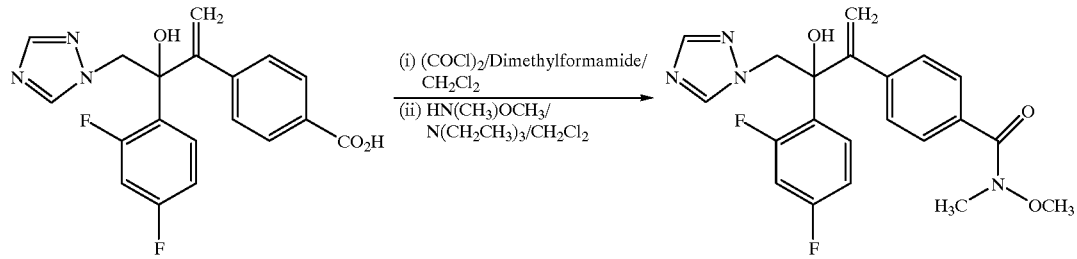

4-(2-[2,4-Difluorophenyl]-2-hydroxy-1-[1,2,4-triazol-1-yl]-3-buten-3-yl) benzoic acid (1.0 g, 2.7 mmol-see Preparation 25(i)) was converted into the acid chloride using the method of Preparation 25 part (ii). This intermediate was dissolved in dry dichloromethane (40 ml) and treated with N,O-dimethylhydroxylamine hydrochloride (0.31 g, 3.0 mmol). The suspension was cooled to 0° C. and treated with a solution of triethylamine (0.75 ml, 5.4 mmol) in dry dichloromethane. The mixture was allowed to warm to room temperature over 18 hours before being evaporated to dryness under reduced pressure. The residue was dissolved in ethyl acetate (100 ml) and was washed with saturated sodium carbonate solution (3×30 ml) and brine (3×30 ml). The organic layer was dried ($Na_2SO_4$) and evaporated under reduced pressure. The residue was flash chromatographed on silica by gradient elution with dichloromethane followed by dichloromethane/methanol (24:1).

Fractions containing the desired product were combined and evaporated under reduced pressure to yield the title compound (0.5 g, 55%) as a colourless foam, m.p. 154–156° C.

| Analysis % | | | |
|---|---|---|---|
| Found: | C, 60.70; | H, 4.67; | N, 13.30 |
| $C_{21}H_{20}F_2N_4O_3$ requires | C, 60.86; | H, 4.86; | N, 13.52 |

PREPARATION 51

2-(2,4-Difluorophenyl)-3-(4-[pyrazol-3-yl]phenyl)-1-(1,2,4-triazol-1-yl)-3-buten-2-ol

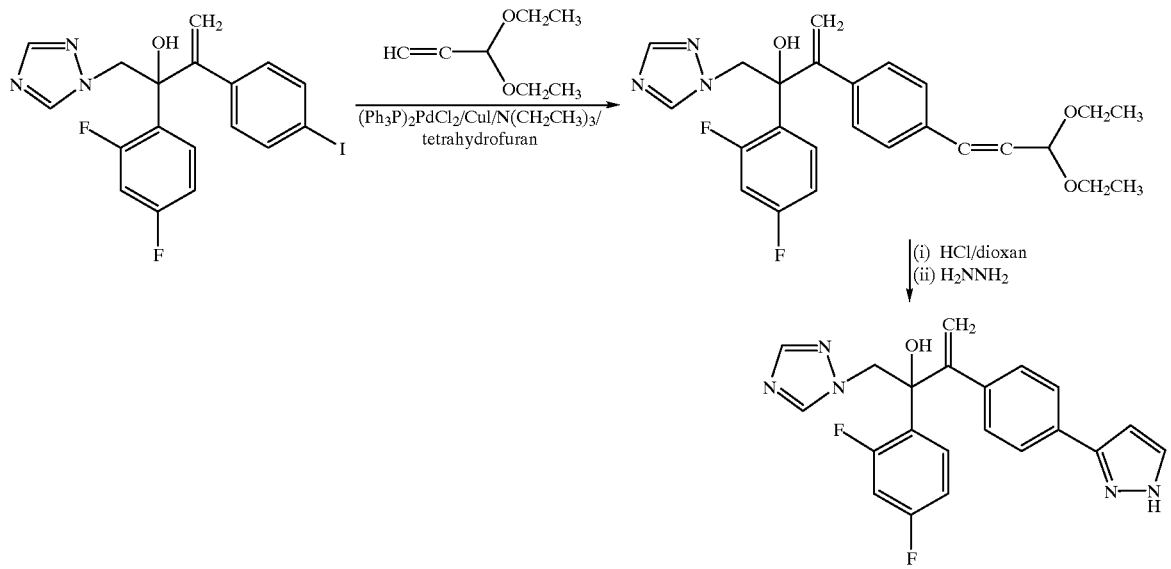

(i) A mixture of 2-(2,4-difluorophenyl)-3-(iodophenyl)-1-(1,2,4-triazol-1-yl)-3-buten-2-ol (4.0 g, 8.8 mmol-see Preparation 20), 3,3-diethyloxyprop-1-yne (1.52 ml, 10.6 mmol), copper(I)iodide (0.02 g) and bis(triphenylphosphine) palladium dichloride (0.12 g) In triethylamine (40 ml) and tetrahydrofuran (13 ml) was stirred at room temperature for 18 hours. The solvents were removed under reduced pressure and the residue was partitioned between dichloromethane (50 ml) and water (50 ml). The organic layer was dried ($MgSO_4$) and evaporated under reduced pressure. The residue was flash chromatographed on silica by elution with ethyl acetate. Fractions containing the desired product were combined and evaporated under reduced pressure to yield 2-(2,4-difluorophenyl)-3-(4-[3,3-diethoxyprop-1-yn-1-yl]phenyl)-1-(1,2,4-triazol-1-yl)-3-buten-2-ol as a yellow gum (2,4 g, 60%). Trituration with cyclohexane gave an off-white solid which was characterised by NMR.

$^1$H-NMR (300 MHz, CDCl$_3$): δ=1.28(t,6H), 3.67(q,2H), 3.83(q,2H), 4.56(d,1H), 4.94(d,1H), 5.16(s,1H), 5.30(d,2H), 5.50(s,1H), 6.6-6-8(m,2H), 7.23(d,2H), 7.39(d,2H), 7.45(m, 1H), 7.82(s,2H) ppm.

(ii) The product from part (i) (2,4 g, 5.3 mmol) was dissolved in dioxane (30 ml) and treated with dilute hydrochloride (2M, 6.6 ml) dropwise. The mixture was stirred at room temperature for 3 hours before addition of hydrazine hydrate (98%, 0.31 ml, 6.3 mmol) and stirring was continued at room temperature overnight. The solvents were removed under reduced pressure and the residue basified with sodium hydroxide solution before being extracted with dichloromethane (2×50 ml). The combined organic extracts were dried (MgSO$_4$) and evaporated under reduced pressure to give a yellow gum. The residue was flash chromatographed on silica by gradient ellution with hexane/ethyl acetate (1:3, 0:1) followed by ethyl acetate/methanol (9:1). Fractions containing the desired product were combined and evaporated under reduced pressure to yield 2-(2,4-difluorophenyl)-3-(4-pyrazol-3-ylphenyl)-1-(1,2,4-triazol-1-yl)-3-buten-2-ol (0.6 g, 29%) as a yellow solid, m.p. 182–184° C.

| Analysis % | | | |
|---|---|---|---|
| Found: | C, 64.51; | H, 4.39; | N, 17.81 |
| C$_{21}$H$_{17}$F$_2$N$_5$O requires | C, 64.12; | H, 4.35; | N, 17.80 |

PREPARATION 52

2-(2,4-Difluorophenyl)-3-(2-fluoro-[1-ethoxymethyl-1,2,3-triazol-5-yl]phenyl)-1-(1,2,4-triazol-1-yl)-3-buten-2-ol

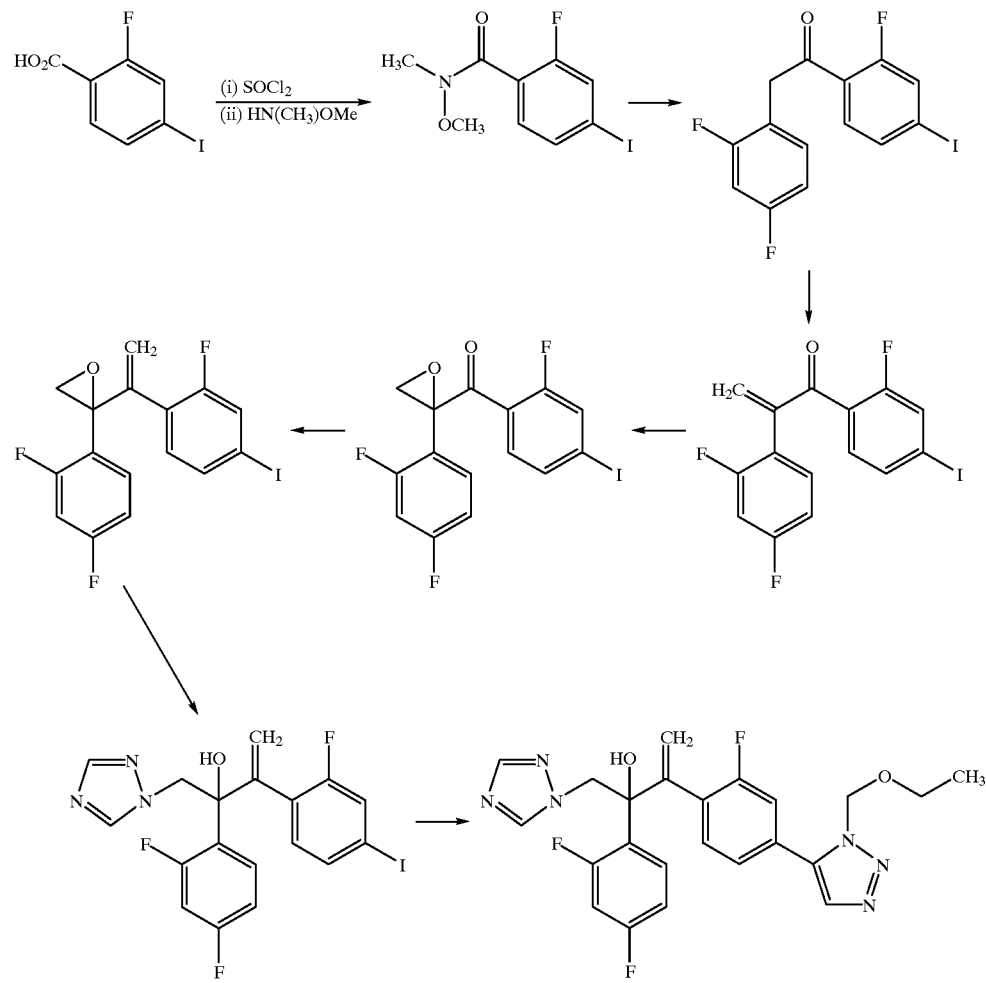

(i) N,O-Dimethyl-2-fluoro-4-iodobenzenehydroxamic acid

The product was prepared from 2-fluoro-4-iodo-benzoic acid (EP-A-0327190) and N,O-dimethylhydroxylamine hydrochloride by a similar method to Preparation 30, as a yellow oil, b.p. 120–122° C. (0.5 mmHg), which was characterised by NMR. $^1$H-NMR (300OMHz, CDCl$_3$): δ=3.44(s,3H), 3.53(s,3H), 7.14(t,1H), 7.51(d,1H), 7.56(dd, 1H) ppm.

(ii) 2-(2,4-Difluorophenyl)-1-(2-fluoro-4-iodophenyl)ethanone

The title compound was prepared using the product of part (i) by a similar method to Preparation 20(i), as a colourless solid, m.p. 81–82° C.

| Analysis % | | |
|---|---|---|
| Found: | C, 44.96; | H, 2.28; |
| $C_{14}H_8F_3IO$ requires | C, 44.71; | H, 2.14; |

(iii) 2-(2,4-Difluorophenyl)-1-(2-fluoro-4-iodophenyl)prop-2-enone

The title compound was prepared using the product of part (ii) by a similar method to Preparation 20(ii), as a colourless oil, which was characterised by NMR.

$^1$H-NMR (300 MHz, CDCl$_3$): δ=6.04 (s,1H), 6.15 (s,1H), 6.8–6.95(m,2H), 7.40(m,1H), 7.46(t,1H), 7.51 (dd,1H), 7.63 (dd,1H) ppm.

(iv) 2-(2,4-Difluorophenyl)-2-(2-fluoro-4-iodobenzoyl)oxirane

The title compound was prepared using the product of part (iii) by a similar method to Preparation 20(iii), as a colourless oil, which was characterised by NMR.

$^1$H-NMR (300 MHz, CDCl$_3$): δ=3.30(d,1H), 3.38(d,1H), 6.80(m,1H), 6.92(m,1H), 7.4–7.5(m,3H), 7.57(dd,1H) ppm.

(v) 2-(2,4-Difluorophenyl)-2-(1-[2-fluoro-4-iodophenyl]ethenyl)oxirane

The title compound was prepared using the product of part (iv) by a similar method to Preparation 20(iv), as a colourless oil, which was characterised by NMR.

1H-NMR (300 MHz, CDCl$_3$): δ=3.07(d,$_1$ H), 3.19(d,1H), 5.40(s,1H), 5.51(s,1H) 6.74(m,1H), 6.83(m,1H), 7.00(t,1H), 7.30–7.45(m,3H) ppm.

(vi) 2-(2,4-Difluorophenyl)-3-(2-fluoro-4-iodophenyl)-1-(1,2,4triazol-1-yl-3-buten-2-ol The title compound was prepared using the product of part by a similar method to Preparation 20(v) as a colourless solid, m.p. 136–138° C., which was characterised by NMR.

$^1$H-NMR (300 MHz, CDCl$_3$): δ=4.54(d,1H), 5.08(d,1H), 5.18(s,1H), 5.28(s,1H), 5.53(s,1H), 6.70(m,2H), 6.80(t,1H), 7.42(td,2H), 7.49(m,1H), 7.81 (s,1H), 7.95(s,1H) ppm.

(vii) 2-(2,4-Difluorophenyl)-3-(2-fluoro-4-[1-ethoxymethyl-1,2,3-triazol-5-yl]phenyl)-1-(1,2,4-triazol-1-yl)-3-buten-2-ol The title compound was prepared using the product of part (vi) by a similar method to Preparation 12, as a colourless oil, which was characterised by NMR.

$^1$H-NMR (300 MHz, CDCl$_3$): δ=1.21(t,3H), 3.73(q,2H), 4.60(d,1H), 5.08(d,1H), 5.30(s,1H), 5.36(s,1H), 5.56(s,1H), 5.65(s,2H), 6.6–6.8(m,2H), 7.10(t,1H), 7.3–7.6(m,3H), 7.64 (td,1H), 7.73(s,1H), 7.79(s,1H), 7.98(s,1H) ppm.

PREPARATIONS 53–58

The following compounds were prepared from (2R)-2-(2,4-difluorophenyl)-3-(4-iodophenyl)-1-(1H-1,2,4-triazol-1-yl)-3-buten-2-ol except in the case of Preparation 59 where the (2RS) starting material was uses and the appropriate 1-substituted heterocycle by a similar procedure to Preparation 12.

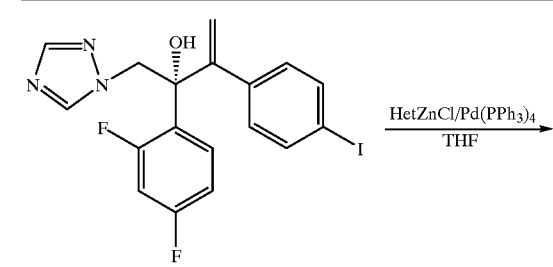

| Preparation No. | Het | M.p. (° C.) | $[\alpha]_D^{25}$ (c = 0.1%, MeOH). | Molecular Formula | Analysis % Calculated figures in brackets) | | |
|---|---|---|---|---|---|---|---|
| | | | | | C | H | N |

| | | | | | | | |
|---|---|---|---|---|---|---|---|
| 53 | (1,5-dimethylpyrazole) | Foam | −25.6 | C₂₂H₁₉F₂N₅O 0.5H₂O | 63.92 (63.45) | 4.86 (4.84) | 16.64 (16.82) |
| 54 | (1-ethyl-5-methylpyrazole) | Oil | — | C₂₃H₂₁F₂N₅O | Characterised by ¹H NMR. (see later) | | |
| 55 | (1-isopropyl-5-methylpyrazole) | Oil | — | C₂₄H₂₃F₂N₅O | Characterised by ¹H NMR. (see later) | | |
| 56 | (1-methyl-1,2,4-triazole) | Oil | — | C₂₁H₁₈F₂N₆O | Characterised by ¹H NMR. (see later) | | |
| 57 | (1,5-dimethyltetrazole) | Foam | −17.4 | C₂₀H₁₉F₂N₇O | 58.39 (58.08) | 4.71 (4.65) | 23.57 (23.83) |
| 58 | (1-benzyl-5-methyltetrazole) | Foam | — | C₂₆H₂₁F₂N₇O | Characterised by ¹H NMR. (see later) | | |
| 59 | (1,5-dimethyl-2-phenylthioimidazole) | Foam | — | C₂₈H₂₃F₂N₅OS | Characterised by ¹H NMR. (see later) | | |

PREPARATION 54

¹H-NMR(300 MHz, CDCl₃) δ=.1.41 (t, 3H), 4.16 (q, 2H), 4.63 (d, 1H), 4.97 (d, 1H), 5.14 (s, 1H), 5.32 (d, 2H), 6.26 (s, 1H), 6.69–6.79 (m, 2H), 7.32 (d, 2H), 7.47–7.55 (m, 2H), 7.81 (s, 1H), 7.84 (s, 1H)ppm.

PREPARATION 55

¹H-NMR(300 MHz, CDCl₃) δ=.1.46 (d, 3H), 1.48 (d, 3H), 4.53 (m, 1H), 4.63 (d, 1H), 4.97 (d, 1H), 5.12 (s, 1H), 5.32 (d, 2H), 6.22 (s, 1H), 6.73–6.79 (m, 2H), 7.27–7.55 (m, 6H), 7.81 (s, 1H), 7.84 (s, 1H)ppm.

PREPARATION 56

¹H-NMR(300 MHz, CDCl₃) δ=.3.99 (s, 3H), 4.62 (d, 1H), 4.97 (d, 1H), 5.25 (s, 1H), 5.29 (s, 1H), 5.35 (s, 1H), 6.71–6.77 (m, 2H), 7.42–7.49 (m, 3H), 7.59–7.61 (m, 2H), 7.81 (s, 1H), 7.83 (s, 1H), 7.92 (s, 1H)ppm.

PREPARATION 58

¹H-NMR(300 MHz, CDCl₃) δ=.4.60 (d, 1H), 4.95 (d, 1H), 5.11 (s, 1H), 5.34 (s, 1H), 5.38 (s, 1H), 5.60 (s. 2H), 6.65–6.80 (m, 2H), 7.14 (m 1H), 7.3–7.55 (m, 9H), 7.82 (s, 1H), 7.84 (s, 1H)ppm.

PREPARATION 59

¹H-NMR(300 MHz, COCl₃) δ=3.61 (s, 3H), 4.61 (d, 1H), 4.96 (d, 1H), 5.12 (s, 1H), 5.30 (s, 2H), 6.7–6.8 (m, 2H), 7.18–7.4 (m, 10H), 7.50 (q, 1H), 7,79 (s, 1H), 7.83 (s, 1H)ppm.

PREPARATION 60

2-(2,4-Difluorophenyl)-3-(4-[1-methylimidazol-5-yl]phenyl)-1-(1,2,4-triazol-1-yl)-3-buten-2-ol

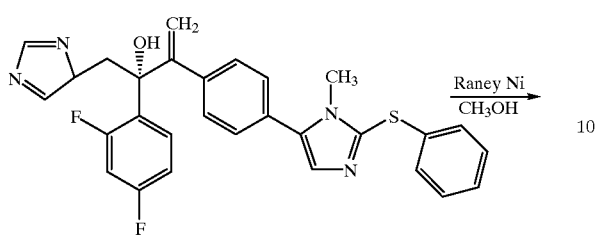

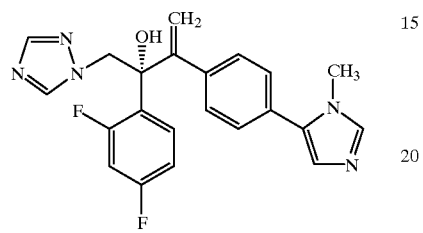

The title compound was prepared from 2-(2,4-difluorophenyl)-3-(4-[1-methyl-2-phenylthioimidazol-5-yl]phenyl)-1-(1,2,4-triazol-1-yl)-3-buten-2-ol, by a similar method to Example 35, as a colourless foam, which was characterised by $^1$H-NMR spectroscopy.

$^1$H-NMR(300 MHz, CDCl$_3$) δ=3.68 (s, 3H), 4.54 (d, 1H), 4.96 (d, 1H), 5.31 (s, 1H), 5.34 (s, 1H), 6.7–6.85 (m, 2H), 7.12 (s, 1H), 7.28 (s, 1H), 7.34 (d, 2H), 7.40 (d, 2H), 7.54 (m, 1H), 7.55 (s, 1H), 7.85 (s, 1H), 7.88 (s, 1H)ppm.

PREPARATION 61

(2R.3S/2S.3R)-2-(2,4-difluorophenyl)-3-(5-[1-triphenylmethyl-4-pyrazolyl]pyridin-2-yl)-1-(1,2,4-triazol-1-yl)butan-2-ol

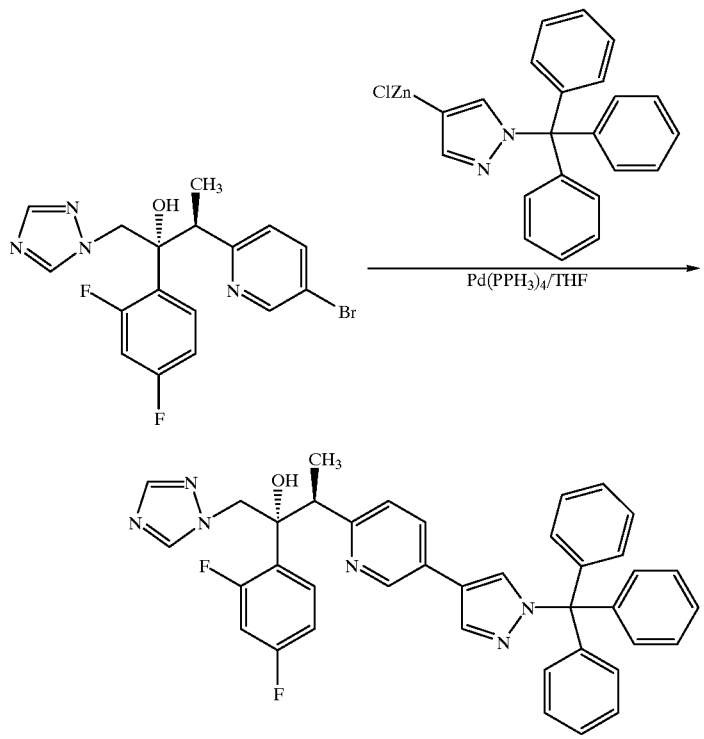

The title compound was prepared from 4-bromo-1-triphenylmethylpyrazole and (2R,3S/2S,3R)-2-(2,4-difluorophenyl)-3-(5-bromopyridin-2-yl)-1-(1,2,4-triazol-1-yl)butan-2-ol using a similar method to Example 82, to give the title compound as a colourless solid, m.p. 208–209° C., Analysis % Found: C, 73.44; H, 5.25; N, 13.13
C$_{29}$H$_{32}$F$_2$N$_6$O. requires: C, 73.34; H, 5.05; N, 13.16

PREPARATION 62

(2R,3S/2S,3R)-2-(2,4-Difluororohenyl)-3-(5-bromopyrid-2-yl)-1-(1,2,4-triazol-1yl)-butan-2-ol

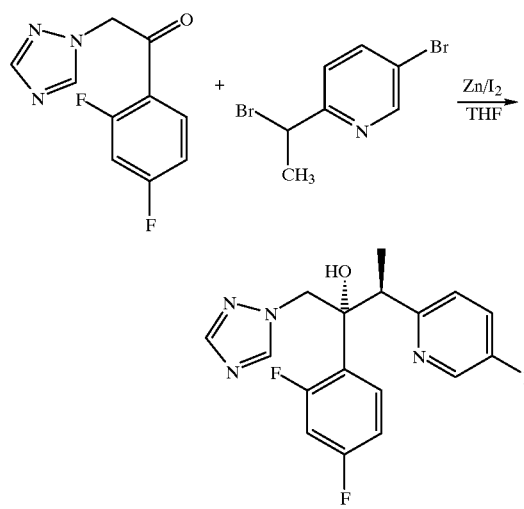

A solution of 2-(1-bromoethyl)-5-bromopyridine (1.32 g, 5 mmol) and 2-(1,2,4-triazol-1-yl)-2',4'-difluoroacetophenone (1.11 g, 5 mmol) in THF (12 ml) was added dropwise to a suspension of zinc (0.85 g, 13 mmol) in THF (8 ml) at room temperature under a nitrogen atmosphere. Iodine (0.25 g, 1 mmol) was added in one portion, resulting in an exothermic reaction which was not moderated. After the reaction mixture had returned to room temperature it was quenched by the addition of acetic acid (1 ml) and water (10 ml). Ethyl acetate (30 ml) and solid ethylenediaminetetraacetic acid di-sodium salt (3.72 g, 10 mmol) were added and the organic layer separated, dried ($MgSO_4$) and evaporated in vacuo. The crude product was purified by column chromatography (silica gel, eluting with 1:1 EtOAc:hexane) to give, after trituration with diethyl ether, the desired (2R,3S/2S,3R) diastereolsomer (0.62 g, 31%), m.p. 158–161° C. Found : C, 49.81; H, 3.55; N, 13.45; $C_{17}H_{15}BrF_2N_4O$ requires C, 49.90; H, 3.69; N, 13.69%.

Partial $^1$H-NMR(300 MHz, $CDCl_3$) δ=1.08 (d, 3H); 4.05, 4.78 (AB system, 2H)ppm.

Further elution of the above column with 2:1 EtOAc:hexane gave the minor (2R,3R/2S,3S) diastereoisomer which crystallised on standing (0.22 g, 11%), m.p. 82–83° C. Found: C, 49.96; H, 3.54; N, 13.70; $C_{17}H_{15}BrF_2N_4O$ requires C, 49.90; H, 3.69; N, 13.69%.

Partial $^1$H-NMR(300 MHz, $CDCl_3$) δ=1.50 (d, 3H); 4.66, 4.80 (AB system, 2H)ppm.

PREPARATION 63

(2R,3S)-2-(2,4-Difluorophenyl)-3-(5-bromopyrid-2-yl)-1-(1,2,4-triazol-1-yl)-butane-2-ol

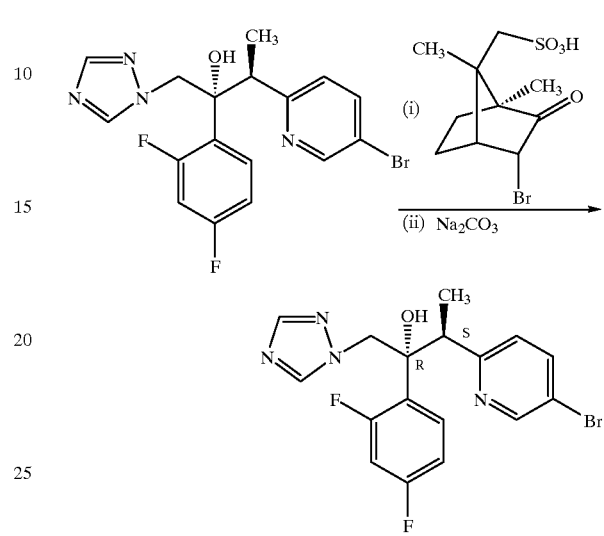

A solution of (2R,3S/2S,3R)-2-(2,4-Difluorophenyl)-3-(5-bromopyrid-2-yl)-1-(1,2,4-triazol-1-yl)-butan-2-ol (15.0 g, 37 mmol) was treated with a solution of (−)-3-Bromocamphor-8-sulphonic acid [generated from the ammonium salt (24.0 g, 73 mmol) by treatment of an ethanolic (250 ml) suspension with ethanolic HCl followed by filtration of the insoluble material] and stirred overnight at room temperature. The mixture was filtered and evaporated under reduced pressure. The residue was dissolved in acetone (60 ml) and stirred overnight at room temperature to yield a colourless suspension. The solid was collected by filtration and recrystallised twice from acetone to give (2R,3S)-2-(2,4-Difluorophenyl)-3-(5-bromopyrid-2-yl)-1-(1,2,4-triazol-1-yl)-butan-2-ol, (−)-3-Bromocamphor-8-sulphonate salt (14.4 g). The optical purity of the product was assessed as 92% ee by hplc analysis using a Chiralcel™ OD column by elution with ethyl acetate/hexane (20:80).

The solid was suspended in water (100 ml), basified with saturated sodium carbonate solution and extracted with ethyl acetate (3×100 ml). The combined organic extracts were washed with brine (3×50 ml), dried ($Na_2SO_4$) and evaporated to give a colourless oil. The oil was dissolved in ether and evaporated to give the title compound as a foam (4.23 g, 56% of theoretical yield).

Analysis % Found: C, 49.61; H, 3.28; N, 13.46 $C_{17}H_{15}BrF_2N_4O$. requires: C, 49.90; H, 3.69; N, 13.69

PREPARATION 64

2-(1-Bromoethyl)-5-bromopyridine

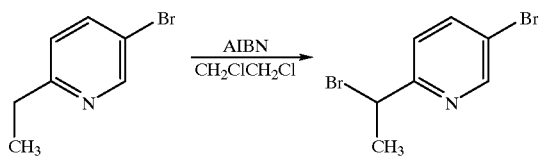

A solution of 2-ethyl-5-bromopyridine (1.86 g, 10 mmol), N-bromosuccinimide (1.78 g, 10 mmol) in 1,2-dichloroethane (20 ml) was brought to reflux before the addition of azoisobutyronitrile (AIBN) (20 mg). The solution was then refluxed for a further two hours. The cooled suspension was filtered and evaporated in vacuo. Purification by column chromatography (silica gel, eluting with 1:1 dichloromethane/hexane) gave the desired product as a pale yellow oil (2.12 g, 80%).

$^1$H-NMR(300 MHz, CDCl$_3$) δ=2.05 (d, 3H); 5.20 (q, 1H); 7.35 (d, 1H); 7.8 (m, 1H); 8.6 (d, 1H)ppm.

PREPARATION 65

2-Ethyl-5-bromopyridine

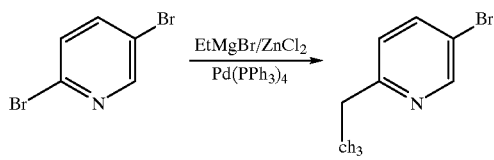

A solution of ethylmagnesium bromide in ether (100 ml, 3M, 0.3 mol) was added dropwise to a cold (5° C.) solution of anhydrous zinc chloride (40.9 g, 0.3 mol) in THF (500 ml) under nitrogen. After stirring for one hour at 0° C., tetrakis(triphenylphosphine)-palladium (0) (1.0 g, 0.87 mmol) was added followed by a solution of 2,5-dibromopyridine (50 g, 0.21 mol) in THF (200 ml). The resulting yellow suspension was stirred at room temperature overnight, quenched by the addition of water (200 ml) and then evaporated in vacuo. The residue was treated with a suspension of ethylenediaminetetraacetic acid (200 g) in water (1000 ml) and dichloromethane (500 ml). The organic layer was separated and the aqueous layer again extracted with dichloromethane (500 ml). The combined extracts were dried (MgSO$_4$), solvent evaporated in vacuo, and the residue distilled (123–124° C., 60 mmHg) to give the required product as a colourless oil (28.8 g, 76%).

$^1$H-NMR(300 MHz, CDCl)=1.30 (t, 3H); 2.80 (q, 2H); 7.10 (d, 1H); 7.7 (dd, 1H); 8.6 (d, 1H)ppm.

PREPARATION 66

1-Ethoxymethylr vrazole

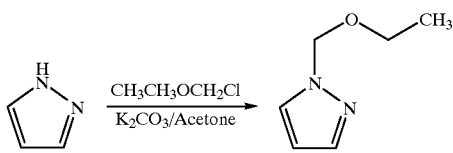

The title compound was prepared by a similar method to Preparation 26 as a colourless oil, b.p. 100° C. @15 mmHg (Kugelrohr), which was characterised by $^1$H-NMR spectroscopy. $^1$H-NMR(300 MHz, CDCl$_3$) δ=1.16 (t, 3H), 3.52 (q, 2H), 5.43 (s, 2H), 6.33 (t, 1H), 7.58 (m, 2H)ppm.

PREPARATION 67

(2R,3S/2S,3R)-2-(2,4-Difluorophenyl)-3-(2-trifluoromethylsulphonyloxy-1-yl)ridin-5-yl)-1-(1,2,4-triazol-1-yl)butan-2-ol

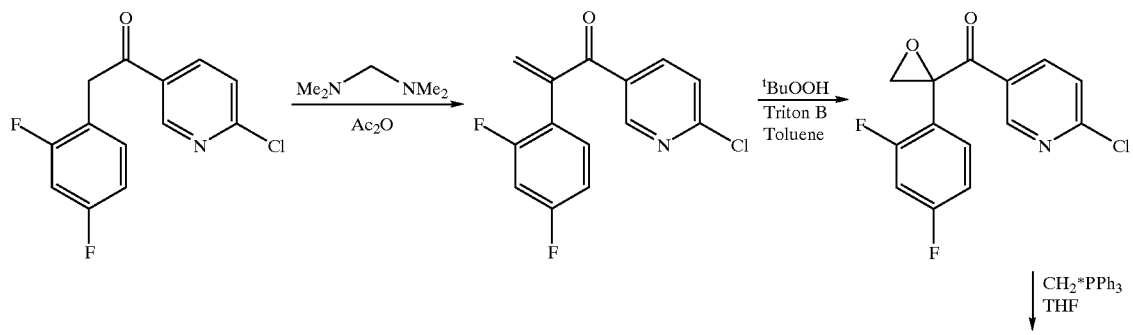

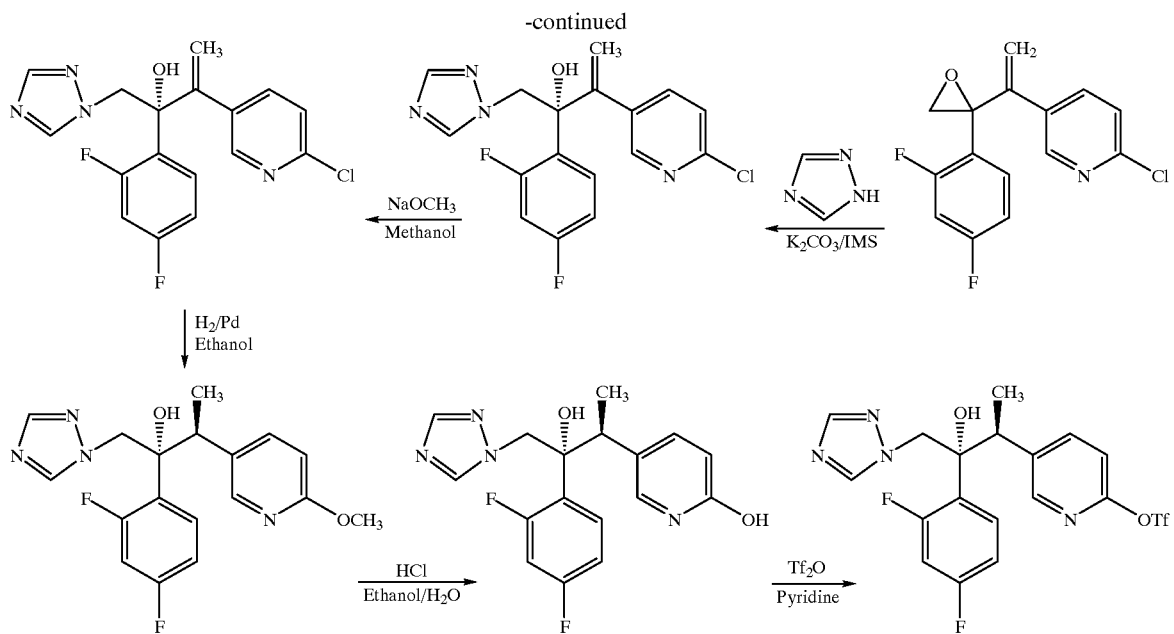

(i) 1-(2-Chlorocvridin-5-yl)-2-(2,4-difluorophenyl)prop-2-enone

The title compound was prepared from the product of Preparation 22 part (ii) by a similar method to that described in Preparation 20(ii), as a colourless solid, m.p. 111–112° C., which was characterised by ¹H-NMR spectroscopy.

¹H-NMR(300 MHz, CDCl₃) δ=5.95 (s, 1H), 6.20 (s, 1H), 6.80 (m, 1H), 6.90 (m, 1H), 7.40 (q, 1H), 7.45 (d, 1H), 8.10 (dd, 1H), 8.80 (s, 1H)ppm.

(ii) 2-(2-Chlororvridin-5-carbonyl)-2-(2,4-difluorophenyl)oxirane

The title compound was prepared from the product of part (i) by a similar method to that described in Preparation 20(iii), as a yellow oil, which was characterised by ¹H-NMR spectroscopy.

¹H-NMR(300 MHz, CDCl₃) δ=3.25 (d, 1H), 3.40 (d, 1H), 6.80 (m, 1H), 6.95 (m, 1H), 7.40 (d, 1H), 7.45 (q, 1H), 8.25 (dd, 1H), 9.00 (s, 1H)ppm.

(iii) 2-(2-Chloroyvridin-5-yl)ethenyl-2-(2,4-difluorophenyl)oxirane

The title compound was prepared from the product of part (ii) by a similar method to that described in Preparation 20(iv), as a yellow oil, which was characterised by ¹H-NMR spectroscopy.

¹H-NMR(300 MHz, CDCl₃) δ=3.15 (q, 2H), 5.50 (d, 2H), 6.70 (m, 1H), 6.90 (m, 1H), 7.25 (d, 1H), 7.40 (q, 1H), 7.70 (d, 1H), 8.40 (s, 1H)ppm.

(iv) (2R,3S/2S,3R)-2-(2,4-Difluorophenyl)-3-(2-chloropyridin-5-yl)-1-(1,2,4-triarol-1-yl)-3-buten-2-ol The title compound was prepared from the product of part (iii) by a similar method to that described in Preparation 20(v), as a colourless solid m.p.116–119° C., which was characterised by ¹H-NMR spectroscopy.

¹H-NMR(300 MHz, CDCl₃) δ=4.60 (d, 1H), 5.00 (d, 1H), 5.35 (s, 1H), 5.40 (d, 2H), 6.65–6.80 (m, 2H), 7.20 (d, 1H), 7.40 (q, 1H), 7.60 (dd, 1H), 7.80 (s, 1H), 7.85 (s, 1H), 8.20 (s, 1H)ppm.

(v) (2R,3S/2S,3R)-2-(2,4-Difluorophenyl)-3-(2-methoxypyridin-5-yl)-1-(1,2,4-triazol-1-yl)-3-buten-2-ol A solution of (2R,3S/2S,3R)-2-(2,4-Difluorophenyl)-3-(2-chloropyridin-5-yl)-1-(1,2,4-triazol-1-yl)-3-buten-2-ol (10.27 g, 28 mmol) in methanol (20 ml) was treated with a solution of sodium methoxide [from sodium (1.3 g, 56 mmol) and methanol(30 ml)] and the solution heated under reflux for 18 hours. Additional batches of sodium methoxide solution (from 2×3.25 g 0.28 mol total of sodium) were added over 4 days at reflux. The mixture was diluted with water (100 ml) and evaporated under reduced pressure. The residue was partitioned between water (100 ml) and dichloromethane (100 ml). The organic phase was washed with water (50 ml), dried (MgSO₄) and evaporated under reduced pressure.

The residue was chromatographed on silica by gradient elution with dichloromethane/methanol (100:0→98:2). Fractions containing the desired product were combined and evaporated under reduced pressure to give yellow oil (10.15 g, quantitative) which was characterised by ¹H-NMR spectroscopy as a 93:7 mixture of product:starting material.

¹H-NMR(300 MHz, CDCl₃) δ=3.90 (s, 3H), 4.60 (d, 1H), 5.00 (d, 1H), 5.27 (s, 1H), 5.30 (d, 2H), 6.60 (d, 1H)6.65–6.80 (m, 2H), 7.45 (q, 1H), 7.55 (dd, 1H), 7.80 (s, 1H), 7.85 (s, 1H), 8.05 (d, 1H)ppm.

(vi) (2R,3S/2S,3R)-2-(2,4-Difluorochenyl)-3-(2-methoxypyridin-5-yl)-1-(1,2,4-triazol-1-yl)butan-2-ol The title compound was prepared from the product of part (v) by a similar method to that described in Example 1, as a colourless solid m.p. 94–96° C., which was characterised by ¹H-NMR spectroscopy.

¹H-NMR(300 MHz, CDCl₃) δ=1.10 (d, 3H), 3.30 (q, 1H), 3.85 (d, 1H), 3.95 (s, 3H), 4.80 (d, 1H), 4.90 (s, 1H), 6.70 (m, 2H), 6.80 (d, 1H), 7.45 (q, 1H), 7.74 (s, 1H), 7.76 (s, 1H), 7.85 (dd, 1H), 8.20 (d, 1H)ppm.

(vii) (2R,3S/2S,3R)-2-(2,4-Difluorophenyl)-3-(2-hudroxypyridin-5-yl)-1-(1,2,4-triazol-1-yl)butan-2-ol A solution of (2R,3S/2S,3R)-2-(2,4-Difluorophenyl)-3-(2-methoxypyridin-5-yl)-1-(1,2,4-triazol-1-yl)butan-2-ol (7.06 g, 1 9.6 mmol) in ethanol (50 ml) was treated with dilute hydrochloric acid (2M, 20 ml) and the mixture was heated under reflux for 84 hours. The mixture was evaporated under reduced pressure and the residue triturated with water to yield the title compound as a colourless solid (4.05, 60%), m.p. 213–214° C., which was characterised by ¹H-NMR spectroscopy.

¹H-NMR(300 MHz, DMSO) δ=0.90 (d, 3H), 3.30 (q, 1H), 4.10 (d, 1H), 4.80 (d, 1H), 5.55 (s, 1H), 6.30 (d, 1H), 6.85 (m, 1H), 7.10 (m, 1H), 7.20 (q, 1H), 7.25 (d, 1H), 0.00 (dd, 1H), 7.60 (s, 1H), 8.15 (s, 1H), 11.50 (br.s, 1H)ppm.

(viii) (2R,3S/2S,3R)-2-(2,4-Difluorophenyl)-3-(2-trifluoromethylsulihonyloxy-pyridin-5-yl)-1-(1,2,4-triazol-1-yl)butan-2-ol A suspension of (2R,3S/2S,3R)-2-(2,4-Difluorophenyl)-3-(2-hydroxypyridin-5-yl)-1-(1,2,4-triazol-1-yl)butan-2-ol (2.0 g, 5.8 mmol) in pyridine (15 ml) was treated with trifluoromethanesulphonic anhydride (2.14 ml, 11.6 mmol) at 0° C. The yellow solution was stirred at 0° C. for 0.25 hours and allowed to warm to room temperature overnight. Water (10 ml) was added and the mixture partitioned between dichloromethane (50 ml) and saturated aqueous sodium carbonate solution; the organic phase was dried (MgSO₄) and evaporated under reduced pressure.

The residue was chromatographed on silica by gradient elution with dichloromethanel methanol (100:0→98:2). Pure fractions containing the desired product were combined and evaporated under reduced pressure to give a colourless oil, which was triturated with ether to give the title compound as a solid (0.71 g, 26%), m.p. 172–173° C., which was characterised by ¹H-NMR spectroscopy.

¹H-NMR(300 MHz, CDCl₃) δ=1.15 (d, 3H), 3.40 (q, 1H), 3.80 (d, 1H), 4.80 (d, 1H), 5.10 (s, 1H), 6.80 (m, 2H), 7.20 (d, 1H), 7.45 (q, 1H), 7.74 (s, 1H), 7.76 (s, 1H), 0.00 (dd, 1H), 8.40 (d, 1H)ppm.

PREPARATION 68

1-methylpyrazol-5-yl-trimethylstannane

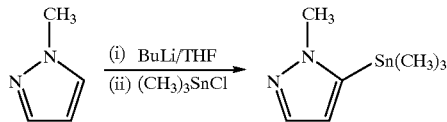

Butylithium (2.5M in hexane, 9.75 ml, 24.4 mmol) was added to a stirred solution of 1-methylpyrazole (2.0 g. 24.4 mmol) in THF (30 ml) at −78° C. After 0.15 hours, a solution of chlorotrimethylstannane (4.85 g, 24.4 mmol) was added dropwise and the mixture allowed to warm to room temperature. The mixture was evaporated under reduced pressure and the residue partitioned between ether (50 ml) and water (50 ml). The ether layer was dried (MgSO₄) and evaporated to yield the title compound as colourless oil (6.0 g, quantitative), which was characterised by ¹H-NMR spectroscopy.

¹H-NMR(300 MHz, CDCl₃) δ=0.35 (s, 9H), 3.95 (s, 3H), 6.30 (s, 1H), 7.50 (s, 1H)ppm.

PREPARATION 69

(2R,3S) N-methyl-4-{2-[2,4-difluorophenyl]-2-hydroxy-1-[1,2,4-triazol-1-yl]but-3-yl}benzoylthiosemicarbazide

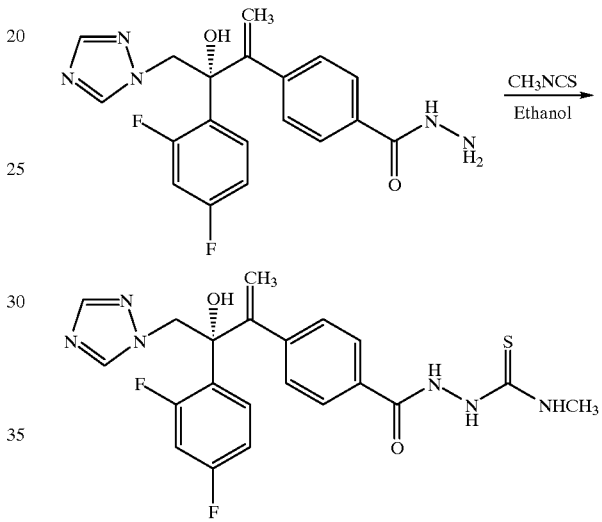

Solid methyl isothiocyanate (0.38 g, 5.2 mmol) was added to a solution of (2R,3S) N-methyl-4-{2-[2,4-difluorophenyl]-2-hydroxy-1-[1,2,4-triazol-1-yl]but-3-yl}benzoylhydrazide (2.0 g, 5.2 mmol-prepared from the product of Preparation 20 by the method of Preparation 23) in ethanol (20 ml). The mixtures was heated under reflux overnight and evaporated to dryness under reduced pressure. The residue was partitioned between ethyl acetate (150 ml) and saturated sodium bicarbonate solution (35 ml). The aqueous phase was extracted with ethyl acetate (50 ml) followed by dichloromethane/methanol (95:5). The organic extracts were combined, washed with brine (40 ml) and dried (Na₂SO₄), then evaporated under reduced pressure.

The residue was chromatographed on silica by gradient elution with dichloromethane/methanol (98:2→92:8). Pure fractions containing the desired product were combined and evaporated under reduced pressure to give a colourless oil, which was triturated with ether to give the title compound as a solid (2.1 g, 85%), m.p. 172–173° C., which was characterised by ¹H-NMR spectroscopy.

¹H-NMR(300 MHz, CDCl₃) δ=0.9 (d, 3H), 2.8 (d, 1H), 3.2 (q, 1H), 3.6 (d, 1H), 4.6 (d, 1H), 4.8 (s, 1H), 5.1 (s, 1H), 6.5 (m, 2H), 7.2 (m, 2H), 7.3 (d, 2H), 7.4 (s, 1H), 7.7 (m, 3H), 8.7 (br.s, 1H), 9.8 (br.s, 1H)ppm

PREPARATION 70

(2R,3S)-2-(2,4-Difluorophenyl)-3-(4-[3-methyl-5-trimethylsilylpropyl-4-yl]phenyl)-1-(1,2,4-triazol-1-yl)butan-2-ol

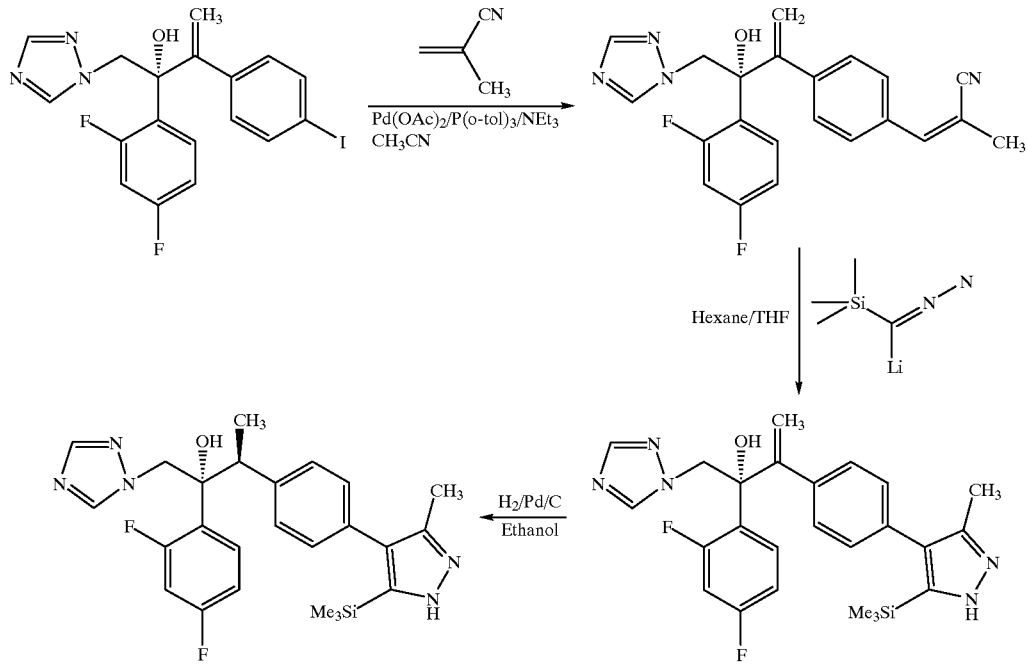

(i) (2R, E/Z)-2-(2,4-Difluorophenyl)-3-(4-[2-cyano-1-propenyl]phenyl)-1-(1,2,4-triazol-1-yl)-3-buten-2-ol A suspension of (2R)-2-(2,4-Difluorophenyl)-3-(4-iodophenyl)-1-(1,2,4-triazol-1-yl)-3-buten-2-ol [2.0 g, 4.4 mmol-Example 66 part (i)], palladium acetate (0.05 g), triethylamine (1.0 ml) and tri(ortho-tolyl)phosphine (0.14 g) in acetonitrile (50 ml) was treated with methacrylonitrile (0.74 ml, 8,8 mmol) and the mixture heated under reflux for 70 hours. The same quantities of each of the reagents was added and the mixture returned to reflux for 3 hours. The mixture was evaporated under reduced pressure and the residue was partitioned between ethyl acetate (30 ml) and saturated sodium bicarbonate (20 ml). The organic phase was washed with brine (30 ml), dried ($Na_2SO_4$), and evaporated under reduced pressure.

The residue was chromatographed on silica by gradient elution with dichloromethane/methanol (98:2→92:8). Pure fractions containing the desired product were combined and evaporated under reduced pressure to give a colourless solid, (1.3 g, 75%), which was characterised by mass spectroscopy, m/z=393

(ii) (2R)-2-(2,4-Difluorophenyl)-3-(4-[3-methyl-5-trimethylsilylpropyl-4-yl]phenyl)-1-(1,2,4-triazol-1-yl)-3-buten-2-ol Butyllithium (2.5M in hexanes, 4.0 ml, 10 mmol) was added dropwise to a solution of trimethylsilyldiazomethane (2.0M in hexanes, 5.0 ml, 10 mmol) in THF (20 ml) at −78° C. After stirring for 0.25 hours, a solution of (2R)-2-(2,4-Difluorophenyl)-3-(4-[2-cyano-1-propenyl]phenyl)-1-(1,2,4-triazol-1-yl)-3-buten-2-ol (1.3 g, 3.3 mmol) was added dropwise to give a brown solution which was allowed to warm to room temperature overnight. The mixture was quenched with saturated ammonium chloride solution (20 ml) and extracted with dichloromethane (30 ml). The organic layer was washed with water (30 ml), brine (15 ml), dried ($Na_2SO_4$), and evaporated under reduced pressure.

The residue was chromatographed on silica by gradient elution with dichloromethane/methanol (100:0→98:2). Pure fractions containing the desired product were combined and evaporated under reduced pressure to give a colouriess solid, (0.65 g, 41%), which was characterised by $^1$H-NMR spectroscopy as a 2:1 mixture of tautomers.

$^1$H-NMR(300 MHz, $CDCl_3$) δ=0.05 (s, 6H), 0.20 (s, 3H), 2.16 (s, 2H), 3.94 (s, 1H), 4.52 (d, 0.3H), 4.62 (d, 0.7H), 4.87 (d, 0.3H), 4.93 (d, 0.7H), 4.97 (br.s, 0.3H), 5.13 (br.s, 0.7H), 5.15 (s, 0.7H), 5.20 (s, 0.3H), 5.30 (s, 2H), 6.55–6.7 (m, 2H), 7.10 (d, 1.4H), 7.14 (d, 0.6H), 7.22 (d, 1.4H), 7.42 (m, 1H), 7.75 (s, 0.7H), 7.78 (s, 1.3H)ppm.

(iii) (2R,3S)-2-(2,4-Difluorophenyl)-3-(4-[3-methyl-5-trimethysilylyltyrazol-4-yl]phenyl)-1-(1,2,4-triazol-1-yl)butan-2-ol The title compound was prepared from the product of part (ii) by a similar method to that described in Example 1, as a pale yellow solid, which was characterised by $^1$H-NMR spectroscopy.

$^1$H-NMR(300 MHz, $CDCl_3$) δ=0.15 (s, 9H), 2.25 (s, 3H), 3.35 (q, 1H), 3.87 (d, 1H), 4.80 (br.s, 1H), 4.87 (d, 1H), 6.75 (m, 2H), 7.22 (d, 2H), 7.4–7.5 (m, 3H), 7.72 (s, 1H), 7.78 (s, 1H)ppm.

PREPARATION 71

(2-(1-bromoethyl)-5-(1,2,3-triazol-2-yl)pyridine

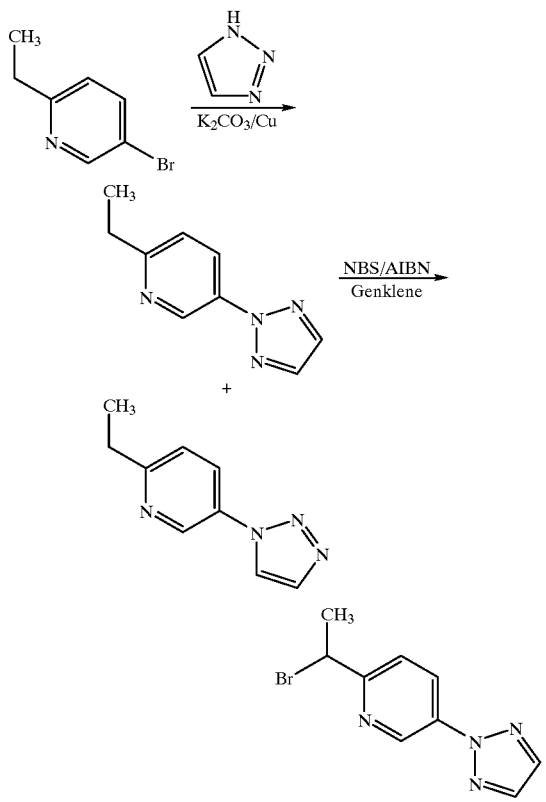

(i) 2-ethyl-5-(1,2,3-triazol-2-yl)pyridine

The title compound was prepared from 5-bromo-2-ethylpyridine (Preparation 65) and 1,2,3-triazole by a similar method to Preparation 1. The regioisomeric product were separated by column chromatography on silica by gradient elution with ethyl acetate/hexane (1:1→1:0). Fractions containing the title compound eluted first, these were combined and evaporated under reduced pressure to yield an oil, which was distilled b.p.135° C. @ 0.05 mmHg (Kugelrohr).

(ii) 2-(1-bromoethyl)-5-(1,2,3-triazol-2-yl)pyridine

The title compound was prepared by the method of Preparation 64 using 1,1,1-trichloroethane (Genklene) as solvent, as a colourless solid, m.p. 72–73° C.

Analysis % Found: C, 42.85; H, 3.68; N, 22.70
$C_9H_9BrN_4$. requires: C, 42.71; H, 3.58; N, 22.14

PHARMACOLOGICAL DATA

Candidosis in Immune-normal Mice

Mice were infected intravenously with *Candida albicans* in order to establish a systemic infection (all untreated control animals died by 2 days post-infection). Compound efficacy was assessed on basis of survival after oral dosing (0.1–5 mg/kg, 1, 4 and 24 hours post-infection) and was measured as the dose protecting 50% of animals on day 2 post-infection.

Results:

| Compound of Example No. | $PD_{50}$(mg/kg) |
|---|---|
| 3 | 0.32 |
| 4 | 0.10 |
| 6 | 0.04 |
| 15 (2R,3S/2S,3R form) | 0.56 |
| 36 | 0.18 |
| 38 | 0.10 |

Safety Data

The compounds have not been found to exhibit any adverse toxicity. For example, in a 7-day toxicity study in rats (80 mg/kg p.o, o.d.) the products of Examples 3 and 15 (2R,3S/2S,3R diasteromer) showed no adverse effects.

The compounds are also useful as plant antifungal agents.

We claim:

1. A compound of formula (I)

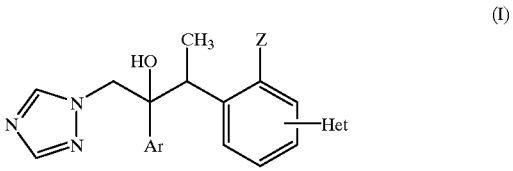

(I)

or a pharmaceutically acceptable salt thereof, wherein:

Ar is phenyl substituted by 1 to 3 substituents each independently selected from halo and $CF_3$;

Z is H or F; and,

Het is pyrazolyl optionally substituted by 1 to 3 substituents each independently selected from halo, $C_1$–$C_4$ alkyl, ($C_1$–$C_4$ alkoxy)methyl, 2-($C_1$–$C_4$ alkoxy)ethoxymethyl, 2-hydroxyethoxymethyl, cyanomethyl, phenylthio, phenyl-substituted $C_1$–$C_2$ alkyl, —NHC(O)($C_1$–$C_4$ alkyl), —NHSO$_2$($C_1$–$C_4$ alkyl), —S(O)$_n$ ($C_1$–$C_4$ alkyl) where n is an integer from 0 to 2, —NHC(O)NR$^1$R$^2$, —NR$^1$R$^2$ and —CH$_2$C(O)NR$^1$R$^2$ where R$^1$ and R$^2$ are each independently H or $C_1$–$C_4$ alkyl, and the phenyl groups of the foregoing Het groups are optionally substituted by halo, trifluoromethyl, or $C_1$–$C_4$ alkyl.

2. A compound as claimed in claim 1 in which Z is H.

3. A compound as claimed in claim 2 wherein "Het" is substituted by 1 or 2 substituents each independently selected from chloro, bromo, fluoro, iodo, $C_1$–$C_3$ alkyl, amino, ethoxymethyl, 2-methoxyethoxymethyl, 2-hydroxyethoxymethyl, methylthio, methanesulphonyl, mercapto, phenylthio, methanesulfonamido, 3-methylureido, cyanomethyl, carbamoylmethyl, acetamido and benzyl.

4. A compound as claimed in claim 1 wherein Ar is a phenyl group substituted by 1 or 2 substituents each independently selected from halo and $CF_3$.

5. A compound as claimed in claim 4 wherein Ar is a phenyl group substituted by 1 or 2 substituents each independently selected from F, Cl and Br.

6. A compound as claimed in claim 5 wherein Ar is 2,4-difluorophenyl, 2-chlorophenyl or 2-fluorophenyl.

7. A pharmaceutical composition comprising a compound of the formula (I) or pharmaceutically acceptable salt thereof as claimed in claim 1, and a pharmaceutically acceptable diluent or carrier.

8. A method of treating or preventing a fungal infection in a human patient, which comprises administering to said patient an effective amount of a compound of the formula (i) or salt thereof as claimed in claim 1.

* * * * *